United States Patent
Willaert et al.

(10) Patent No.: US 12,222,275 B2
(45) Date of Patent: Feb. 11, 2025

(54) METHODS AND SYSTEMS FOR PARTICLE CHARACTERISATION BY IMAGING FREE-FLOATING PARTICLE MOVEMENT IN LIQUID ENVIORNMENT

(71) Applicants: VRIJE UNIVERSITEIT BRUSSEL, Brussels (BE); ECOLE POLYTECHNIQUE FÉDÉRALE DE LAUSANNE, Lausanne (CH)

(72) Inventors: Ronnie Willaert, Hoeilaart (BE); Sandor Kasas, Pully (CH); Pieterjan Vanden Boer, Etterbeek (BE); Anton Malovichko, Lausanne (CH); Mitchel Perez Gonzalez, Brussels (BE); Hichem Sahli, Brussels (BE)

(73) Assignees: VRIJE UNIVERSITEIT BRUSSEL, Brussels (BE); ECOLE POLYTECHNIQUE FÉDÉRALE DE LAUSANNE, Lausanne (CH)

( * ) Notice: Subject to any disclaimer, the term of this patent is extended or adjusted under 35 U.S.C. 154(b) by 499 days.

(21) Appl. No.: 17/595,280

(22) PCT Filed: Apr. 30, 2020

(86) PCT No.: PCT/EP2020/062143
§ 371 (c)(1),
(2) Date: Nov. 12, 2021

(87) PCT Pub. No.: WO2020/229201
PCT Pub. Date: Nov. 19, 2020

(65) Prior Publication Data
US 2022/0283074 A1    Sep. 8, 2022

(30) Foreign Application Priority Data
May 13, 2019 (EP) .................... 19174250

(51) Int. Cl.
*G01N 15/14* (2024.01)
*C12Q 1/02* (2006.01)
(Continued)

(52) U.S. Cl.
CPC ......... *G01N 15/1434* (2013.01); *C12Q 1/025* (2013.01); *C12Q 1/18* (2013.01); *G06N 3/08* (2013.01); *A61B 5/1405* (2013.01)

(58) Field of Classification Search
None
See application file for complete search history.

(56) References Cited

U.S. PATENT DOCUMENTS 9,239,524 B2 * 1/2016 Kida ................. G03F 7/70341
2011/0228256 A1   9/2011 Allier
(Continued)

FOREIGN PATENT DOCUMENTS

CN   101903532 A    12/2010
CN   105008895 A    10/2015
(Continued)

OTHER PUBLICATIONS

Chinese Office Action dated Nov. 9, 2023 in Application No. 202080043308.8.
(Continued)

*Primary Examiner* — Haris Sabah
(74) *Attorney, Agent, or Firm* — Sughrue Mion, PLLC

(57) ABSTRACT

A method and system for deriving particle characteristics is described. The method comprises imaging the movement of at least one free-floating particle in a liquid environment at at least one moment in time, determining for at least one moment in time a movement parameter based on the imaged movement of the free-floating particles in the liquid environment, and deriving from the movement parameter a characteristic of the at least one particle.

31 Claims, 72 Drawing Sheets

(51) Int. Cl.
*C12Q 1/18* (2006.01)
*G01N 15/1434* (2024.01)
*G06N 3/08* (2023.01)
*A61B 5/15* (2006.01)

(56) References Cited

U.S. PATENT DOCUMENTS

2015/0268244 A1  9/2015  Cho et al.
2015/0362420 A1* 12/2015  Espinoza Vallejos ............... G01N 15/1031
                                                                324/450
2018/0216155 A1  8/2018  Son et al.

FOREIGN PATENT DOCUMENTS

| CN | 108693095 A | 10/2018 |
| CN | 207964569 U | 10/2018 |
| EP | 2 270 198 A1 | 1/2011 |
| JP | H08-506179 A | 7/1996 |
| JP | 2016-057307 A | 4/2016 |
| WO | 94/16821 A1 | 8/1994 |

OTHER PUBLICATIONS

Sandor Kasas et al., "Detecting nanoscale vibrations as signature of life", PNAS, Jan. 13, 2015, pp. 378-381, vol. 112, No. 2.
International Search Report for PCT/EP2020/062143 dated, Aug. 21, 2021 (PCT/ISA/210).
Written Opinion of the International Search Report for PCT/EP2020/062143 dated, Aug. 21, 2021 (PCT/ISA/237).
European Office Action issued Feb. 15, 2024 in Application No. 20 721 634.2.
Japanese Office Action issued Jan. 9, 2024 in Application No. 2021-568060.

* cited by examiner

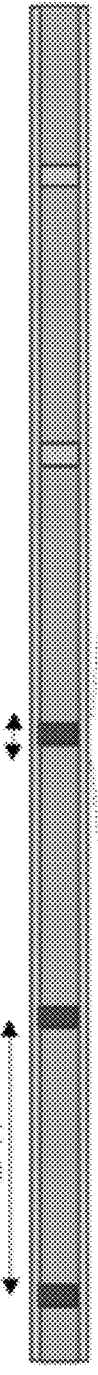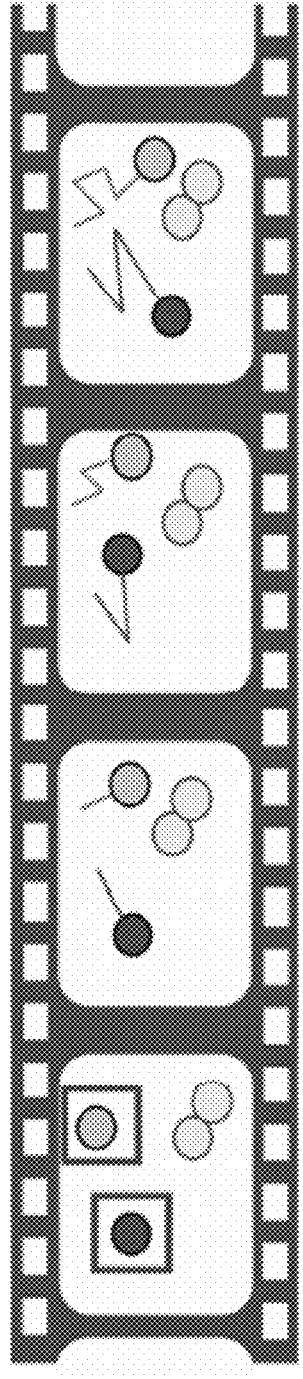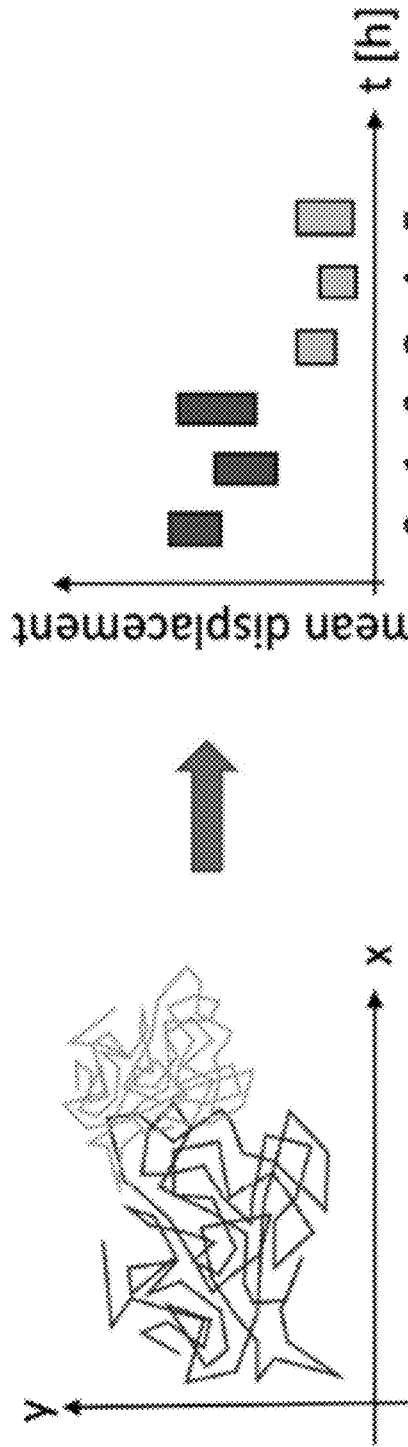
FIG. 1a
FIG. 1b
FIG. 1c
FIG. 1d
FIG. 1e

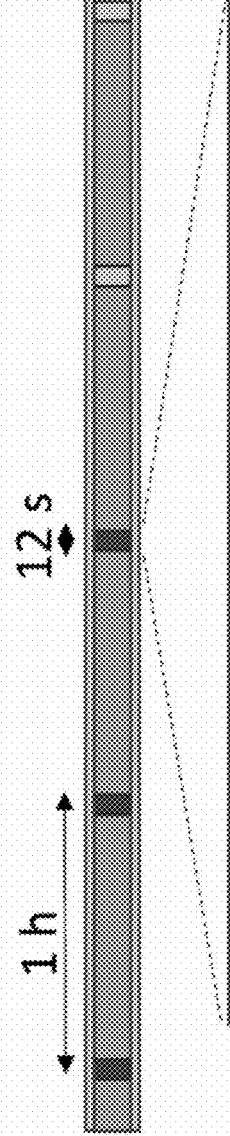
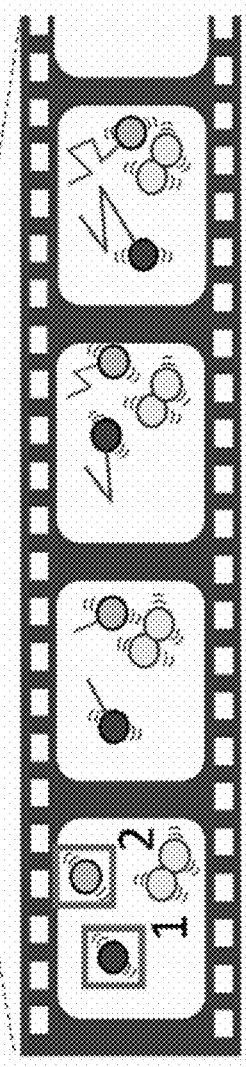
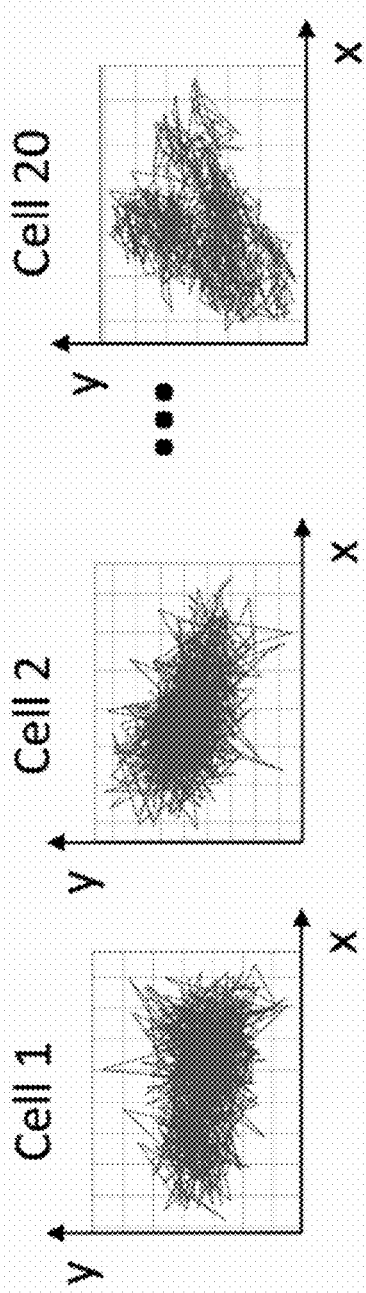
FIG. 13a
FIG. 13b
FIG. 13c

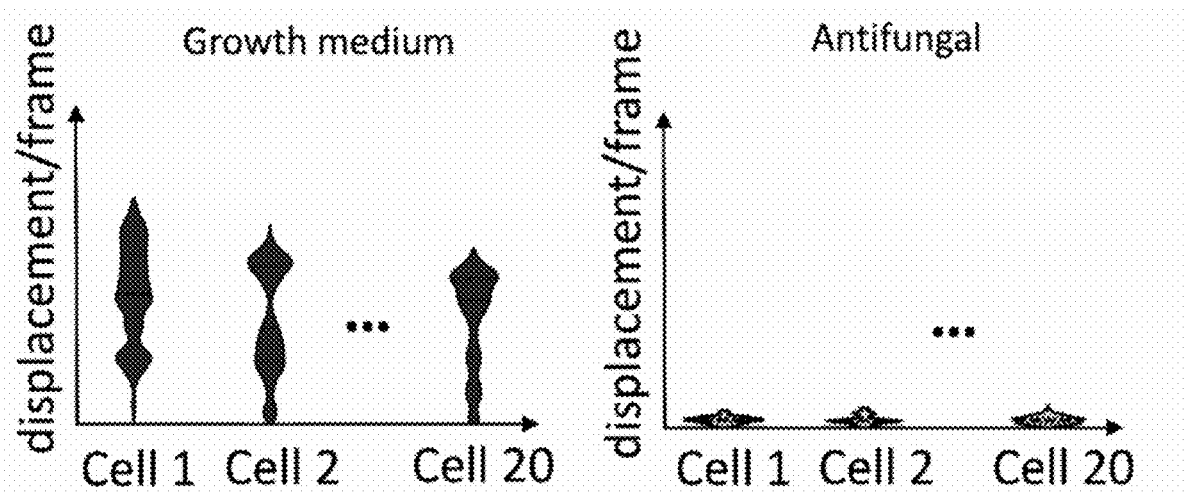
FIG. 13d
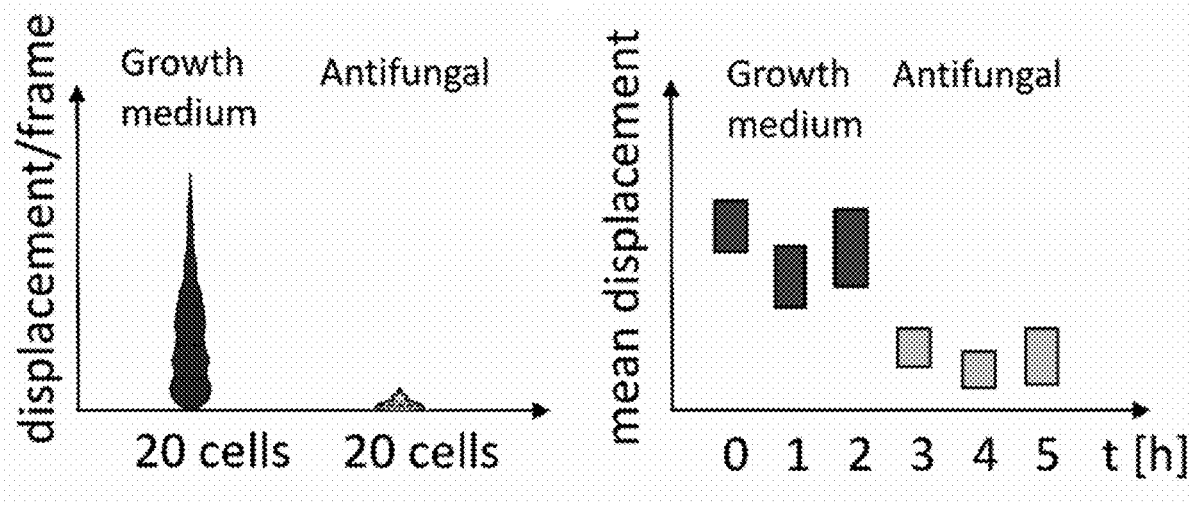
FIG. 13e  FIG. 13f

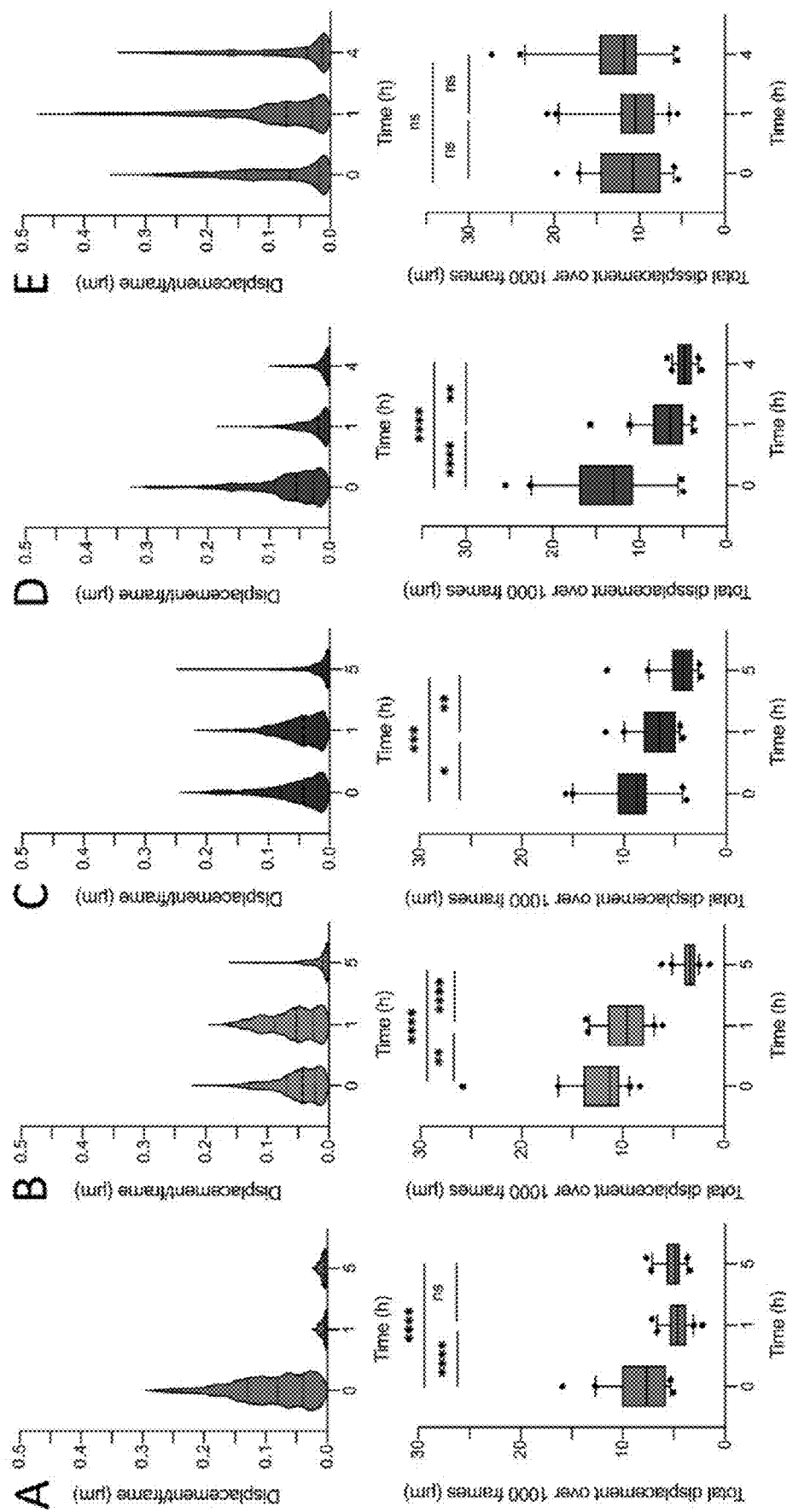
FIG. 16a-e

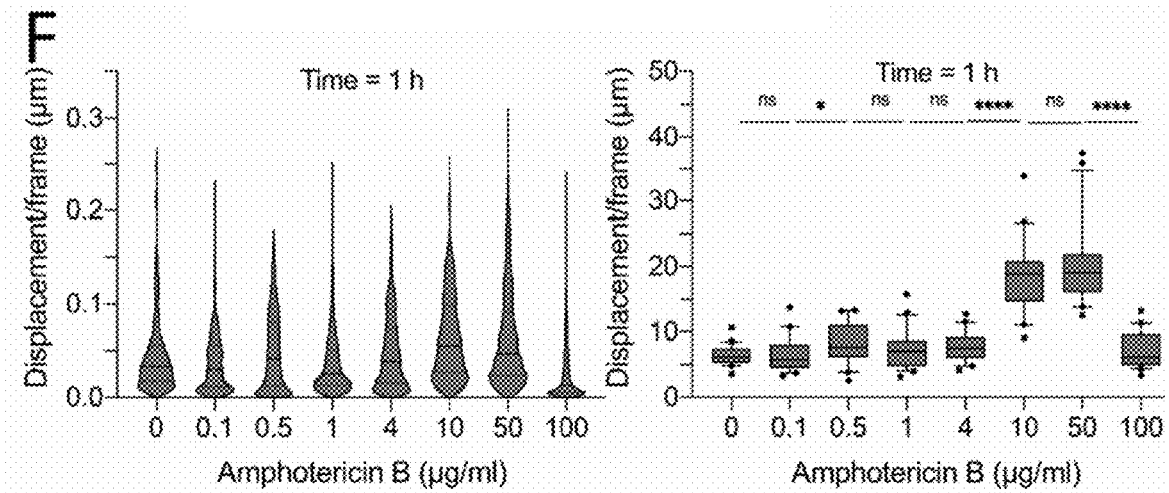
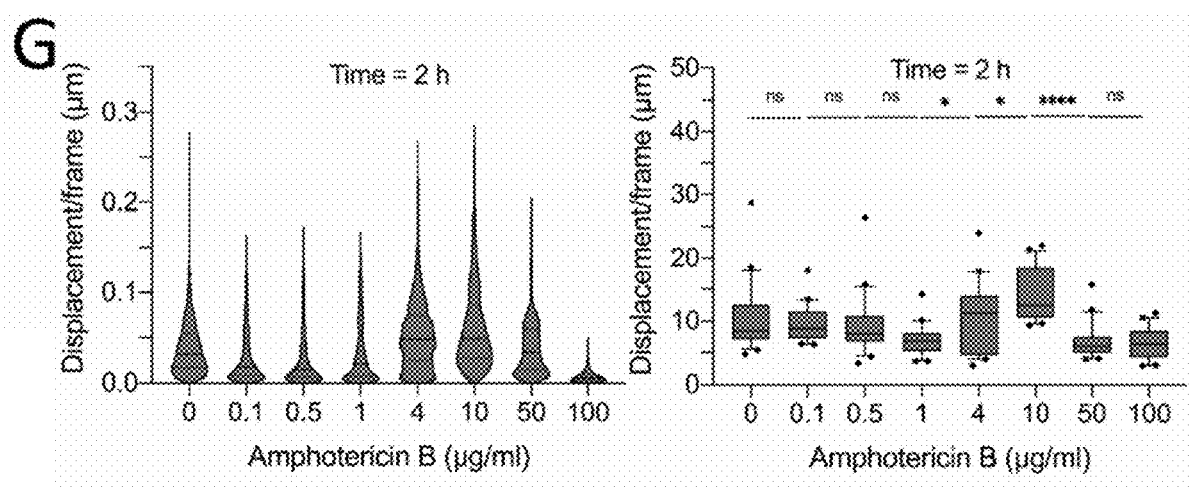
FIG. 16f-g

FIG. 17c-d
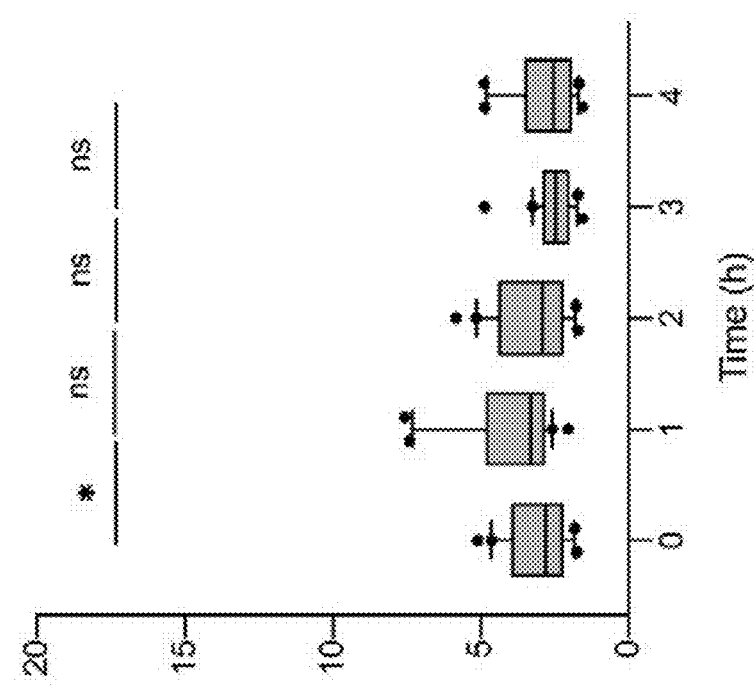
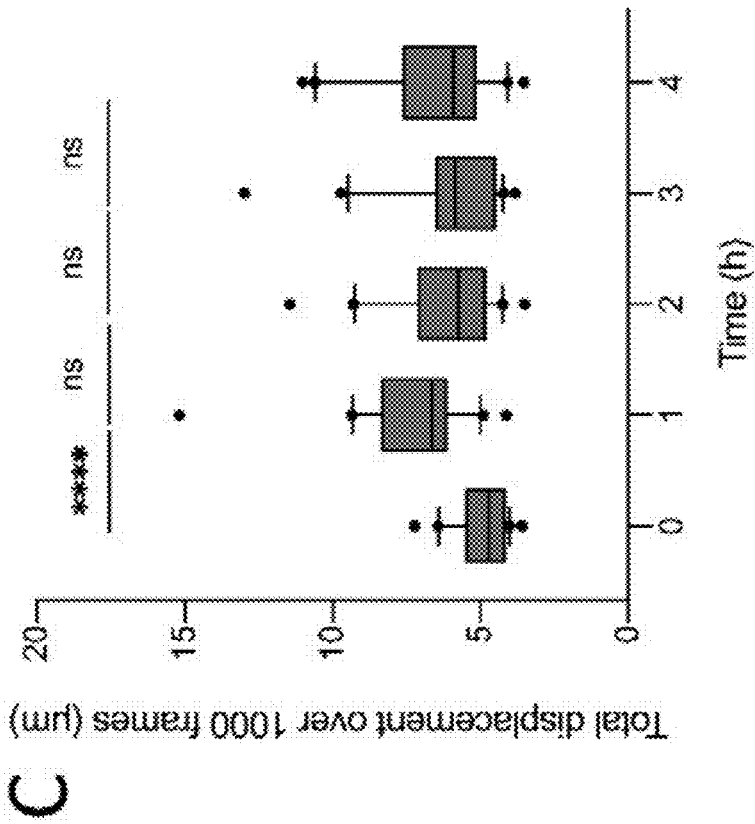

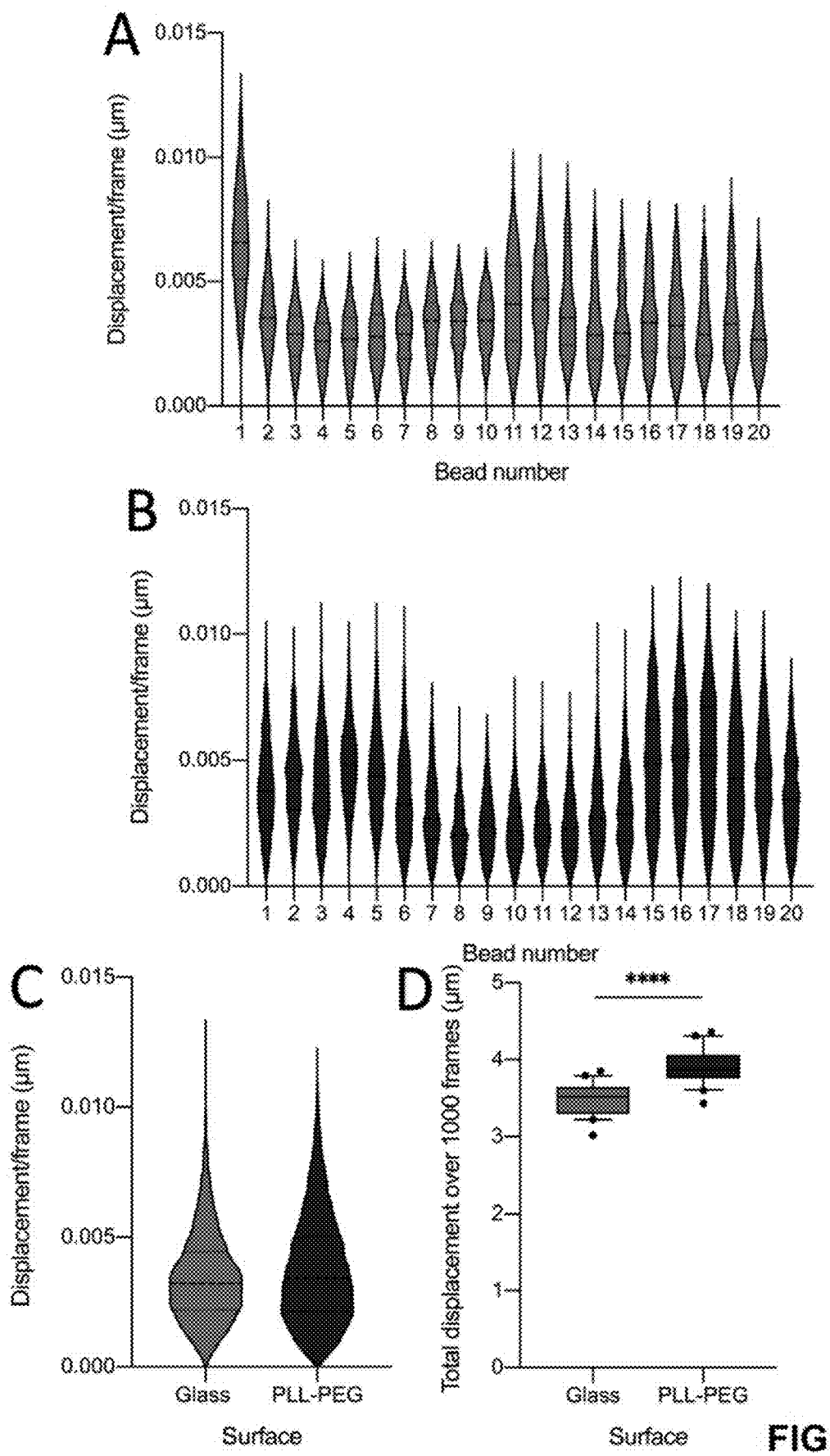
FIG. 18a-d

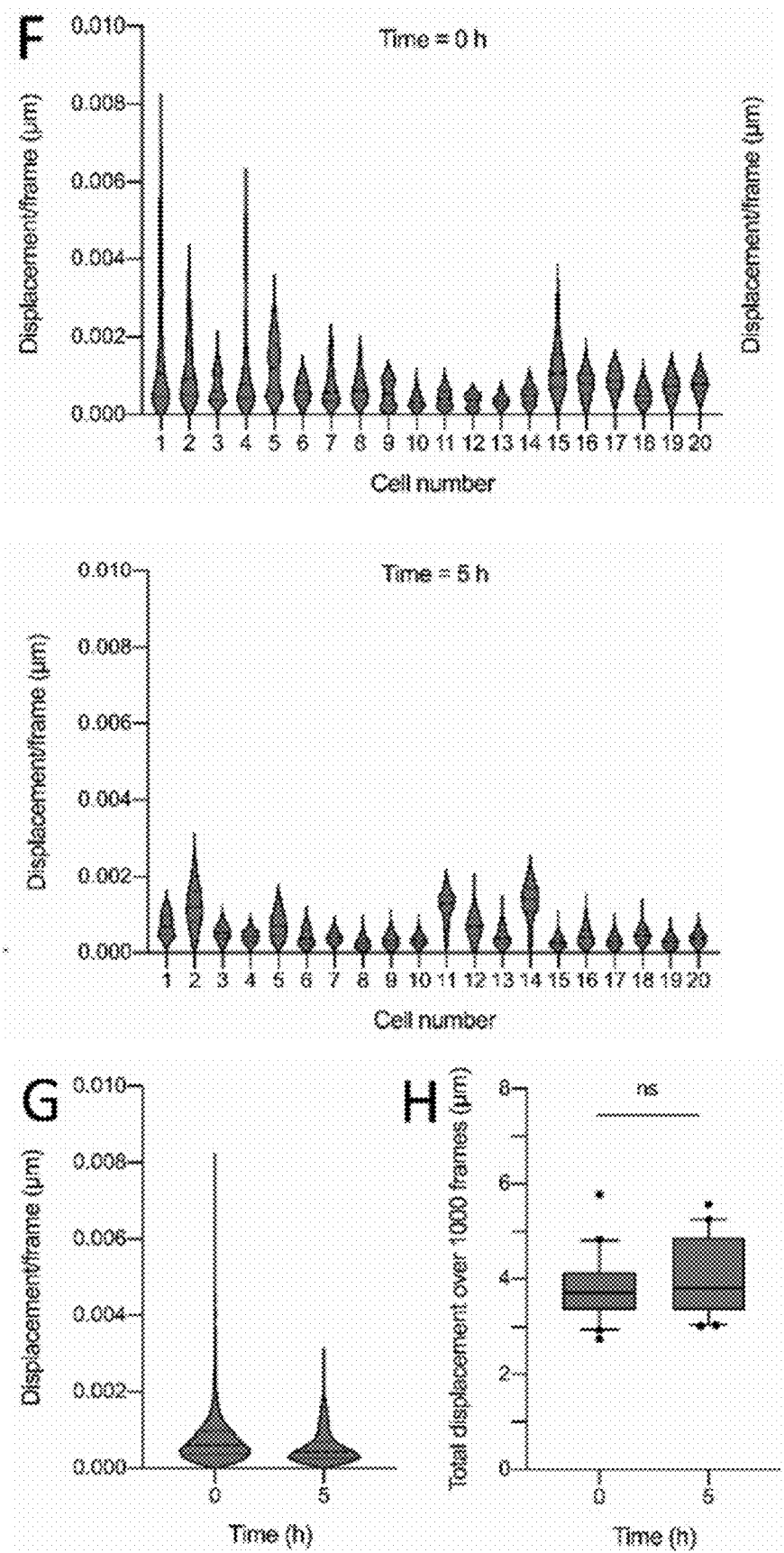
FIG. 18f-h

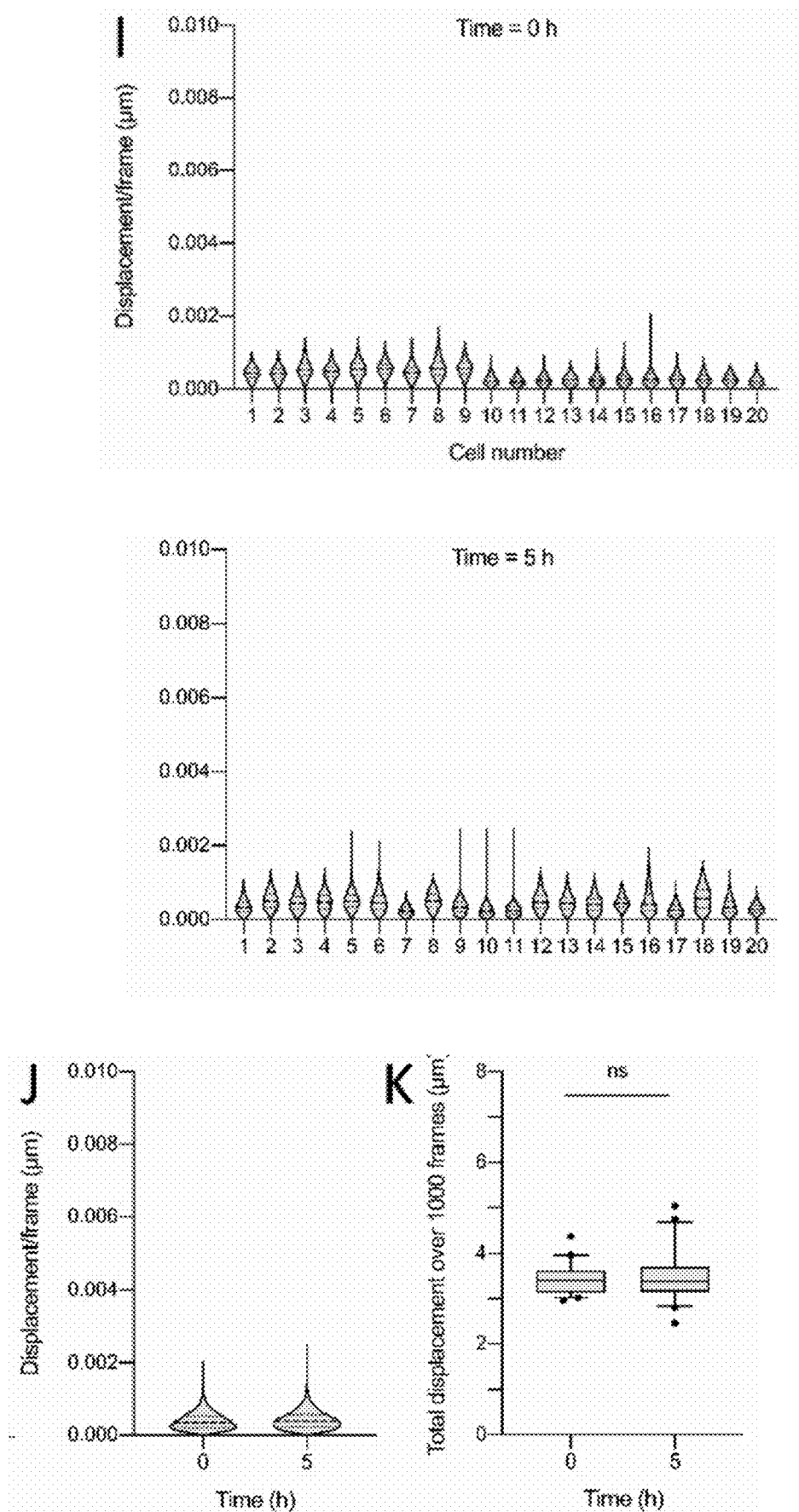
FIG. 18i-k

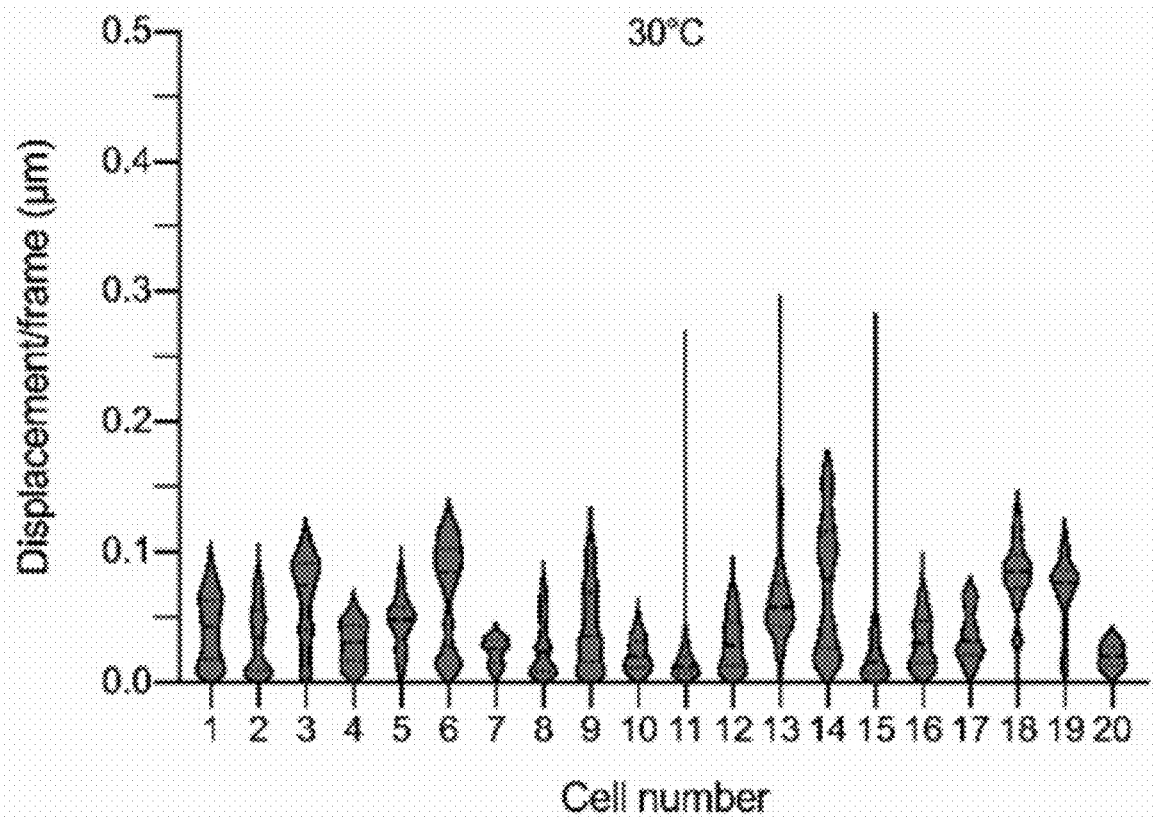
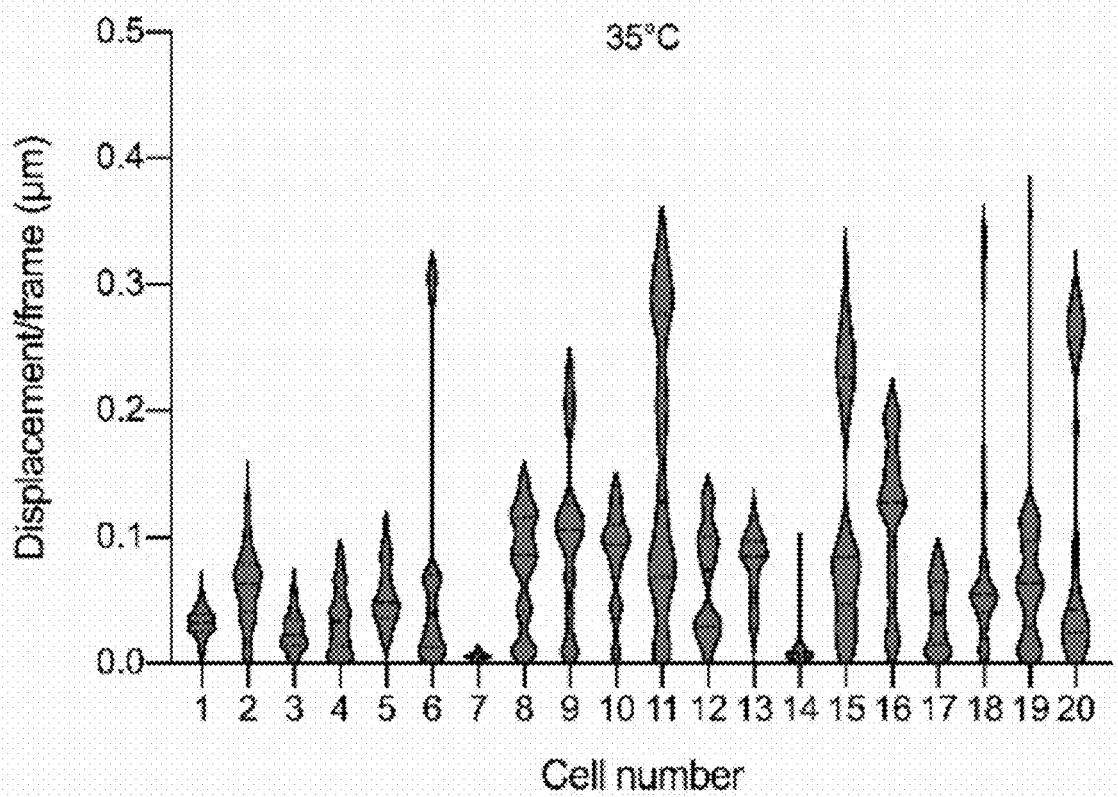
FIG. 19b

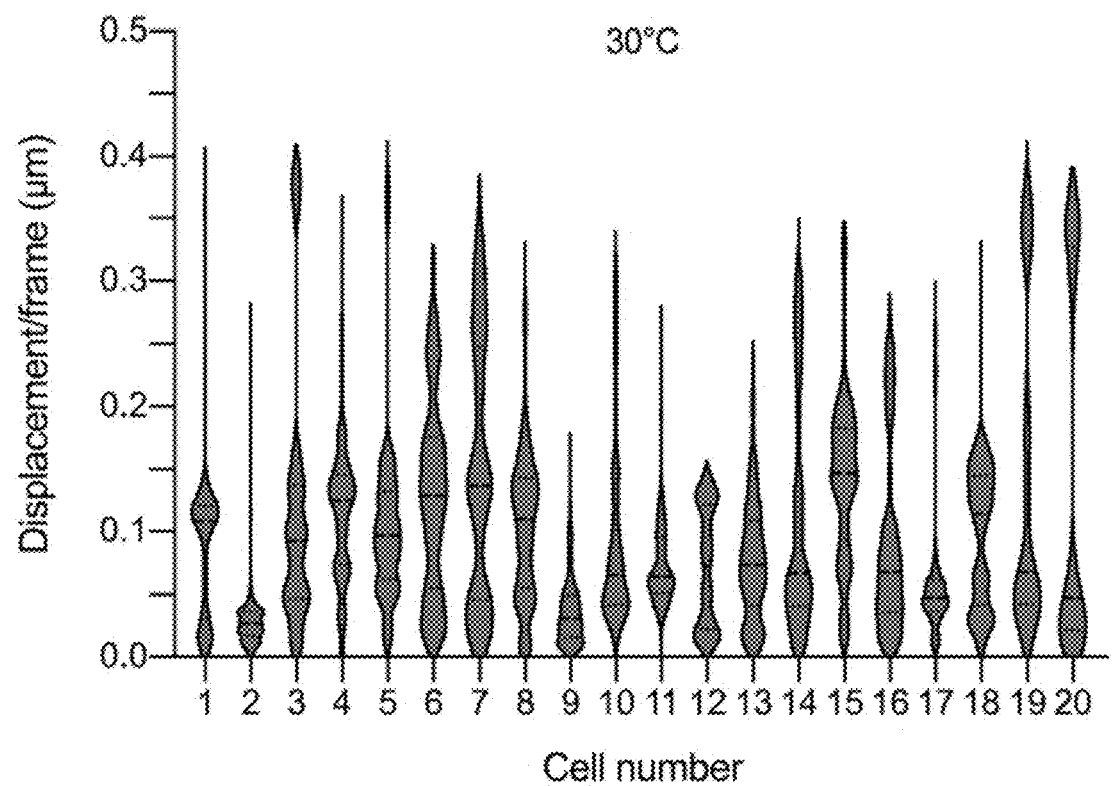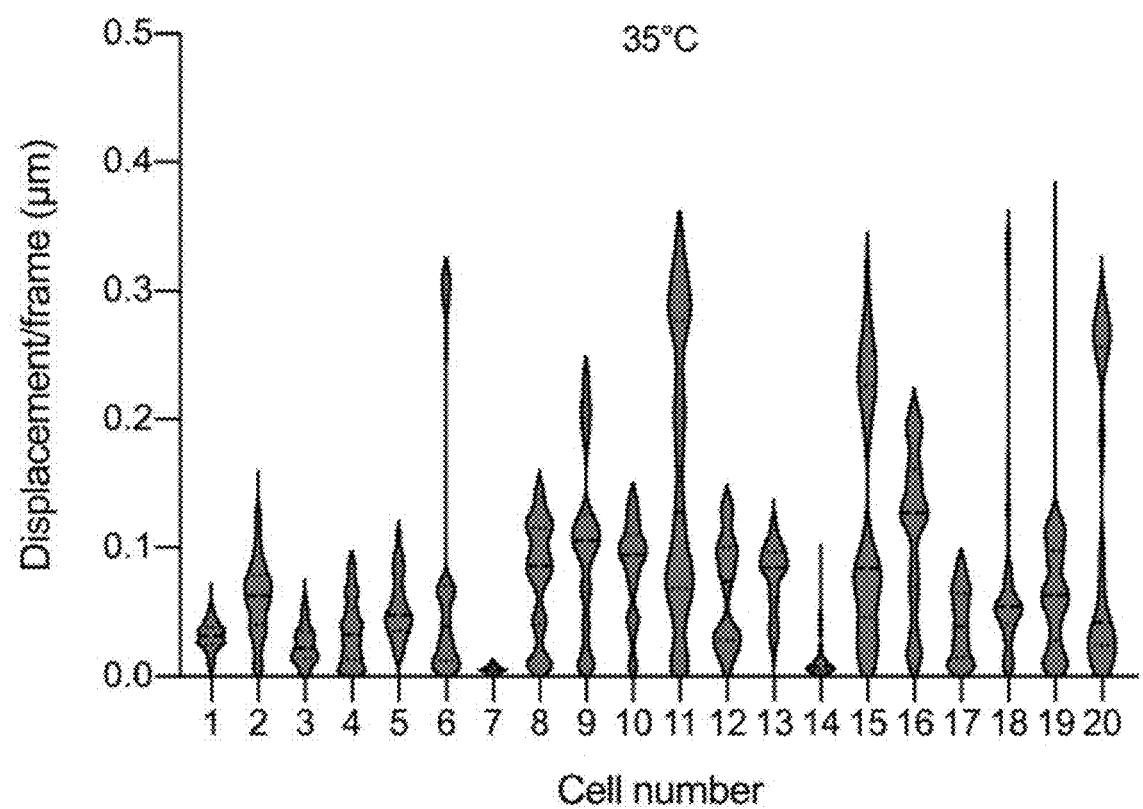
FIG. 19d

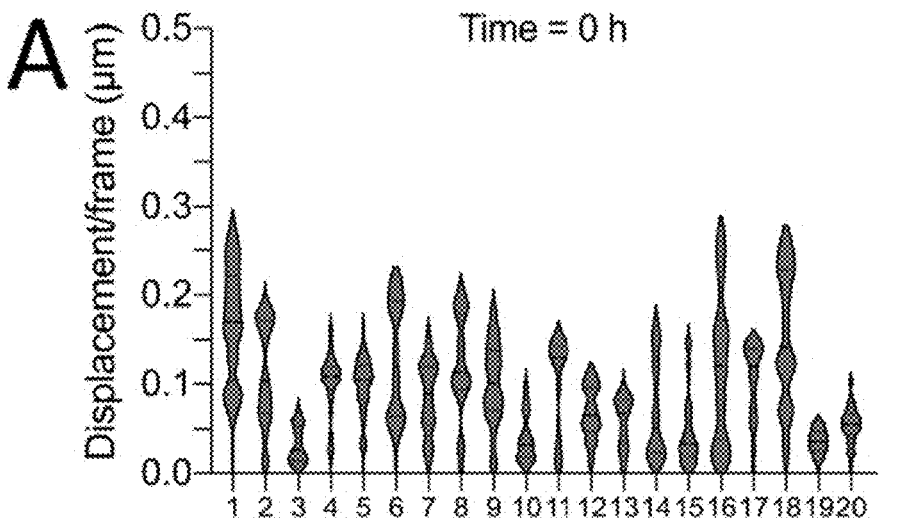
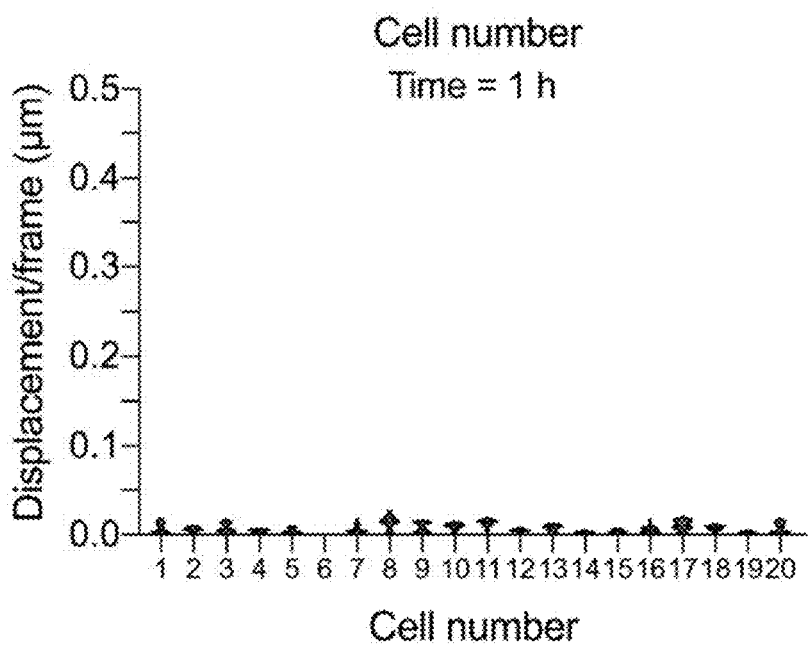
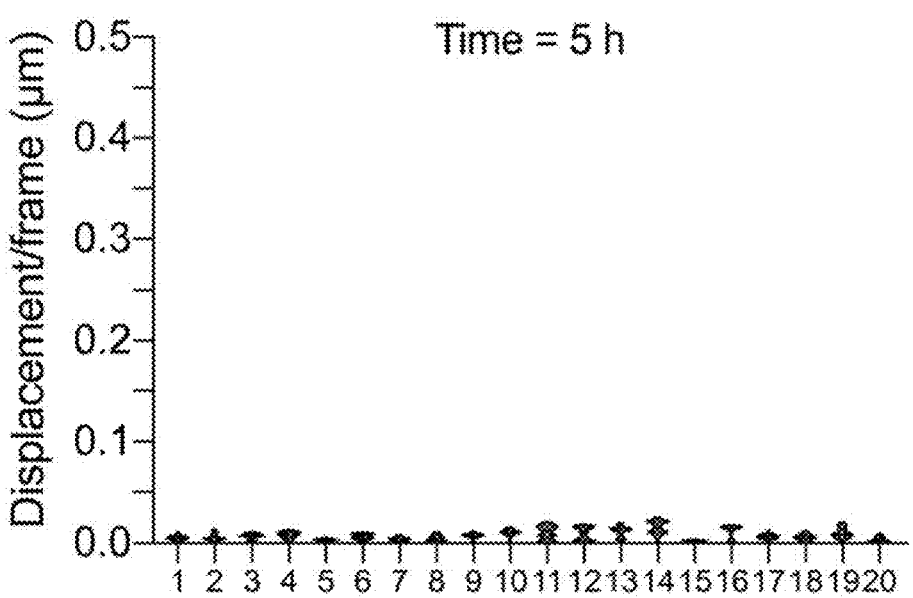
FIG. 20a

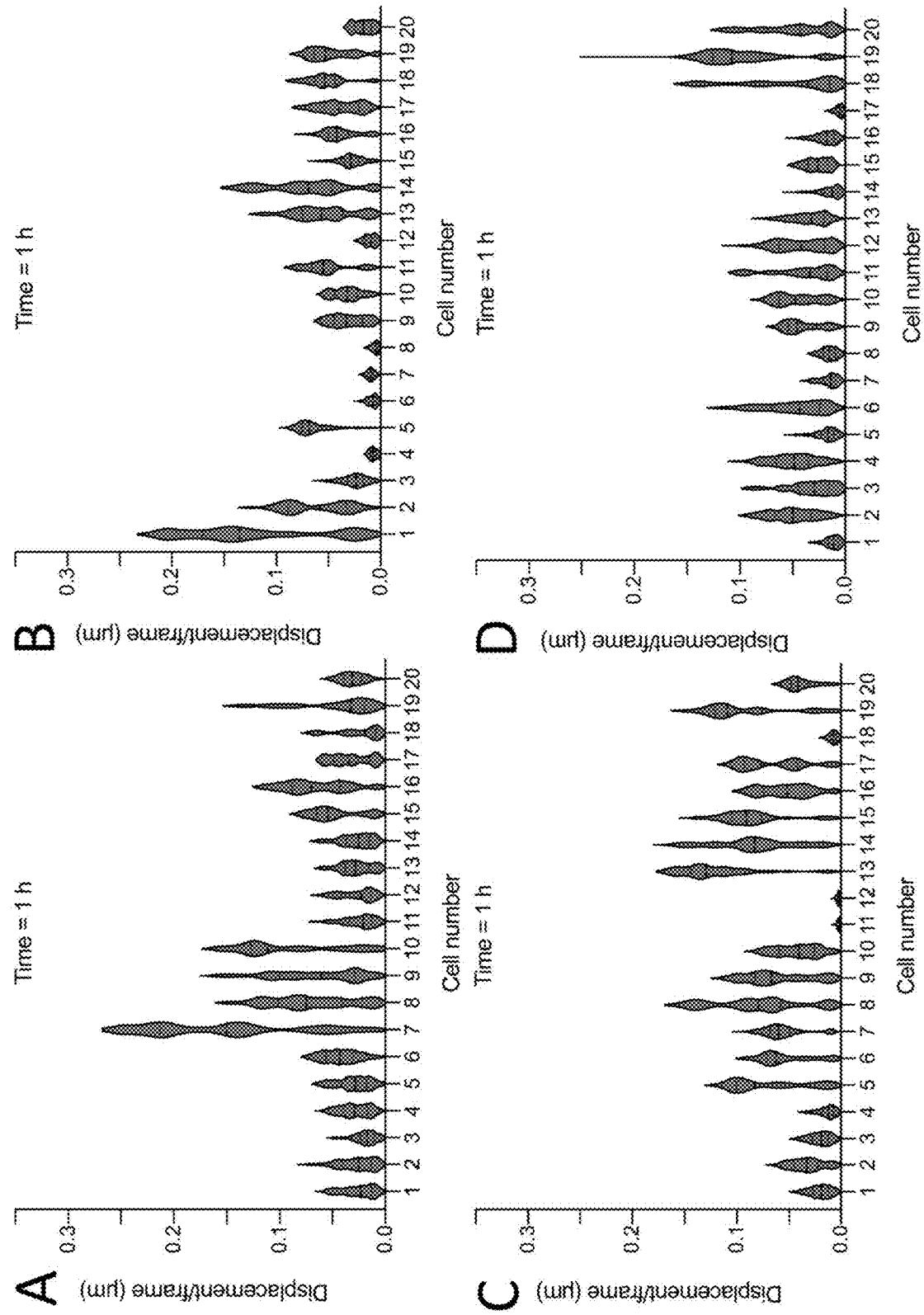
FIG. 21a-d

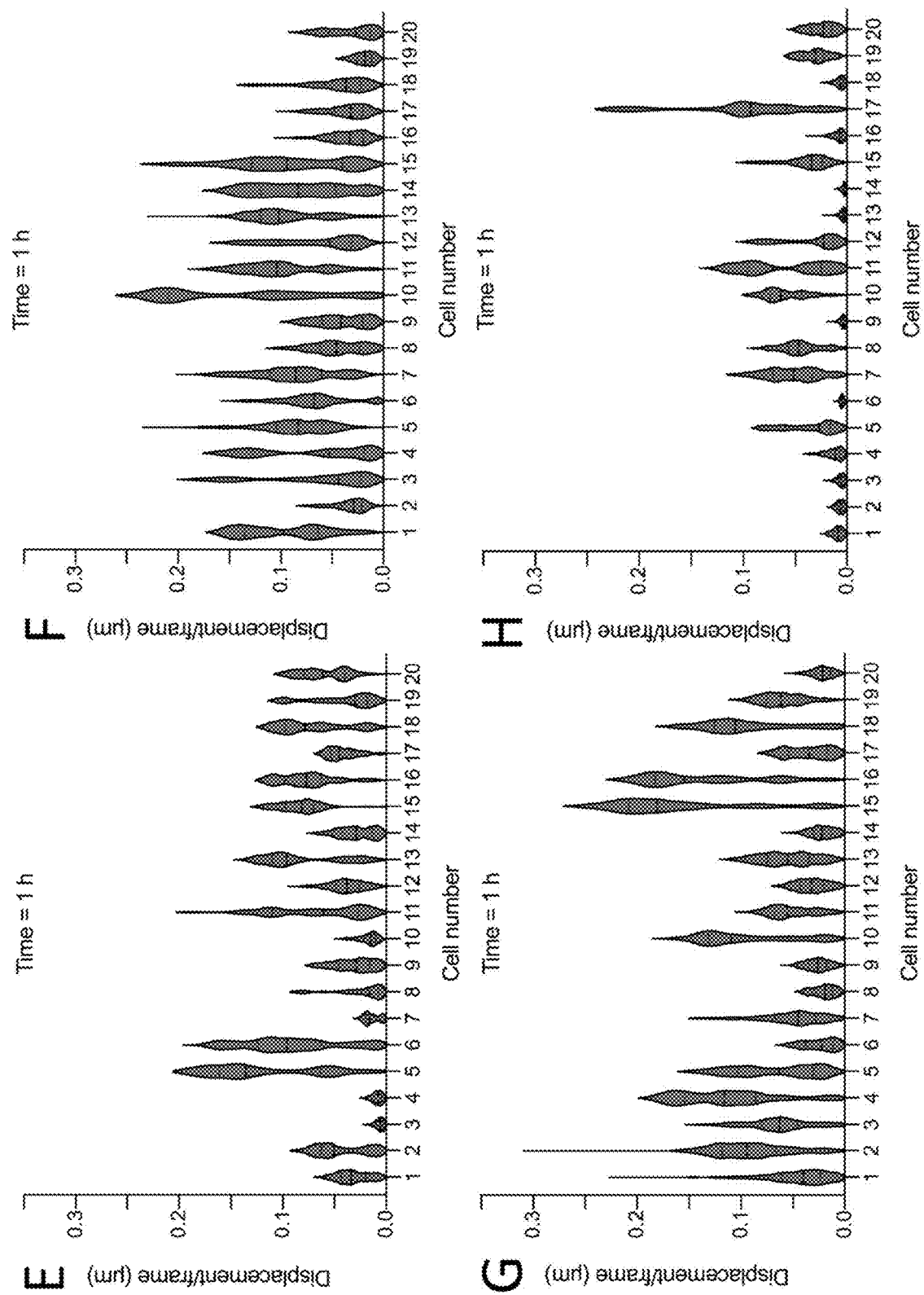
FIG. 21e-h

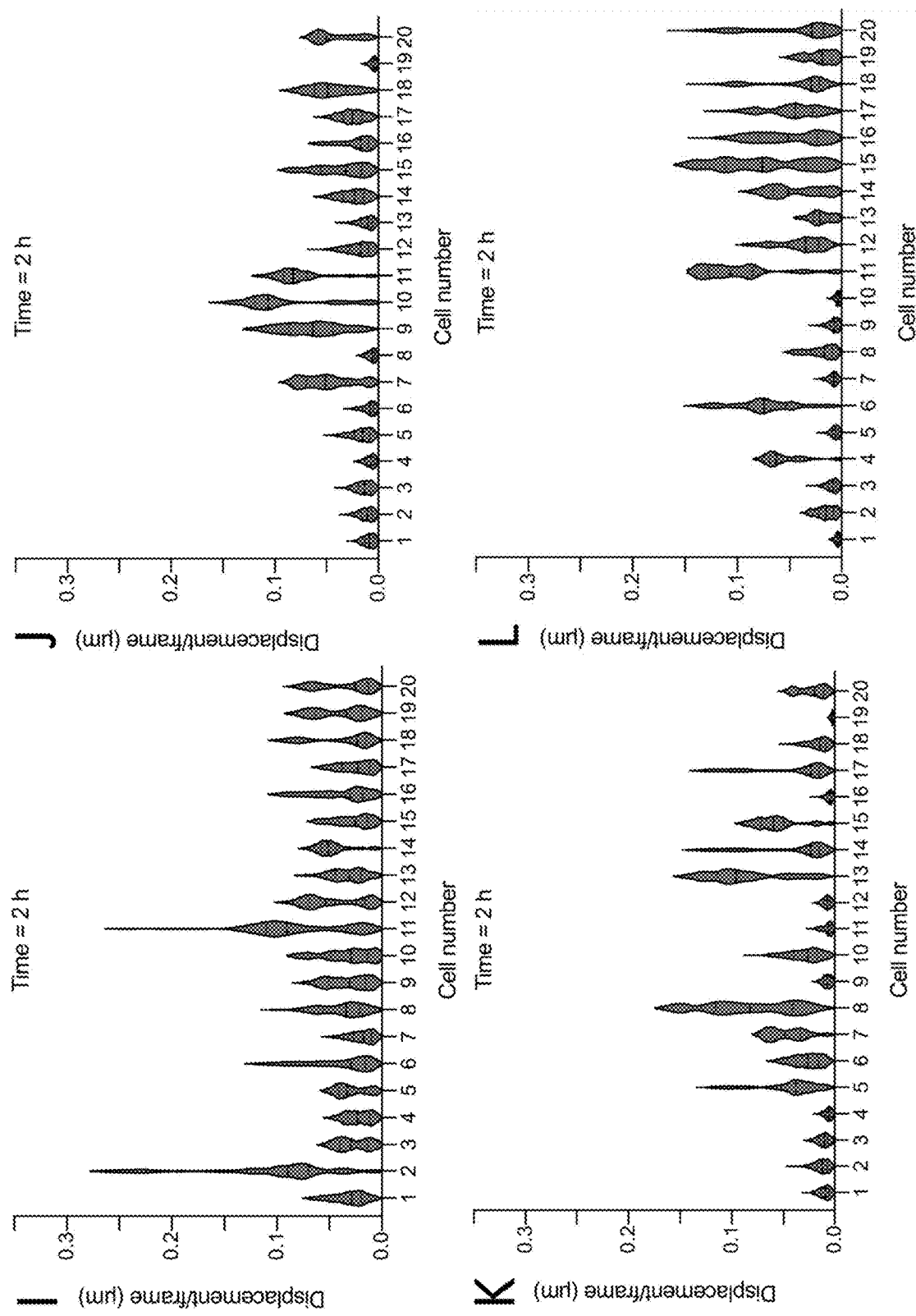
FIG. 21i-l

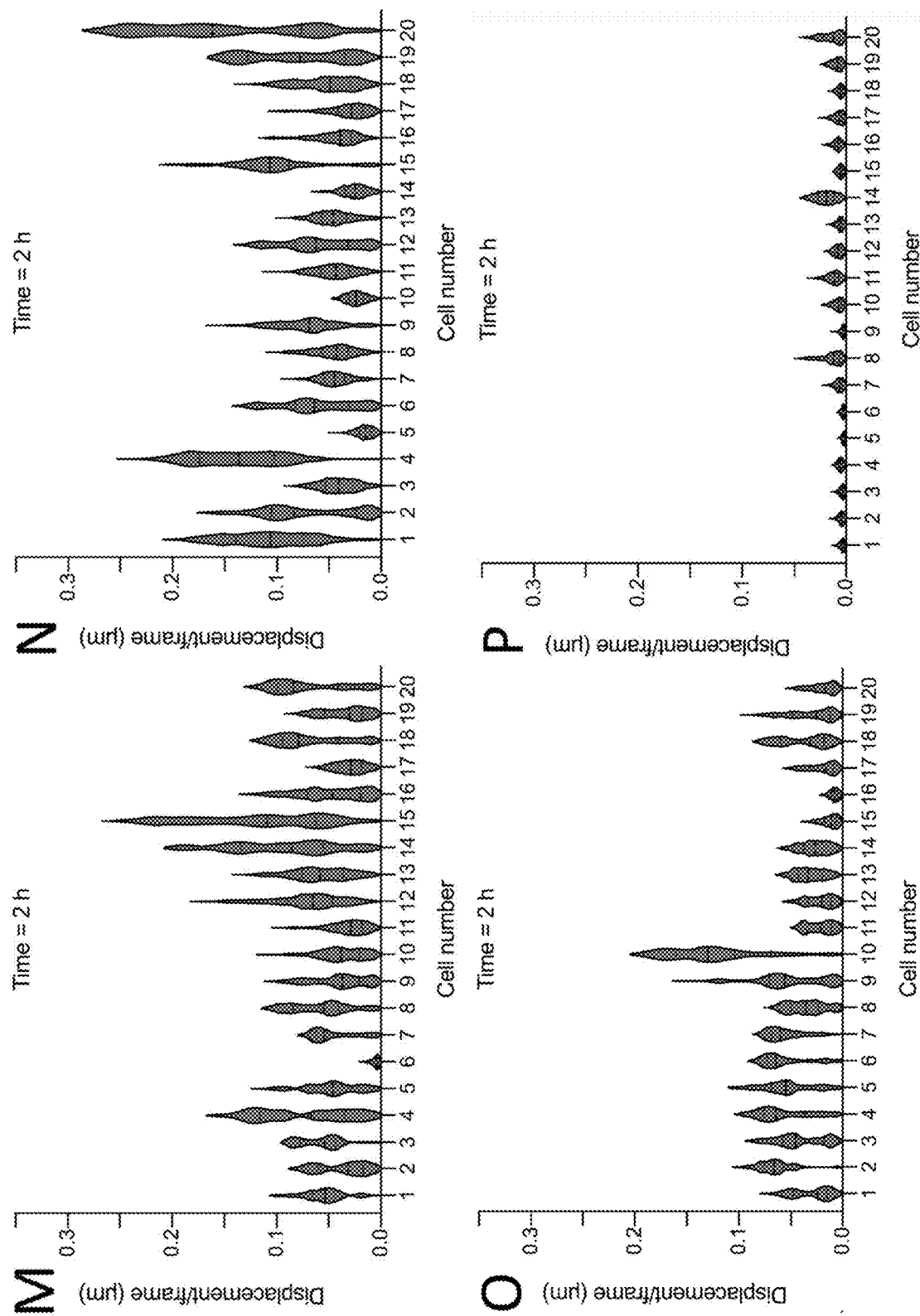
FIG. 21m-p

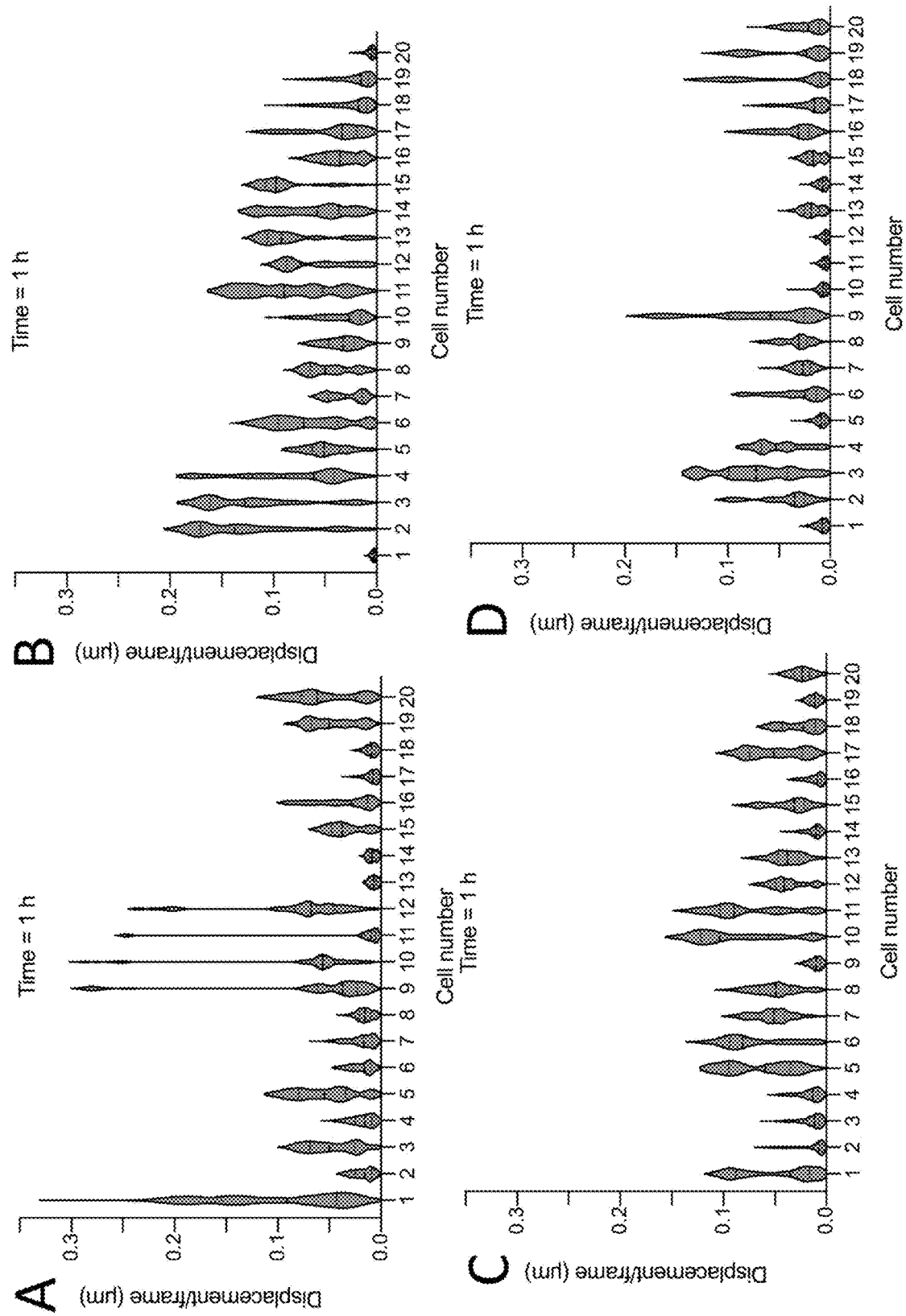
FIG. 22a-d

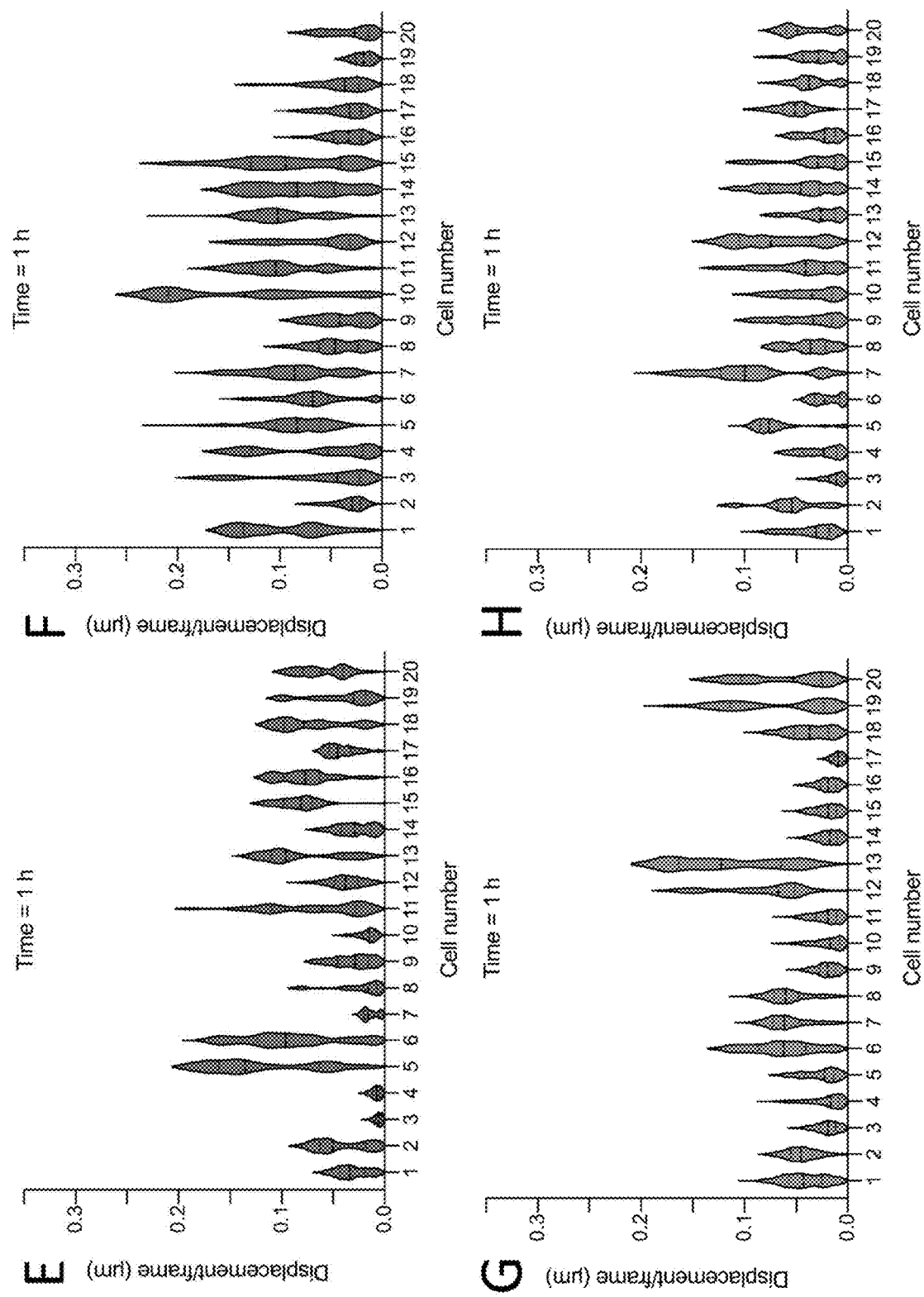
FIG. 22e-h

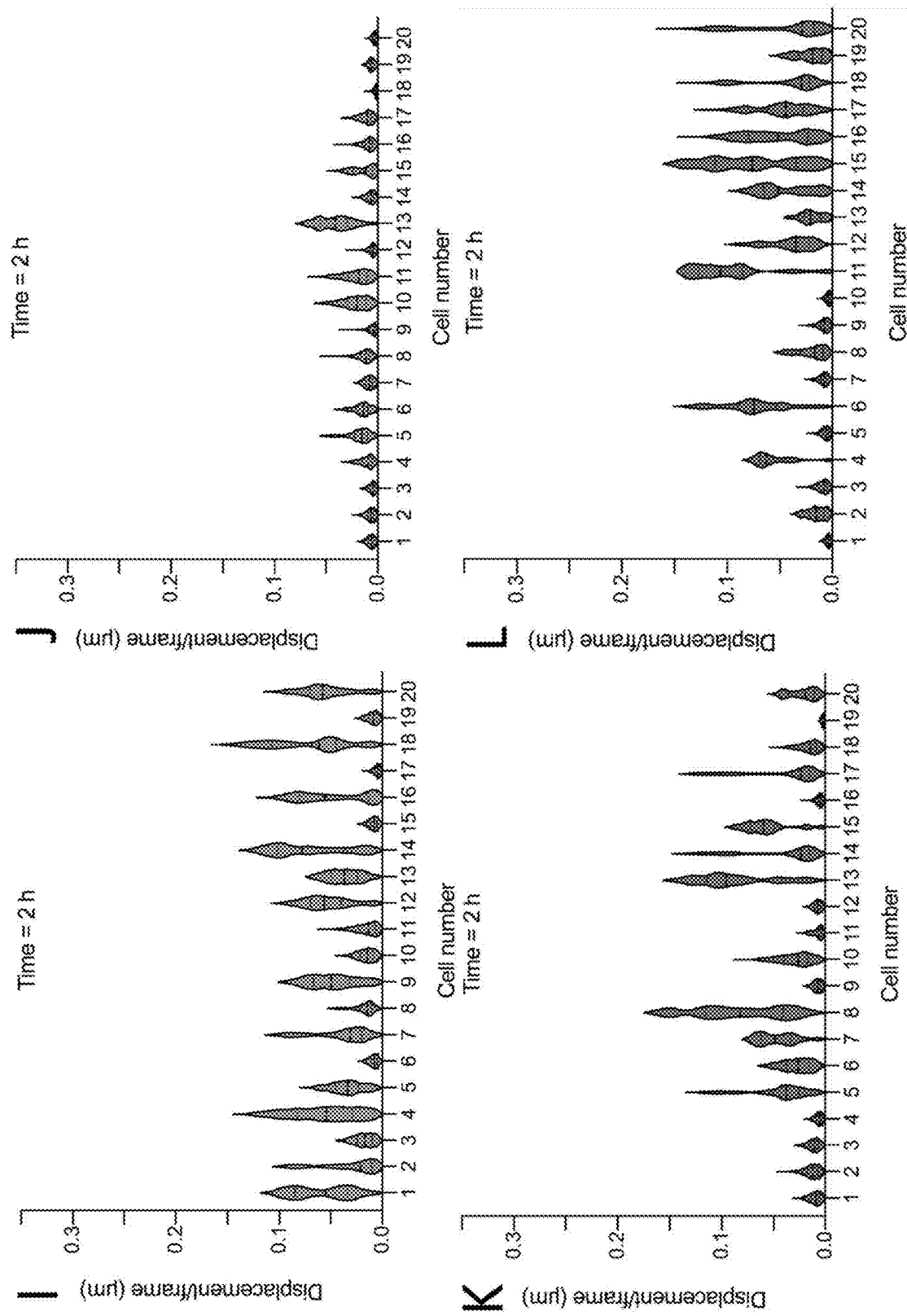
FIG. 22i-l

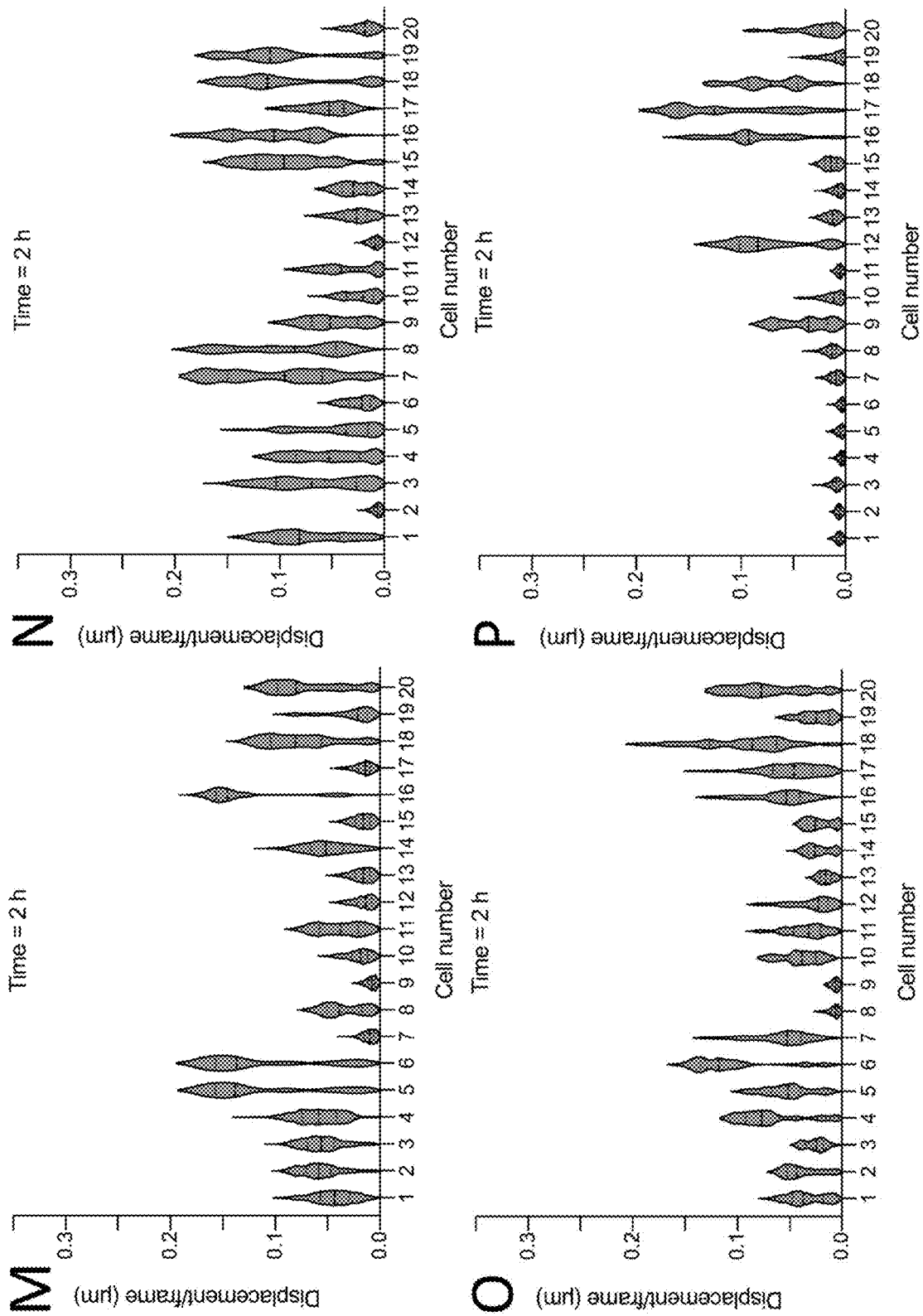
FIG. 22m-p

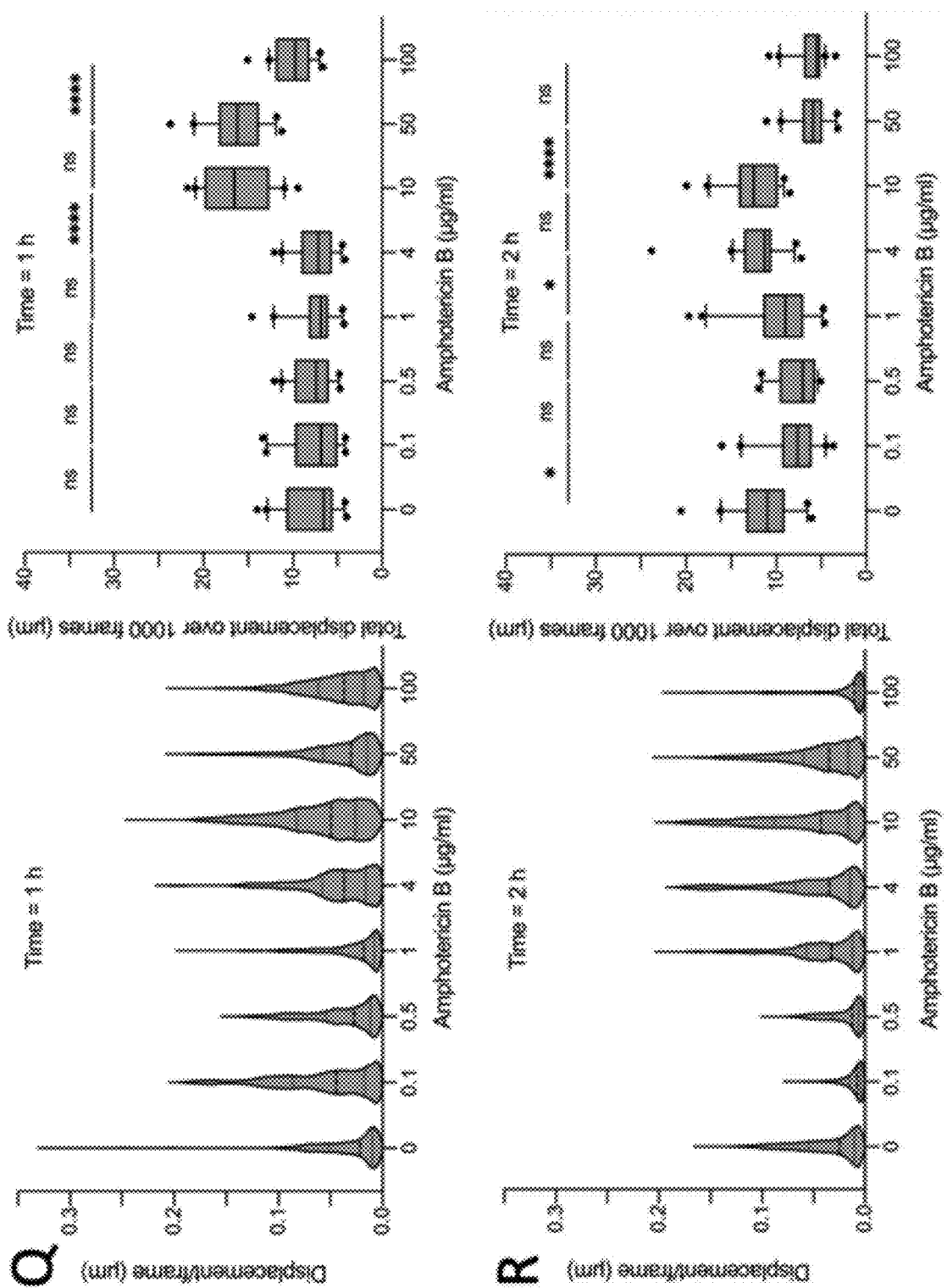
FIG. 22q-r

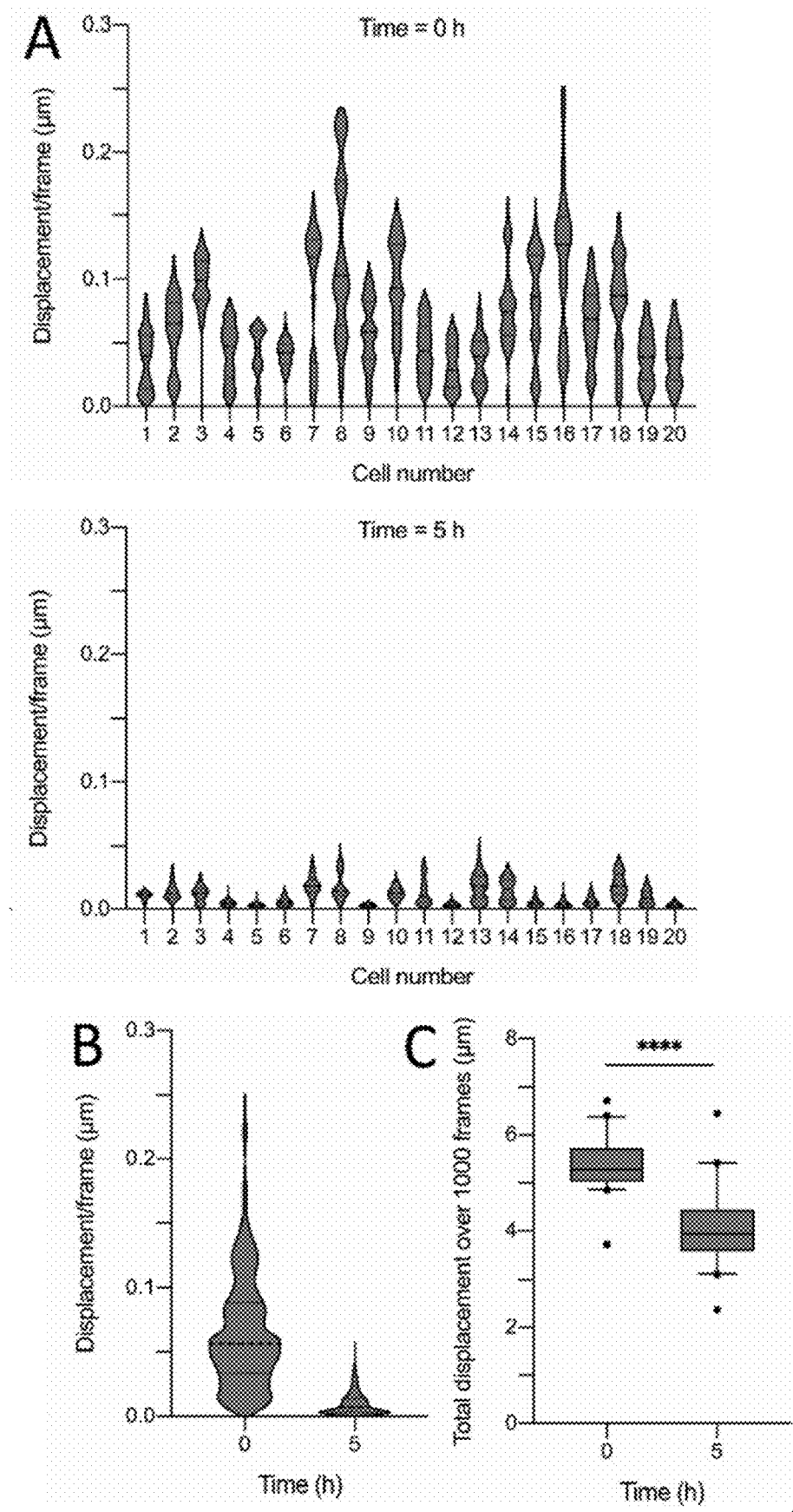
FIG. 23a-c

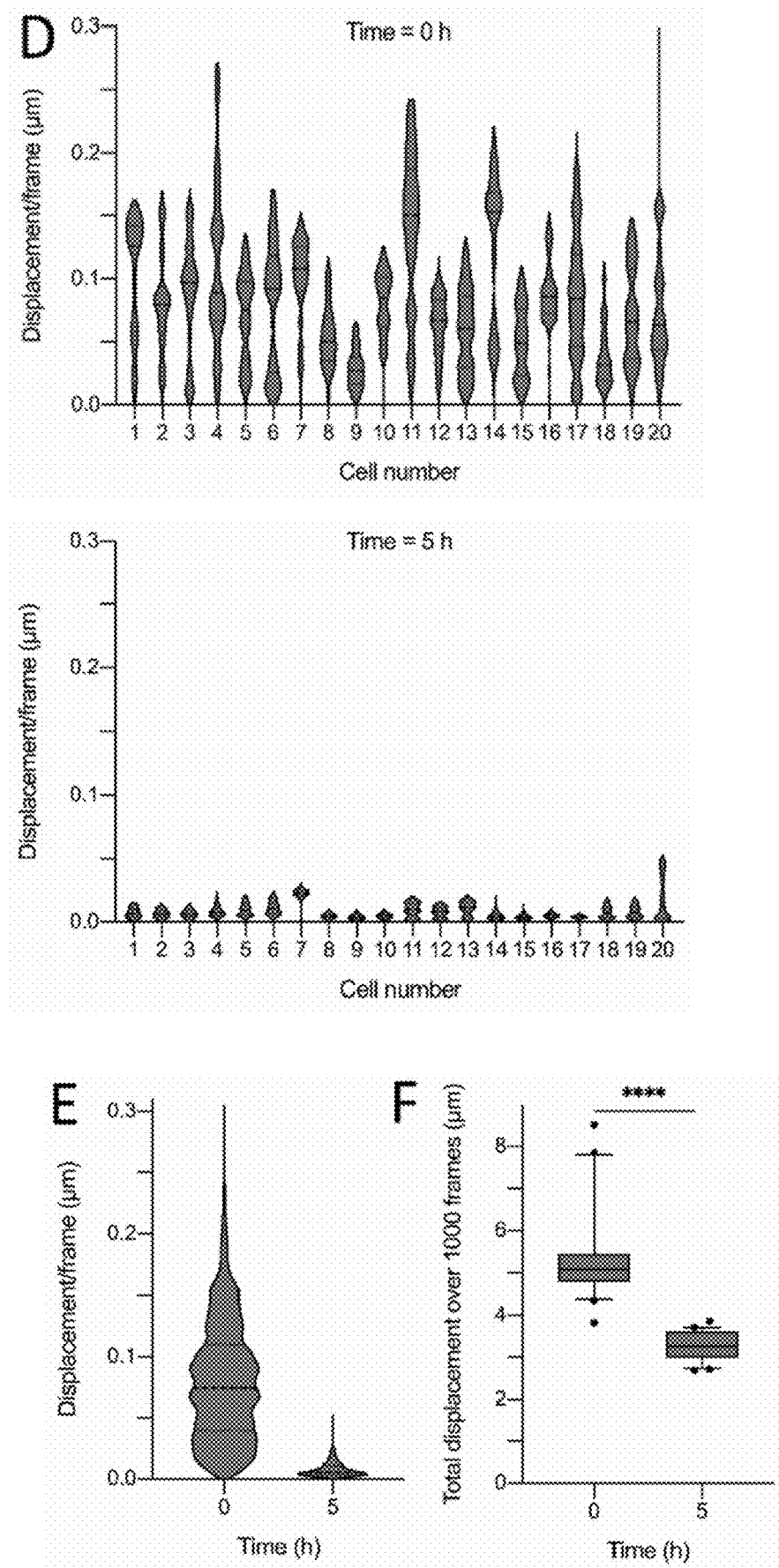
FIG. 23d-f

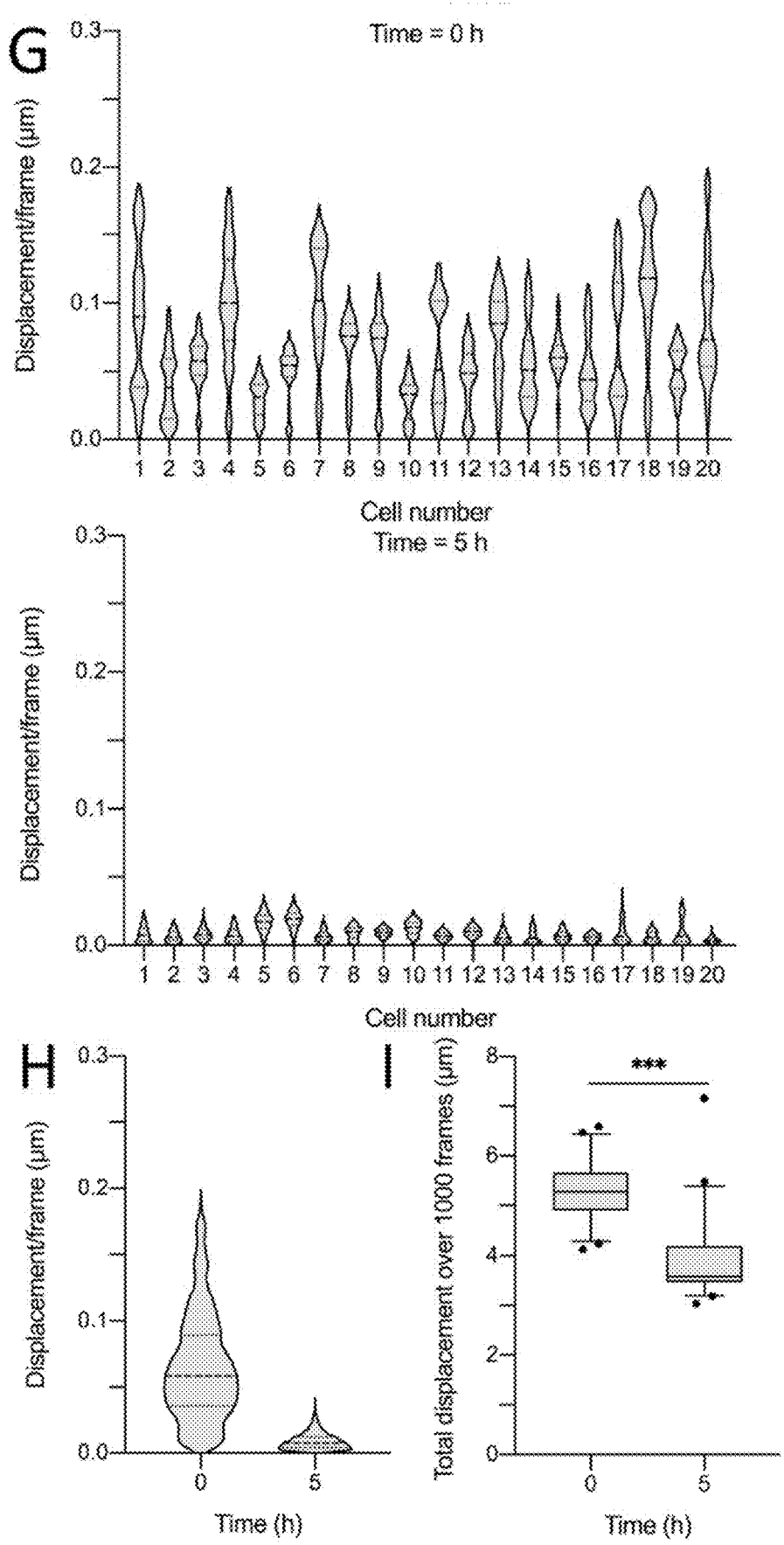
FIG. 23g-i

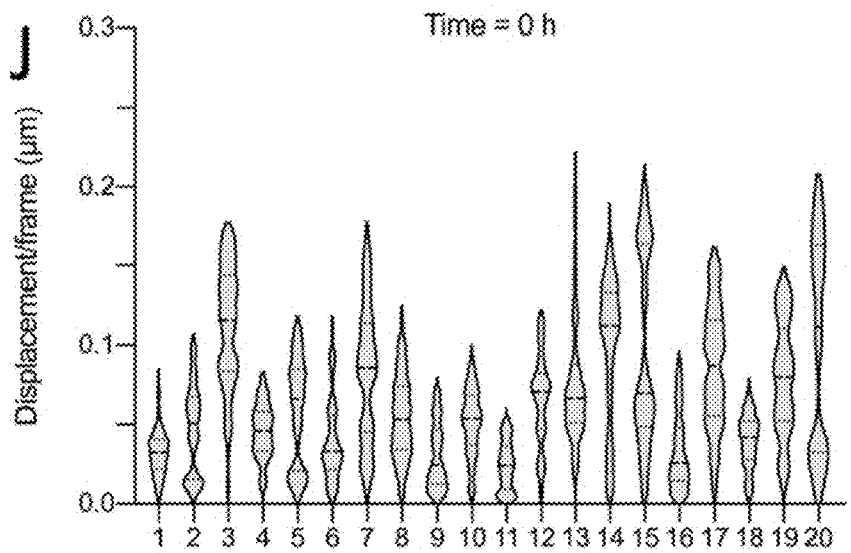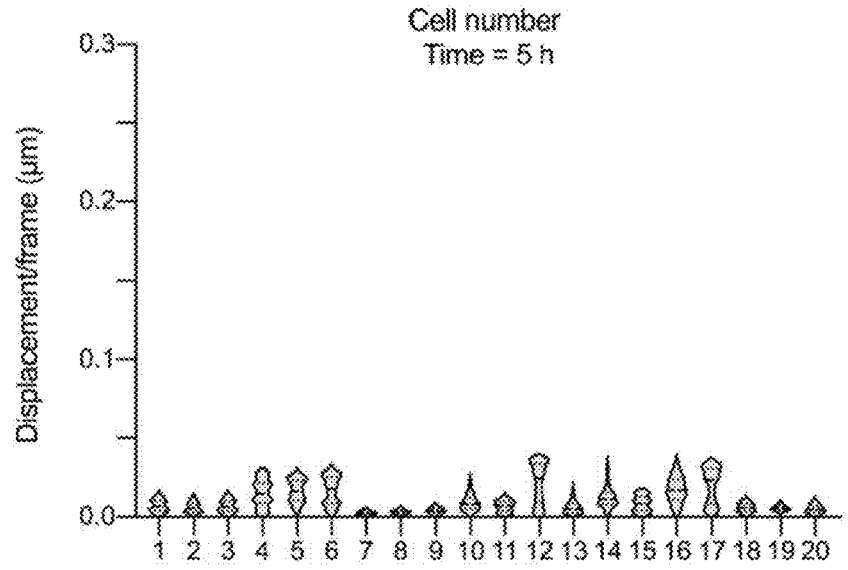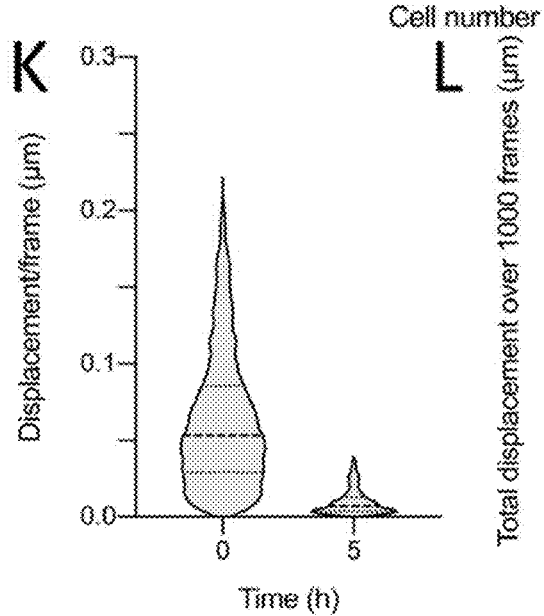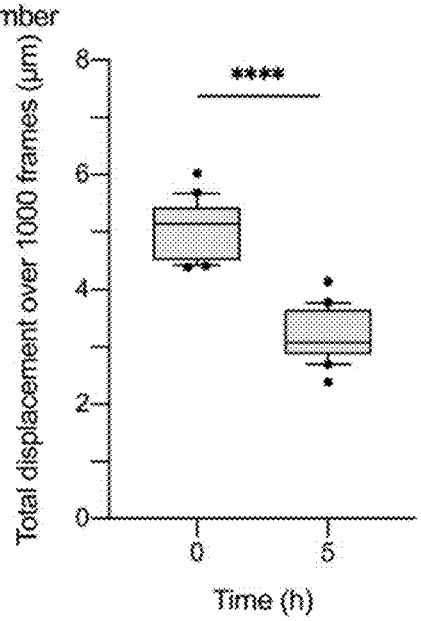
FIG. 23j-l

METHODS AND SYSTEMS FOR PARTICLE CHARACTERISATION BY IMAGING FREE-FLOATING PARTICLE MOVEMENT IN LIQUID ENVIORNMENT

TECHNICAL FIELD

The invention relates to the field of characterization of particles. More particularly, the present invention relates to characterization of particles such as living cells through optical nanomotion detection.

PRIOR ART

The wide and often uncontrolled use of large spectrum antimicrobial drugs at a worldwide scale promotes the emergence of resistant strains that constitutes one of the biggest threats to global health, food security and development. One of the options to rationalize the use of large spectrum antibiotics and antifungals consists in employing rapid sensitivity detection tests that identify the most appropriate drug to fight a given microorganism immediately at the admission of the patient in a medical centre. Such an early diagnostic should permit to immediately start the most appropriate treatment and avoid the use large spectrum drugs, documented to induce resistance. Standard antimicrobial susceptibility testing (AST) methods rely on measuring bacterial or fungal growth in the presence of antifungals during 24 to 48 h.

Several years ago, an atomic force microscopy (AFM)-based nanomechanical sensor to assess the effects of chemicals on the viablity of bacteria in a timeframe of minutes.

The detection is based on the observation that living organisms oscillate at a nanometric scale and transfer these oscillations to the AFM cantilever onto which they are attached. These oscillations last as long the organism is alive but stop as soon as the viability of the cells is compromised by any chemical or physical means.

These oscillations are present in living bacteria and their organelles, such as mitochondria and nuclei, yeasts, plant and mammalian cells. Antibiotic or antifungal sensitivity tests are carried on by attaching the microorganism onto the AFM cantilever and monitoring its oscillations as a function of different antimicrobial drugs. Recently, other nanomotion methods for antimicrobial susceptibility testing (AST) have been developed. These are based on plasmonic imaging of the z-motion of bacteria, tracking the submicron scale x y motion of attached bacteria, sensing the vibrations of attached bacterial with phase noise of a resonant crystal, and Sub-Cellular Fluctuation Imaging (based on Total Internal Reflection microscopy) on attached bacteria. These nanomotion methods can accomplish full antibiotic sensitivity tests in a timeframe of minutes to hours, whereas the traditional cell culture-based technique requires days or weeks in case of slowly growing organisms. However, all these methods possess several drawbacks, including the most challenging one is being the attachment of the organism of interest onto a surface.

SUMMARY OF THE INVENTION

It is an object of embodiments of the present invention to provide good methods and systems for characterizing particles, such as for example cells.

It is an advantage of embodiments of the present invention that the characterisation of the particles can provide information regarding the viability and/or metabolic activity of the particles.

It is an advantage of embodiments of the present invention that the methods and systems are applicable to a variety of particles, such as for example living cells. The characterisation may in some embodiments for example be used in biotechnological applications, clinical microbiology, antibiotic/antifungal susceptibility testing, characterization of cell viability, metabolism monitoring, diagnostics and drug screening and fundamental research.

It is an advantage of embodiments of the present invention that characterisation of particles, e.g. cells, can be performed in a high-throughput approach.

It is an advantage of embodiments of the present invention that there is no need for labelling of particles in order to characterise them.

It is an advantage of embodiments of the present invention that characterisation of particles, e.g. cells, can be performed without the need for attaching them to a surface. e.g. a surface of a mechanical object or the surface of a larger particle.

It is an advantage of embodiments of the present invention that the systems and methods are growth independent as well as independent of the speed of cells' replication/division so that duration of the measurement can be short.

It is an advantage of embodiments of the present invention that characterisation of particles can be performed with relative simple measurement systems.

It is an advantage of embodiments of the present invention that characterisation of particles can be performed without the need for the particles to be connected to a surface. The latter results in the fact that no linker molecule is required for linking the particle to a surface. This avoids the problem that occurs for some particles in linking them with known linker molecules or avoids the problem that occurs in that some linker molecules have a negative effect on the particles.

It is an advantage of embodiments of the present invention that characterisation and/or analysis of cells can be performed in an automated way and/or automatically.

It is an advantage of embodiments of the present invention that methods and systems can be applied for characterising particles in a plurality of ways, e.g. In microwells such as for example in microwell plates, or in droplet microfluidics.

It is an advantage of embodiments of the present invention that methods and systems can be applied for characterising a plurality of particles as well as for characterising individual particles.

It is an advantage of embodiments of the present invention that the methods and systems can be used for characterising a plurality of particles, e.g. a plurality of cells. In one embodiment, the methods and systems may be used for performing single-cell cancer cell screening. In one embodiment, the methods and systems can for example be applied to bacterial cells or yeast cells, vegetal cells and organelles e.g. such as mitochondria and nucleus. In one embodiment, the methods and systems can for example be applied to animal cells such as cancer cells.

It is an advantage of embodiments of the present invention that the response to chemotherapy drugs for cancer cells or tumour cells can be performed. It is an advantage of embodiments of the present invention that the methods and systems can be applied for performing a screening, e.g. for testing which drugs can kill most or all of the cancer cells in a tumour.

It is an advantage of embodiments of the present invention that methods and systems can be applied for determining a doses-response curve and/or for determining a minimal inhibitory concentration (MIC) and/or for determining a minimum fungicidal concentration (MFC) and/or for determining a minimum bactericidal concentration (MBC).

It is an advantage of embodiments of the present invention that methods and system can be applied for determining resistance to or effectiveness of pesticides on plant cells.

The method thus may in a particular embodiment be used for determining the specific antibiotics/antifungal to be used in order to treat a particular infection caused by bacteria or fungi or to determine antimicrobial resistance profiles of microbial isolates and to guide antimicrobial treatment decisions.

It is an advantage of embodiments of the present invention that the transportation time of samples and the time for testing can be significantly reduced, so that delays in the time to diagnosis of resistant pathogens and decisions for appropriate and effective antimicrobial therapy can be avoided. This can result in a decrease of patient mortality, better clinical outcomes, less use of broad-spectrum antimicrobials and correspondingly a reduction of resistance against antimicrobials.

It is an advantage of embodiments of the present invention that rapid antimicrobial susceptibility testing can be performed, that personalized therapies (using narrow-spectrum antimicrobial administration) can be used and that treatment can be given in the earliest possible treatment stage.

It is an advantage of embodiments of the present invention that it works with motile and non-motile cells.

In one aspect, the present invention can relate to a method for deriving particle characteristics, the method comprising
  imaging the movement of at least one free-floating particle in a liquid environment at at least one moment in time,
  determining for at least one moment in time at least one movement parameter based on the imaged movement of the free-floating particles in the liquid environment, and
  deriving from the at least one movement parameter a characteristic of the at least one particle.

It should be noted that the method can comprise the derivation of a single characteristic of a single particle, the derivation of two or more characteristics of a single particle, the derivation of a single characteristic of two or more particles, or the derivation of two or more characteristics of two or more particles.

Hence, said at least one particle may comprise a plurality of particles. The present method thus gives insight into the characteristics of one particle but also of a group of particles. For example, the method can be used for determining the characteristic of one or more particle compared to the characteristics of other one or more particles of a plurality of particles. For instance, the present method can be used for determining which cells of a cell population or group are resistant against a drug and which are not.

Statements and explanations provided with regard to a single characteristic likewise applies to the case of two or more characteristics, and vice versa. Likewise, statements with regard to a single particle likewise apply to the case of two or more particles, and vice versa.

To this end it is conceivable that the movement of a single particle is imaged during at least one moment in time or that the movement of two or more, in particular of a plurality of particles is preferably collectively imaged during at least one moment in time. In this context, it should be noted that the individual characteristics of two or more particles can be derived simultaneously. Namely, and as will be explained in greater detail further below, by recording one or more images of for example two particles and by subsequently analyzing said one or more images, it is possible to derive a characteristic associated with one of the particles as well as to derive a characteristic associated with the other particle.

It is furthermore conceivable that the movement of the one or more particles is imaged repeatedly.

The method may comprise
  imaging the movement of at least one free-floating particle in a liquid environment at at least a plurality of moments in time
  determining for each of said plurality of moments in time a movement parameter based on the imaged movement of the free-floating particles, and
  deriving from said different movement parameters a characteristic of the at least one particle.

The at least one moment in time during which the movement of the one or more particles is imaged preferably corresponds to a period of time in the range milliseconds to minutes, for example 1 millisecond to 60 minutes. Hence, it is conceivable that the at least moment in time during which the movement of the particle is imaged corresponds to a period of 1 second or more, more preferably to a period of time of 5 seconds or more, even more preferably to a period of time of 10 seconds or more. However, longer periods of time such as a period of time of 120 seconds or more are likewise conceivable.

The movement of the at least one free-floating particle is preferably imaged as a function of time, and wherein the movement parameter is determined as a function of time.

Hence, the method may comprise the step of imaging the movement of at least one particle as a function of time. As a result, the method enables the determination of a characteristic associated with the at least one particle as a function of time.

The method may comprise i) imaging the movement of the at least one free-floating particle at at least two moments in time, whereby at least a first imaged movement and a second imaged movement is obtained, and ii) determining a change between the first imaged movement and the second imaged movement, and wherein said change is indicative of the movement parameter.

That is to say, it is preferred to detect two or more images of the movement of the particle and to determine a change in said images, wherein said change is indicative of one or more movement parameters. From said one or more movement parameters one or more characteristics of the particle can then be derived. In other words, the method allows the derivation of one or more characteristics of one or more particles by recording two or more images.

It is furthermore preferred that two consecutive images are recorded immediately after one another or temporarily delayed with respect to one another. A temporal delay between the recording of two successive images is preferably at least 1 millisecond or longer, more preferably at least 1 second or longer, even more preferably at least 1 minute or longer, for example 30 minutes or longer, or at least 60 minutes or longer.

The change preferably corresponds to a spatial displacement of the free-floating particle and/or to a velocity associated with the spatial displacement of the free-floating particle and/or to an acceleration associated with the spatial displacement of the free-floating particle and/or to a distribution of the spatial displacement of the free-floating particle and/or to a distribution of the velocity associated with the spatial displacement of the free-floating particle and/or to a distribution of the acceleration associated with the spatial displacement of the free-floating particle.

The at least one particle may be at least one cell and/or at least one organelle. The at least one particle preferably is at least one living cell and/or at least one living organelle. The at least one cell can be a prokaryotic cell and/or an eukaryotic cell. The at least one cell can also be a motile cell and/or a non-motile cell. The at least one cell preferably is a bacterial cell and/or a fungal cell such as a yeast cell, and/or mammalian cell and/or insect cell and/or vegetal cell. The at least one organelles preferably are mitochondria and/or a nuclei or any other subcellular structure. A plurality of particles can be provided in the form of a group of cells. To this end an aggregation of several cells could be taken from a biopsy, for example.

Living matter displays another behaviour than dead matter or impaired matter which manifests itself, inter alia, In the displacement behaviour of the matter. By deriving a spatial displacement or by deducing further properties or quantities such as an associated velocity or an associated acceleration or a distribution of the displacement or the velocity or of the acceleration, information on the condition of the matter can be derived. For example, the spatial displacement(s) of a dead or impaired cell are reduced as compared to the spatial displacement(s) of an active cell. Furthermore, it has been determined that a non-symmetric distribution of the spatial displacement(s) or of the velocity or acceleration associated with the spatial displacement(s) can be attributed to a non-random behavior of an active cell. Inactive or dead cells in turn display a small and rather symmetric distribution of their spatial displacement(s) and/or velocity and/or acceleration.

A characteristic of the at least one particle may be a viability or a metabolic activity or a level of metabolic activity or a metabolic state or a vitality or a sensitivity or a resistance of the at least one particle. The resistance preferably corresponds to a resistance to a drug such as an antibacterial resistance and/or an anti-fungal resistance and/or an anti-cancer resistance.

Deriving from said movement parameter a characteristic of the at least one particle may comprise taking into account that the amount of movement of the particles, in particular the amount of translation and/or of rotation and/or of deformation of the particles, is proportional with viability and/or a metabolic activity and/or a level of metabolic activity and/or a vitality and/or a sensitivity and/or a resistance of the at least one particle.

The method may comprise deriving particle activity and/or a viability and/or a metabolic activity and/or a level of metabolic activity and/or a metabolic state and/or a vitality and/or a sensitivity and/or a resistance of the at least one particle. The method preferably comprises deriving a resistance of the at least one particle to a drug such as an antibacterial resistance and/or an anti-fungal resistance and/or an anti-cancer resistance.

Hence, it is preferred to determine at least one of a spatial displacement, a velocity associated with the spatial displacement, an acceleration associated with the spatial displacement, a distribution of the spatial displacement, a distribution of the velocity associated with the spatial displacement, and an acceleration associated with the spatial displacement from two or more imaged movements of the particle so as to obtain the at least one movement parameter, and wherein the at least one characteristic of the particle is then determined from said one or more movement parameters.

To this end it is particularly preferred that the spatial displacement and/or the velocity associated with the spatial displacement and/or the acceleration associated with the spatial displacement and/or the distribution of the spatial displacement and/or the distribution of the velocity associated with the spatial displacement and/or the distribution of the acceleration associated with the spatial displacement corresponds to the at least one movement parameter.

It is furthermore preferred that the spatial displacement and/or the velocity associated with the spatial displacement and/or the acceleration associated with the spatial displacement and/or the distribution of the spatial displacement and/or the distribution of the velocity associated with the spatial displacement and/or the distribution of the acceleration associated with the spatial displacement is determined as a function of time.

Moreover, it is preferred that the spatial displacement is determined with respect to at least one spatial direction. In particular, the spatial displacement, and consequently associated quantities such as the velocity and/or acceleration can be determined with respect to a single spatial direction only. However, it is likewise conceivable to determine the spatial displacement, and consequently associated quantities such as the velocity and/or acceleration, with respect to two or more spatial directions. Said two or more spatial directions preferably extend perpendicular to one another.

Hence, it is conceivable that the spatial displacement is determined with respect to a single spatial direction only, from which spatial displacement the movement parameter is deduced or which spatial displacement corresponds to the movement parameter. Said spatial direction can be referred to as X direction and a spatial displacement with respect to the X direction can be referred to as X movement or as X displacement or as X motion, for example. Thus, it should be noted that a movement as referred to herein can be understood as a displacement and as a motion and vice versa.

A spatial displacement or associated quantities are preferably determined with respect to a single spatial direction of the at least one particle when said particle is provided in a liquid environment that is subject to a flow. In fact, it is preferred to let the liquid environment flow along a spatial direction and to measure the spatial displacement of the particle with respect to another spatial direction. For example, the liquid environment could flow along the X direction and the spatial displacement of the particle could be determined with respect to the Y direction running perpendicularly to the X direction. The liquid environment is preferably subject to a forced convective flow such as a forced laminar flow or a forced turbulent flow existing within the channel of a microfluidic device, see also further below.

It is however likewise conceivable that the spatial displacement is determined with respect to two spatial directions, from which spatial displacement the movement parameter is deduced or which spatial displacement corresponds to the movement parameter. Said two spatial directions can be referred to as X direction and Y direction, and wherein a spatial displacement with respect to the X direction and the Y direction can be referred to as X, Y movement or as X, Y displacement or as X, Y motion, for example.

It is likewise conceivable that the spatial displacement is determined with respect to three spatial directions, from which spatial displacement the movement parameter is deduced or which spatial displacement corresponds to the movement parameter. Said three spatial directions can be referred to as X direction, Y direction and Z direction, and wherein a spatial displacement with respect to the X direction and the Y direction and the Z direction can be referred to as X, Y, Z movement or as X, Y, Z displacement or as X, Y, Z motion, for example.

The X direction, Y direction and the Z direction can be referenced to a Cartesian coordinate system, wherein the X direction and Y direction can be said to span a horizontal plane, i.e. an XY plane. Furthermore, the X direction and the Y direction can extend perpendicularly with respect to the Z direction. The Z direction can also be referred to as a vertical direction as well as to the direction along which the imaging of the one or more particles occurs. However, for providing a coordinates reference system any other system can be used as well. For example, a polar coordinate system and/or a circular coordinate system and/or a cylindrical coordinate system are likewise possible.

The method may comprise deriving an X movement and/or a Y movement and/or a Z movement and/or an X, Y movement and/or an X, Y, Z movement of the at least one particle.

The method may comprise deriving the spatial displacement of the at least one particle with respect to each one of the one or more spatial directions in a range of nanometers to micrometers, for example in a range of about 1 nanometer to 1000 micrometer, more preferably in a range of about 1 nanometer to 100 micrometer. To this end it is therefore preferred that the method is capable of imaging a spatial displacement between at least the first imaged movement and the second imaged movement with respect to the at least one spatial direction in the range of about 1 nanometer to 1000 micrometer, more preferably in the range of about 1 nanometer to 500 micrometer, particularly preferably in the range of about 100 nanometer to 100 micrometer.

The method may further comprise determining an amount of the spatial displacement(s) and/or an amount of the associated quantities and wherein the characteristic of the particle is derived from said amount.

From said amount, i.e. the distance by which the particle moves with respect to one or more of the spatial directions or the amount of the associated velocity or acceleration, information on the condition of the particle can be derived, see also above. Additionally or alternatively the method may further comprise determining the amount of the spatial displacement within a certain period of time. In other words, it is preferred to determine one or more distances, preferably a total distance, the particles move within a certain period of time with respect to one or more spatial directions. Information on the condition of the particle can then be derived from said distances.

The spatial displacement can be subjected to a space-to-frequency conversion so as to obtain one or more frequencies being associated with said spatial displacement, and wherein the characteristic of the particle is derived from said one or more frequencies.

In particular, it is preferred to determine the spatial displacement(s) of the particle as a function of time in a first step and to then convert said spatial displacement(s) into the frequency domain. It has been determined that living cells oscillate in another frequency range as dead cells, for example. Therefore, the determination of the frequency being associated with the spatial displacement(s) also enables a determination of the condition of the particle under investigation.

In view of the above it can thus be said that the method may comprise the calculation of a velocity of the spatial displacement and/or the determination of the distribution of the spatial displacement and/or the performing of a frequency domain analysis.

In this context it is preferred that the method further comprises using a conversion algorithm in order to convert the movement of a particle as a function of time into the frequency domain, whereby one or more oscillation frequencies being associated with the imaged movement of the particle are obtained. Said conversion algorithm preferably performs a conversion from space to the frequency domain such as a Fourier transform or the like, see further below.

The movement may be an oscillation and wherein the movement parameter is an oscillation movement parameter.

The distribution of the spatial displacement is preferably determined by conventional statistical analysis such as the generation of so-called Violin plots and/or box plots. The frequency domain analysis is likewise preferably performed by means of known methods such as a Fast Fourier Transform (FFT), or wavelets. Hence, the method preferably comprises using one or more corresponding algorithms that are capable of performing one or more of these analysis and calculations, etc.

The spatial displacement preferably corresponds to a translation of the free-floating particle and/or to a rotation of the free-floating particle and/or to a deformation of the free-floating particle. The rotation can be referred to as an angular displacement the particle exhibits with respect to one or more of the spatial directions. The angular displacement is preferably indicated in cylindrical coordinates.

The deformation of the particle can be understood as a change of shape of the particle. The change of shape can be caused by changes of osmotic pressure inside the cell, rearrangement of the cytoskeleton within a cell, a change of the volume of the cytoplasmic space, a change of the volume of the nucleus, for example. As such, information on the condition of the cell can be derived from an analysis of the change of shape or the deformation.

The whole movement of the at least one particle may be determined. To this end it is conceivable that a spatial displacement of the entire free-floating particle is determined. The spatial displacement of the entire free-floating particle is preferably determined from the spatial displacement of a centre of mass of the particle.

It is however likewise conceivable that the spatial displacement of at least one part of the free-floating particle is determined. The spatial displacement of at least one part of the free-floating particle is preferably determined from a modification of a shape of the particle. In other words, the spatial displacement of a part of the particle is preferably derived for a stationary centre of mass of the particle. The spatial displacement of a part of the particle could be a deformation of the shape of a cell caused by changes of osmotic pressure inside the cell, by a rearrangement of the cytoskeleton and/or caused by cellular organelles displacement, for example.

The method may comprise detection of at least one particle using an area that comprises the particle or part of the particle.

The analysis may comprise any or a combination of determining movement of the whole particle, determining particle wall displacements and organelles displacements.

The spatial displacement can be determined using a cross-correlation algorithm. Conceivable cross-correlation algorithms are well-known in the art. To this end it is preferred to compare detected displacements or motions or movements at subpixel resolution. In particular, a change with respect to one or more of the spatial directions is detected at subpixel resolution, and wherein said data set if used for an analysis in the frequency domain and/or the time domain.

The method may comprise cross-correlating based on analysis of the nanomotion. The expression nanomotion refers here to the motion. i.e. movement or displacement, that is exhibited by the particle under investigation. Depending on the type of particle said motion can be in the nanometer range.

The method may comprise cross-correlating the one or more images depicting the movement of the at least one particle at at least one moment in time. It is particularly preferred to cross-correlate consecutive images of the at least one particle.

The method may thus comprise using a cross-correlating algorithm.

The cross-correlating algorithm enables a quantification of the movement of the at least one particle, in particular a quantification of the movement with respect to the one or more spatial directions such as the X direction and/or with respect to the Y direction and/or with respect to the Z direction. A quantification with respect to the X direction is understood as a numerical value associated with the movement of the particle under investigation with respect to the X direction, etc. To this end the cross-correlating algorithm is preferably configured to calculate numerical values relating to the movements with respect to the spatial direction(s) for each image i.e. frame.

By quantitating the changes in the movements of the particle changes in the characteristics of the particle such as changes of its viability or the level of its metabolic activity, metabolic state such as dormancy, resting cell, sensitivity or resistance to different chemicals.

The method may further comprise performing one or more statistical analyses such as Violin plots and/or box-and-whisker plots. For example, it is conceivable to plot the imaged movements of a particle, in particular the imaged movements per frame, as a violin plot and/or as a box-and-whisker plot, see also further below.

The movement parameter can be determined from the imaged movement of a single particle. Naturally, two or more movement parameters can be determined from the imaged movement of two or more particles, wherein each movement parameter is associated with a particular particle. However, it is likewise conceivable that the movement parameter is determined from the imaged movement of two or more, preferably of a plurality of particles, and wherein an average or mean value associated with the spatial displacement and/or the associated velocity or the distribution of the spatial displacement or the velocity is used. This latter case is preferably applied when several particles, for example a cell population, shall be investigated.

The method may further comprise selecting one or more particles for the determination of the movement parameter, wherein said selection corresponds to a manual selection and/or to an automatic selection. For example, when manually selecting the one or more particles a user can draw a square box or circle or any other selection marking over at least part of the particle that is used for the displacement with respect to one spatial direction such as the X direction so as to track the displacement with respect to said X direction, and a second squared box is drawn over at least part of the particle that is used for the displacement with respect to a second spatial direction such as the Y direction. The automatic selection is preferably performed by the application of one or more morphological operators and/or a Hough transformation and/or a neuronal network and/or a deep learning technique.

Hence, especially in the event that one or more single particles shall be investigated individually it is preferred to select or choose said one or more single particles from the images. As just stated, said selection can be done manually or by means of one or more algorithms being well-known in the art.

In view of the above it can therefore be said that the method may comprise using at least one algorithm for selecting the one or more particles and/or for determining the movement parameter such as the spatial displacement(s) and/or for quantitate the movement parameter such as the spatial displacement(s) of the at least one particle.

The method may comprise using a neural network. Said neural network can be applied for the selection of the particles such as the cells before their displacement, their nanomotion is detected. The neural network operates to generating a plurality of synthetic images of simulated particles, and to providing such synthetic images to a particle detection model for training the model and updating the model, assessing the model and improving it, so as to obtain a trained model.

The method may comprise detection of at least one particle using a trained model.

The method may comprise refining the detection of the at least one particle using the trained model.

The method may comprise using a deep learning technique. The deep learning technique preferably corresponds to an algorithm that operates to detect individual particles and to track the motion of the individual particles.

However, different image recognition algorithms used in the field of the art can be used as well.

The at least one free-floating particle can be provided in a stationary liquid environment and/or in a flowing liquid environment. A flowing liquid environment can be understood as a moving liquid environment, such as a liquid flowing along a direction of flow. To this end it is preferred that the liquid environment is subject to a flow, particularly preferably to a forced convective flow, so that it becomes a flowing liquid environment. Hence, it is conceivable that the liquid environment is subject to an artificial flow.

The at least one free-floating particle may be a particle not bound to a surface of an object or to a surface of a larger particle. Instead, the free-floating particle is preferably a particle being dispersed in a liquid environment. The liquid environment can be provided in a limiting element such as a chamber or a reservoir or a channel, preferably in a channel of a microfluidic device. In other words, a particle deposition into an analysis chamber such as a micro analysis chamber or a macro analysis chamber, or into a Petri-dish, or into a microfluidic channel is conceivable. Hence, the limiting element is understood as a physical structure which comprises or encompasses the liquid to which the particle is added. The limiting element is preferably untreated. An untreated limiting element is understood as a limiting element that has not been modified with respect to an attachment or tethering of the particle to the limiting element. Consequently, the particle will not attach or tether to the limiting element but is free-floating.

It is however likewise conceivable that the liquid environment is provided in an unlimited manner. For example, and as will be explained further below, the liquid to which the particle is added could be placed directly onto an optical sensor being used for imaging the movement of the particle. For instance, the liquid environment could be provided by means of a micro droplet or macro droplet being placed onto the optical sensor. Also in this case the particle is not tethered or attached to any surface or the like but is free-floating.

The liquid environment may be a diffusion environment wherein the movement of the particles is not disturbed by convection. In other words, the movements of the particles are preferably imaged in the absence of convection. The liquid can correspond to any kind of liquids such as a preferably biocompatible and/or water-based artificial fluid or a natural fluid, e.g. biological fluids in which the particles such as the cells can survive and can be tested for their metabolism or survival upon exposure to the physico-chemical agents, see also below. Examples of natural fluids are urine, cerebro spinal fluid, sputum, or blood. Additionally or alternatively, the liquid environment can be subject to a preferably forced convective flow.

The at least one free-floating particle can be subjected to one or more chemical stimuli and/or one or more physical stimuli, and wherein the movement of the at least one free-floating particle is imaged before and/or during and/or after the action of said one or more chemical stimuli and/or physical stimuli.

Chemical stimuli could correspond to the addition of chemicals, drugs or agents or to the exposure to biomolecules, for example. Physical stimuli could correspond to a change in temperature of the liquid environment comprising the particles, the irradiation of light, for example UV light, the application of or change in pressure of the liquid environment, etc.

Hence, the method may comprise the addition of one or more compounds to the liquid environment, and wherein an impact of the one or more compounds on the at least one free-floating particle is derived from the movement parameter.

The one or more compounds can be essentially immiscible with the liquid environment. Additionally or alternatively the one or more compounds can be provided in one or more further compounds, the one or more further compounds preferably being essentially immiscible with the liquid environment.

For example, it is conceivable to add one or more droplets or the like of one or more first compounds being immiscible with the liquid constituting the liquid environment such as oil to the liquid in a first step, and to then add one or more second compounds such as antibiotics or antifungals to the droplets. Thereafter, the particle can be allowed to interact or communicate with the droplets, wherein an impact of the second compounds comprised in the droplets on the particle is investigated. To this end it should be noted that the compounds constituting the droplets can be the same or different from one another. Likewise, the compounds being added to the droplets can be the same or different from one another. It is also conceivable that the same kind of compound is added to the droplets, however in varying concentrations. More modifications, such as the application of different physical stimuli to the different droplets, etc., are likewise conceivable.

Hence, the method may comprise an investigation of the at least one particle in response to chemical stimuli and/or physical stimuli. In particular, the method may comprise the step of performing an antibiotic susceptibility testing and/or an antifungal susceptibility testing and/or a characterization of cell viability and/or for metabolism monitoring and/or for performing diagnostics and/or drug screening.

The results of said investigation can be displayed before and/or during and/or after the physical and/or chemical exposure as well as for one or more single particles and/or one or more multiple particles.

The movement of the at least one free-floating particle is preferably imaged with at least one optical sensor, the optical sensor preferably being a COD or CMOS camera.

Hence, the method preferably comprises the provision of at least one optical sensor such as a camera. Said optical sensor is configured to detect one or more images.

The at least one optical sensor preferably images the movement of the at least one free-floating particle with a frame rate of 1 microsecond or more, preferably 1 second or more, more preferably of 10 seconds or more, particularly preferably of 50 seconds or more. Additionally or alternatively the at least one optical sensor images the movement of the at least one free-floating particle at a sub-pixel resolution.

The frame rate of the optical sensor is preferably higher than an oscillation of the particles under investigation. Said frame rate is preferably at least two Hertz, more preferably at least 4 Hertz, particularly preferably at least 6 Hertz. However, it should be noted that higher frame rates are likewise conceivable. For example, a frame-rate of at least 100 Hertz, or of at least 500 Hertz, or of at least 1000 Hertz is also possible.

The method may comprise, at a plurality of moments in time, imaging the movement of at least one free-floating particle by recording a video over a predetermined period of time.

The at least one optical sensor can be stationary during the imaging of the movement of the at least one free-floating particle. A stationary optical sensor is preferred if a spatial displacement of the particle is investigated in one spatial direction, such as a particle flowing along a fluid channel of a microfluidic device. Alternatively, the at least one optical sensor can be moved during the imaging of the movement of the at least one free-floating particle.

The movement of the at least one free-floating particle can be imaged while being magnified by at least one magnifying device such as a microscope.

The method may therefore further comprise magnifying the movement of the at least one particle. As such it is preferred that the method further comprises the provision of a magnifying device, for example a microscope.

Hence, the movement of the particle can be monitored by video recording or an online motion analysis with an optical sensor such as a CCD chip or CMOS chip, or with a combination of a magnifying device such as a microscope and an optical sensor. The microscope can be an optical microscope, a fluorescent microscope, a confocal microscope, or a super resolution microscope, for example. If the spatial displacements with respect to three spatial directions shall be determined it is preferred to use a confocal microscope.

The method may comprise registering different images.

Said imaging may comprise optically recording a movement of the at least one particle.

Said imaging may comprise optically recording with an optical system and a camera.

Said imaging may comprise recording videos of the particles over a predetermined period of time.

Furthermore, the movement parameter can be determined while the movement of the particle is imaged and/or after the movement of the particle is imaged. Additionally or alternatively the characteristic of the particle can be derived from the movement parameter while the movement of the particle is imaged and/or after the movement of the particle is imaged. In other words, the method may enable a data processing of the imaged movement data while the images are recorded and/or after the images are recorded.

The method may furthermore comprise the steps of i) particle preparation, such as preparing a suspension of the particles in an analysis buffer and/or in a growth medium, ii) dilution and/or concentration of said suspension, for example an incubation in the growth medium to increase the number of cells, iii) fluorescent labelling, and iv) exposure to physical and/or chemical stimuli before or after a particle deposition. It should be noted that only one or more of these steps can be applied. In other words, it is conceivable that one or more of these steps are omitted. For example, it is conceivable that no fluorescent labelling of the particles is performed. A fluorescent labelling simplifies a detection of the particles but is not a mandatory step.

In one aspect, the present invention relates to a computer program product comprising instructions which, when the program is executed by a computer system, cause the computer system to carry out the method as described above.

In another aspect, the present invention also relates to a computer-readable medium comprising instructions which, when executed by a computer system, causes the computer system to carry out the method as described above.

In one aspect, the present invention relates to a processor for deriving particle characteristics, the processor comprising an input means for obtaining imaged movement of at least one free-floating particle in a liquid environment at at least one moment in time, a processor for determining for at least one moment in time at least one movement parameter based on the imaged movement of the free-floating particles in the liquid environment and for deriving from the at least one movement parameter at least one characteristic of the at least one particle.

The processor may be configured for performing a method as described above.

In one aspect, the present invention also relates to a system for deriving particle characteristics, the system comprising at least one optical sensor, preferably an optical system comprising a camera, for imaging movement of at least one free-floating particle in a liquid environment at at least one moment in time, and a processor as described above.

As already explained above, the optical sensor preferably is a CCD chip or CMOS chip. The system may further comprise a magnifying device such as a microscope. The microscope can be an optical microscope, a fluorescent microscope, a confocal microscope, or a super resolution microscope, for example.

In a further aspect, the present invention relates to a use of the system as described above for antibiotic susceptibility testing.

In a further aspect, the present invention relates to a use of the system as described above for antifungal susceptibility testing.

To this end it is preferred to deposit the particles to be tested on a substrate. For example, a biological fluid comprising the particles to be tested could be placed into a reservoir, a well or a microwell. Thereafter the movement of the particles is imaged as a function of time. Thereafter, the particles are exposed to drugs or physical or chemical agents/stimuli. Thereafter, the modifications or changes of the particle movements upon exposure to the just mentioned stimuli is recorded and the thus obtained data is processed as described above.

In the following one non-limiting example is given:

The cellular X, Y displacements are monitored by recording 12 s long movies (1000 frames) taken at a magnification of a microscope of 400×. By periodically recording these movies, the temporal behavior of the cells is characterized as a function of different concentrations of an antifungal. To track the cellular displacements of single cells, a cross-correlation image registration algorithm is used. The cell displacement for each frame, the trajectories of tracked cells as well as the root mean square of the total displacement are calculated. Single cell displacements. i.e. nanomotions are characterized by plotting the distribution of the displacements per frame as a violin plot. The motions of the set of 20 cells is characterized by plotting grouped cellular displacements per frame as violin plots and the total displacements of 20 cells over 1000 frames as box-and-whisker plots.

In a further aspect, the present invention relates to a use of the system as described above for characterizing cell viability and/or for metabolism monitoring.

Namely, and as already mentioned, the method according to the invention enables the determination of a spatial displacement and/or of an oscillation being associated with said spatial displacement of a particle such as a cell, wherein said spatial displacement or oscillation is indicative of a condition of the cell. In fact, when the viability of the cell is compromised a change in the oscillation or the spatial displacement is determined. Similar findings apply to the characterization of the metabolism or the metabolic state or the vitality, etc. of a particle such as a cell.

In a further aspect, the present invention relates to a use of the system as described above for diagnostics and/or drug screening and/or antimitotic drug susceptibility testing.

In the event of a diagnostics it is preferred to find a strain that is resistant to a specific antifungal and/or to find a strain that is persistant to a specific antifungal using the method as described above. In the event of a drug screening it is preferred to find a compound that reduces the spatial displacement or the oscillation being associated with said spatial displacement using the method as described above. In this way, an effective fungistatic or fungicidal compound or bacteriostatic or bactericidal compound can be found in an efficient manner.

It should be noted that any statements and explanations provided herein with respect to the method likewise apply to the computer program product, the computer-readable medium, the processor, the system, the usage of said system, and vice versa. Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings, FIGS. 1a-1d shows an overview of the cross-correlation optical nanomotion detection method, as can be used in an embodiment of the present invention. a, Time period of cells in growth medium followed by antifungal treatment. b, At different time points, movies are recorded of 1000 frames (83 frames per second). Cell movements within the box are detected and analysed. c. The x y displacements of individual cells are calculated using the cross-correlation algorithm. d, The mean of the total displacements of 20 cells is calculated for each sampling point;

Figure 6A:
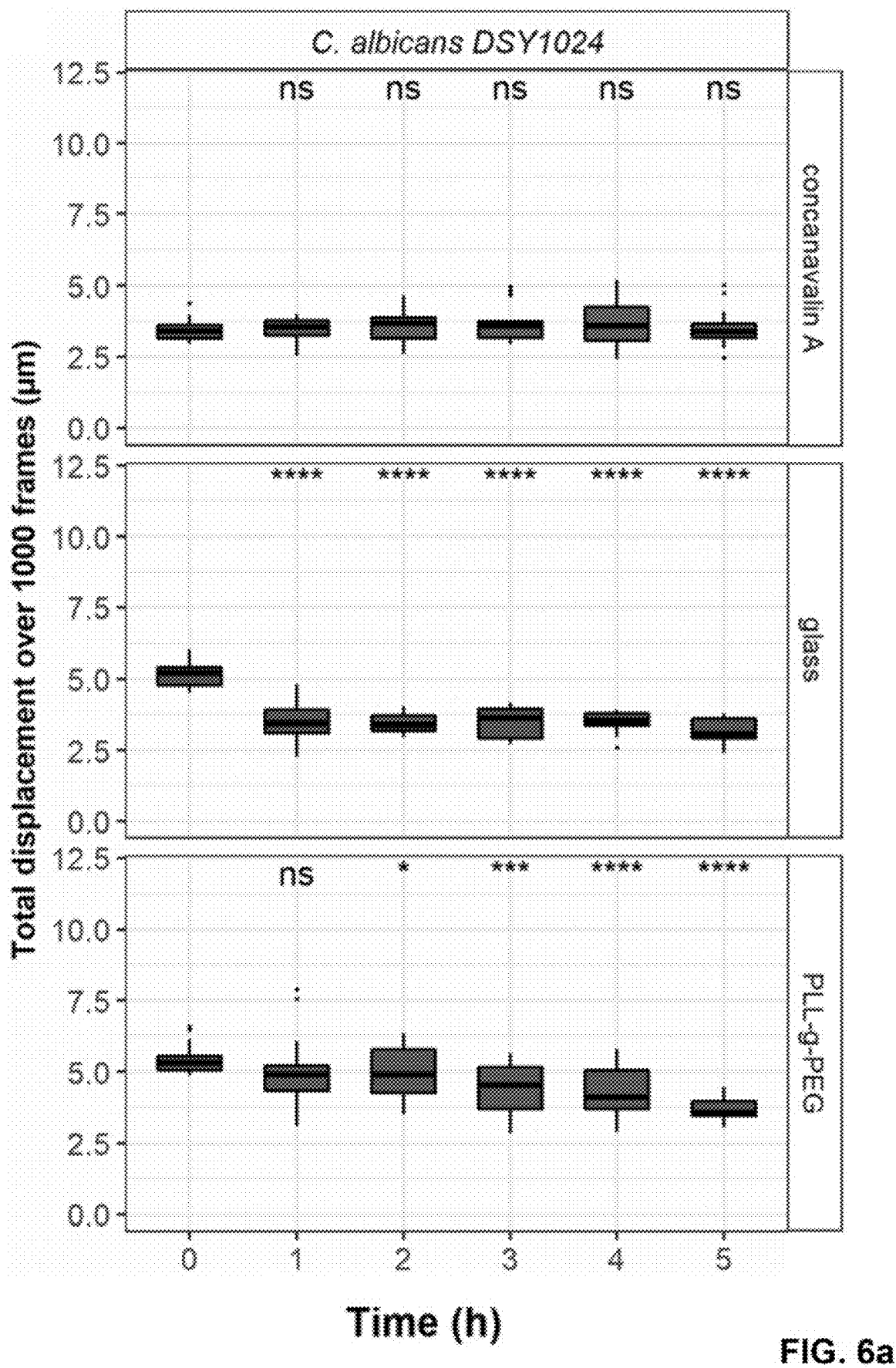
Figure 6B:
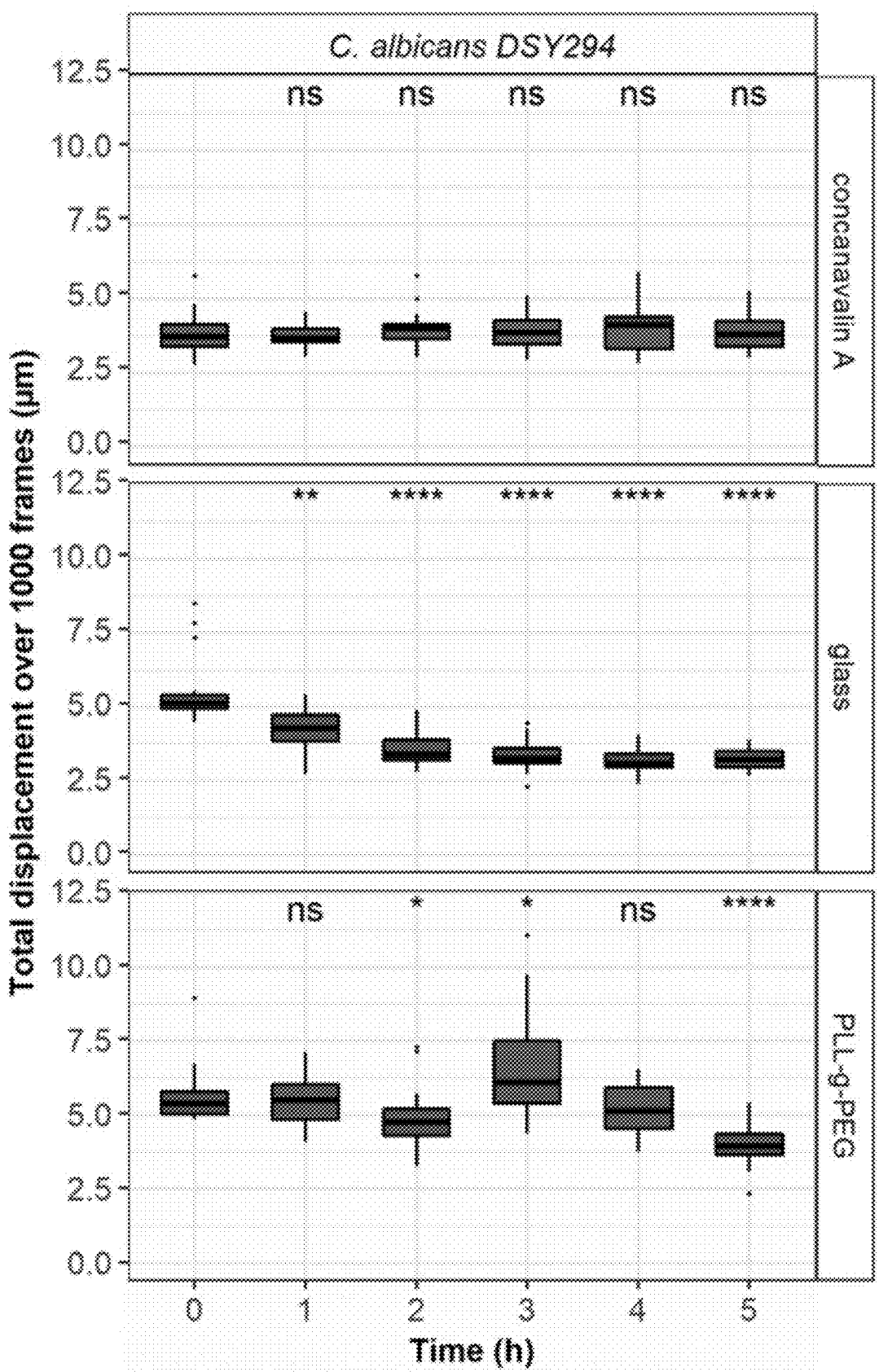
Figure 6C:
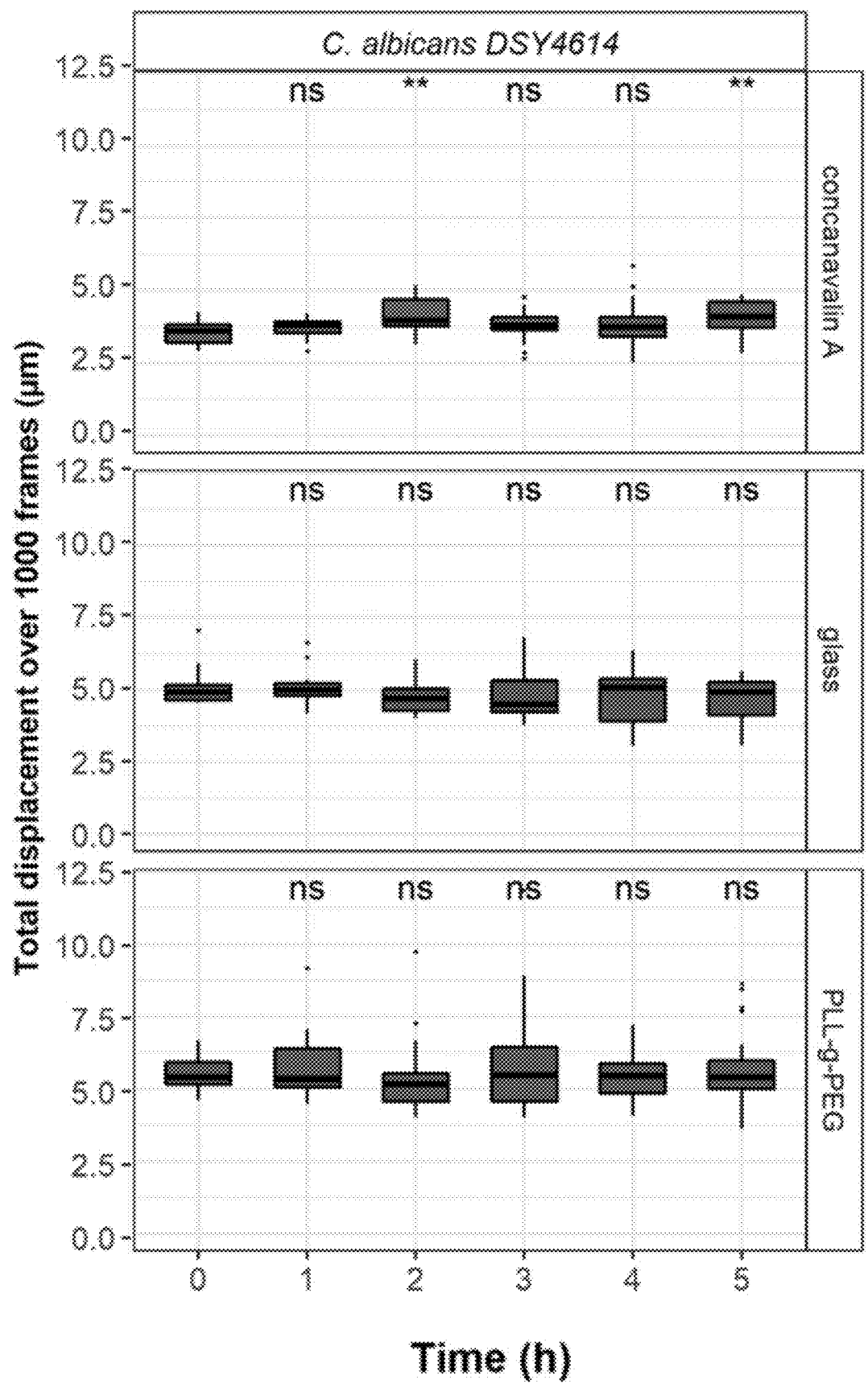
Figure 6D:
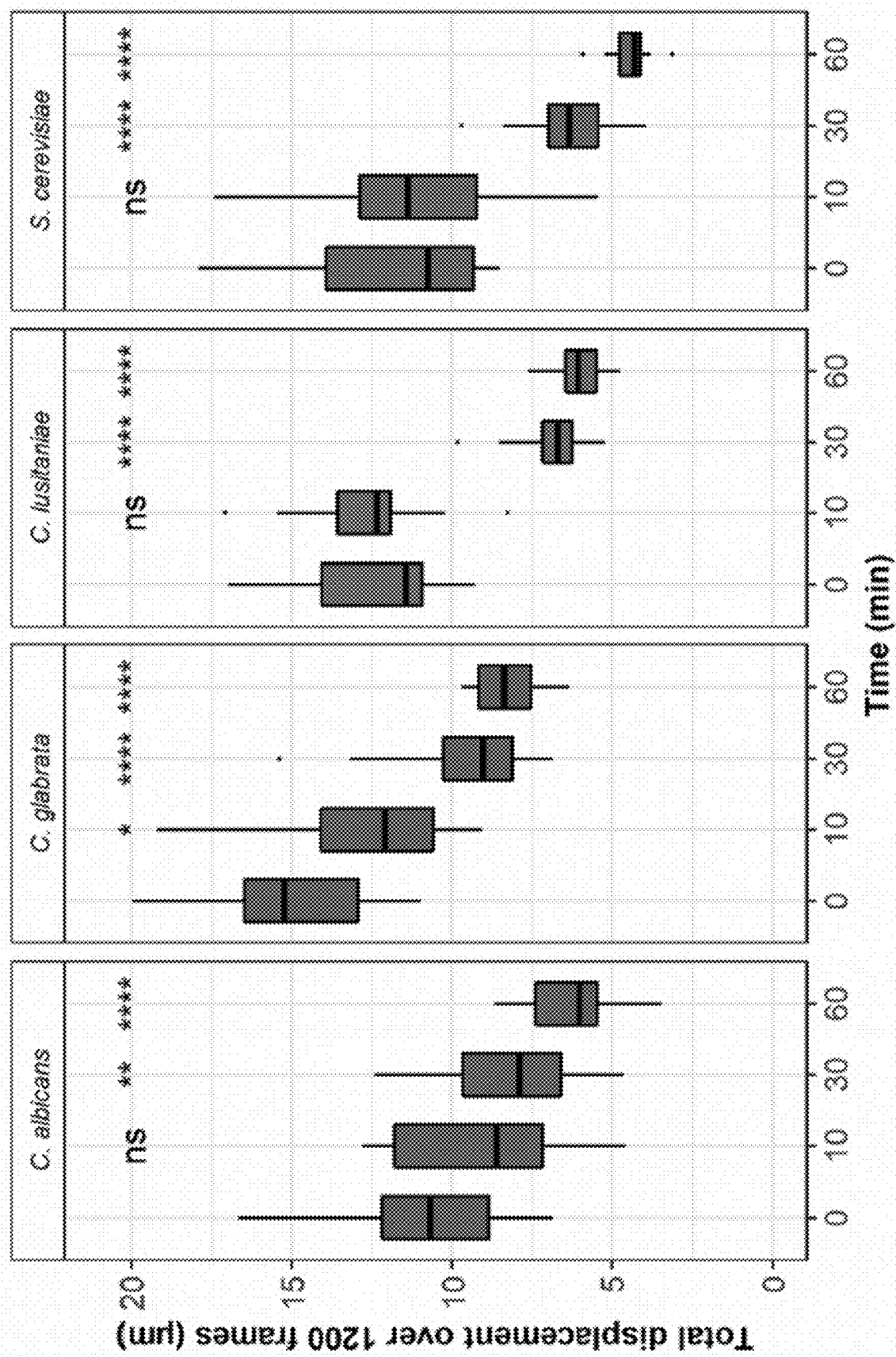
Figure 7A:
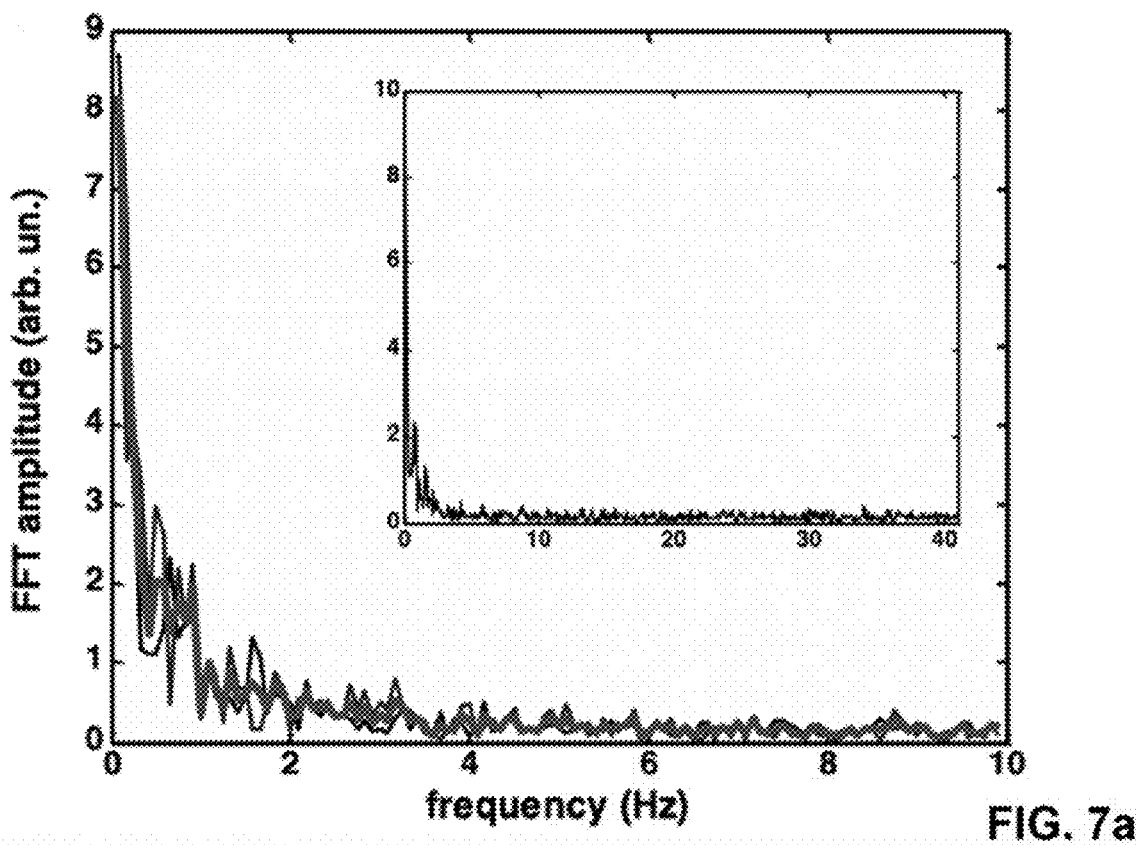
Figure 7B:
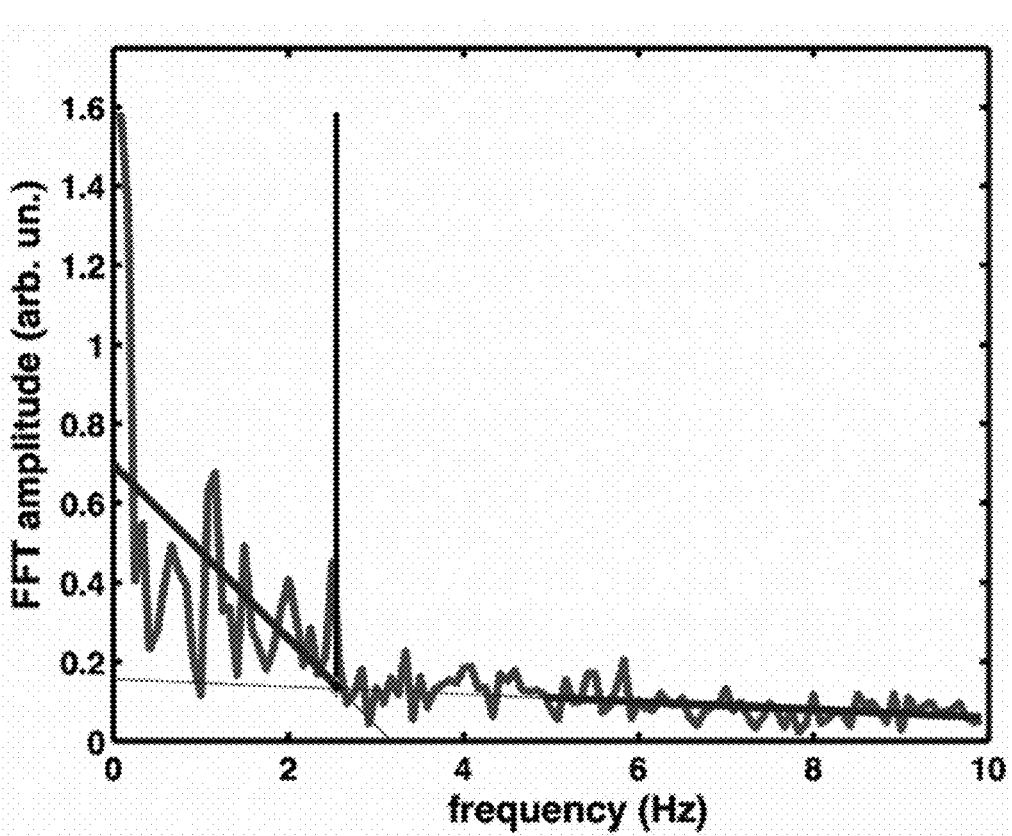
Figure 7C:
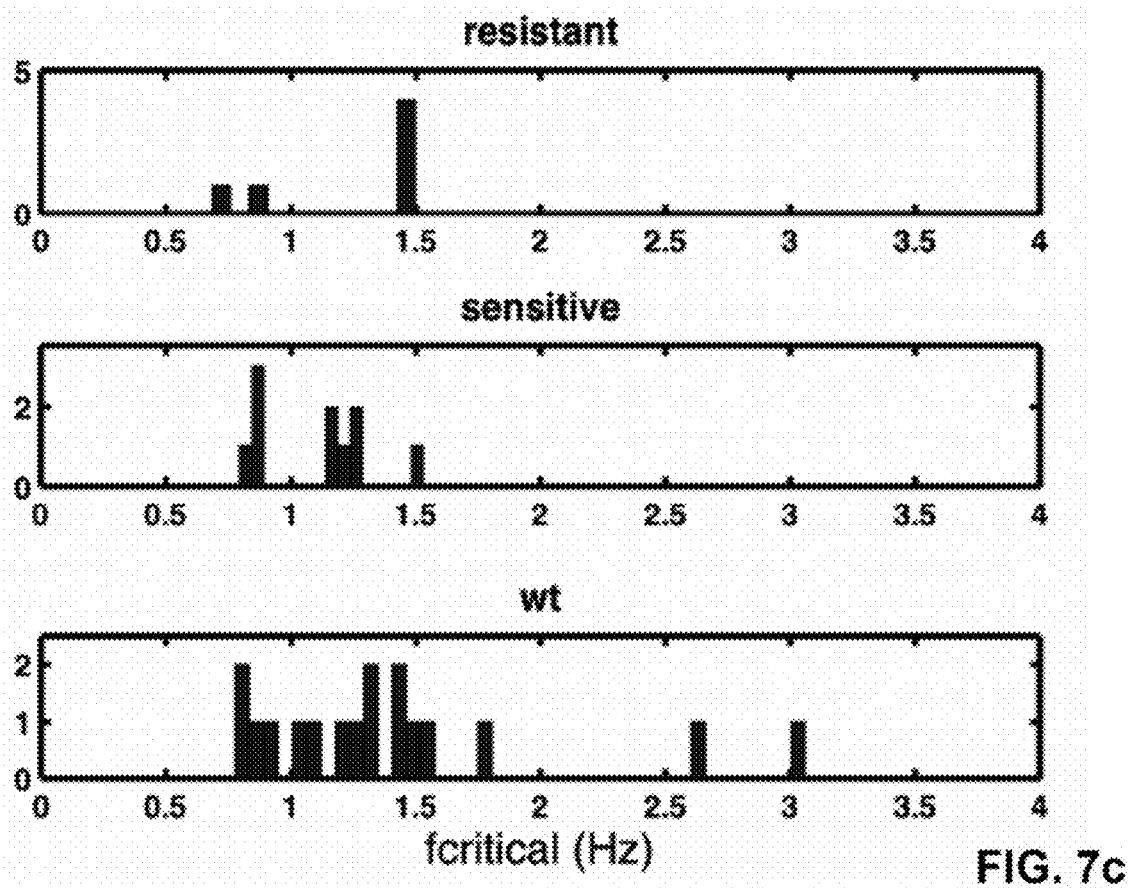
Figure 7D:
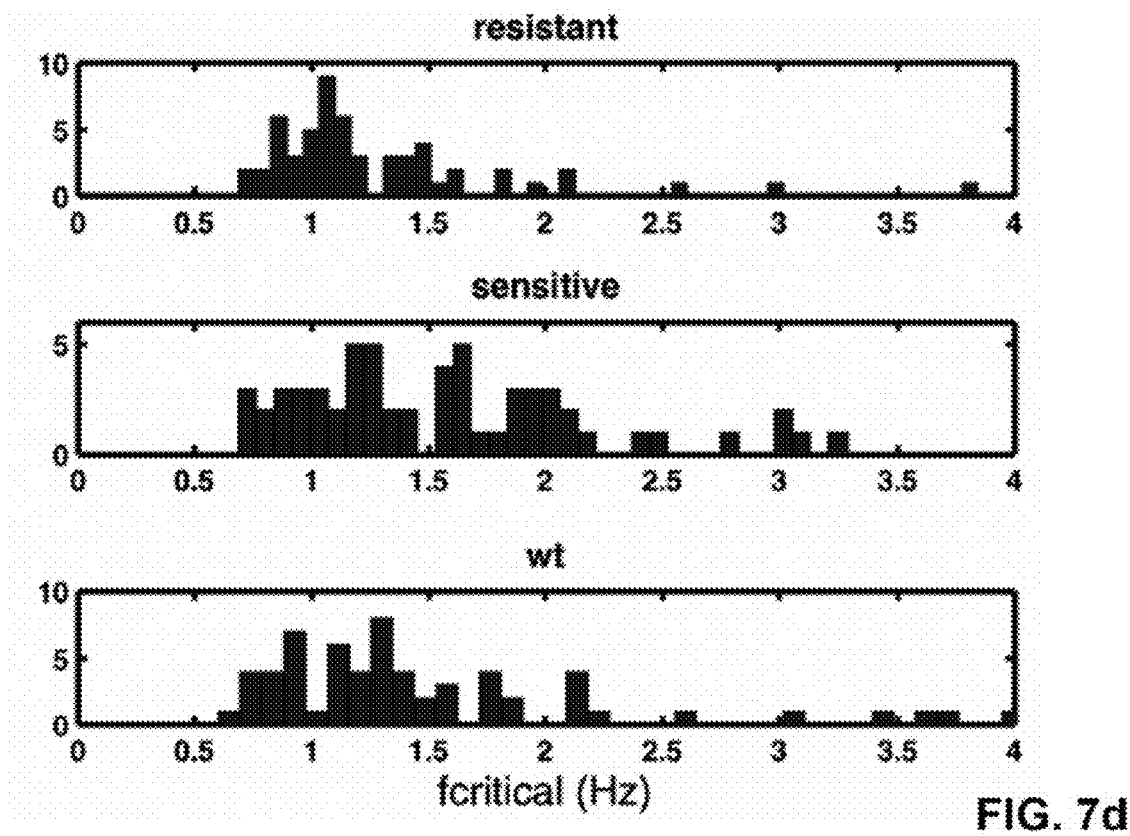
Figure 8:
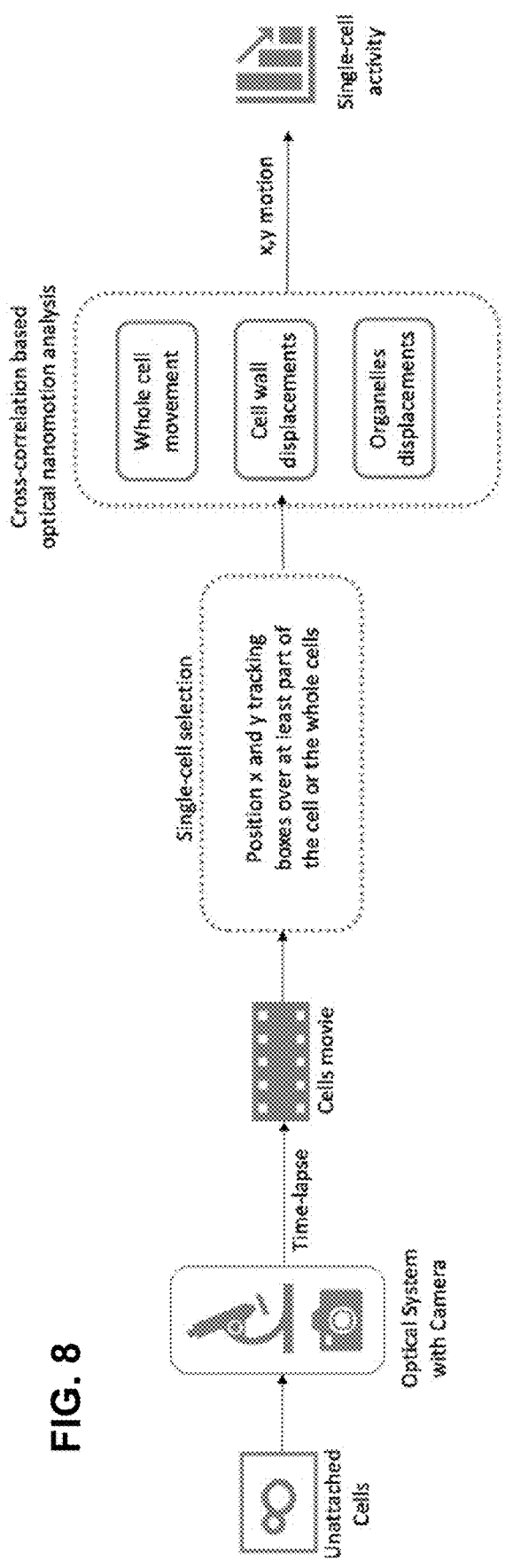
Figure 9:
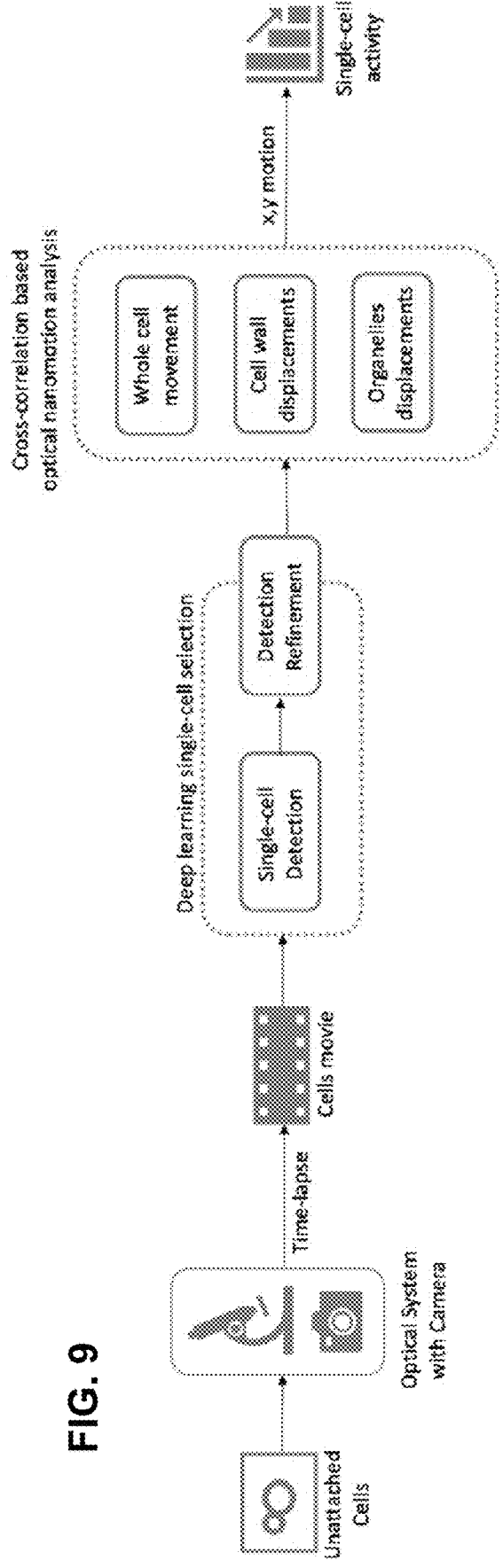
Figure 10A:
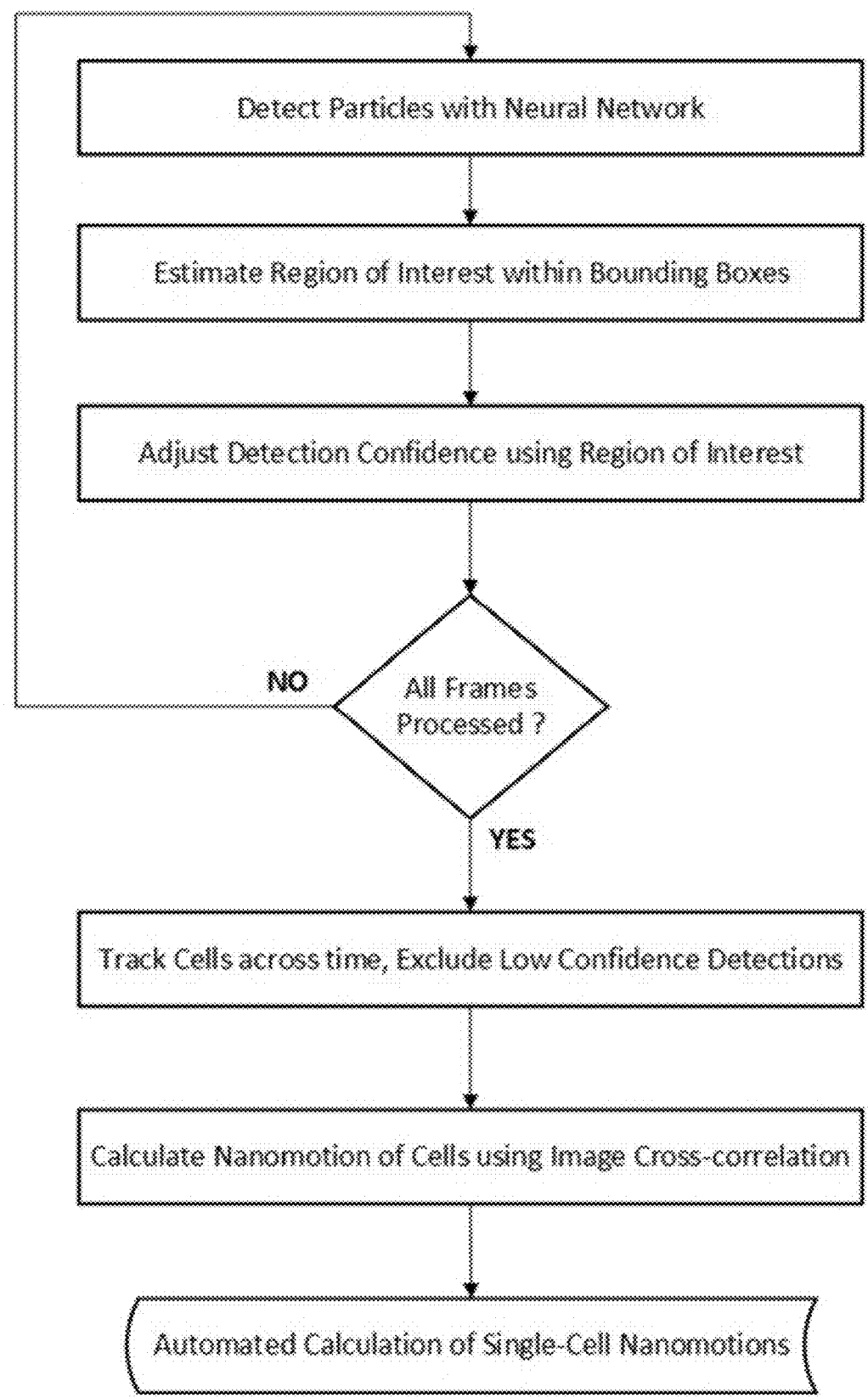
Figure 10B:
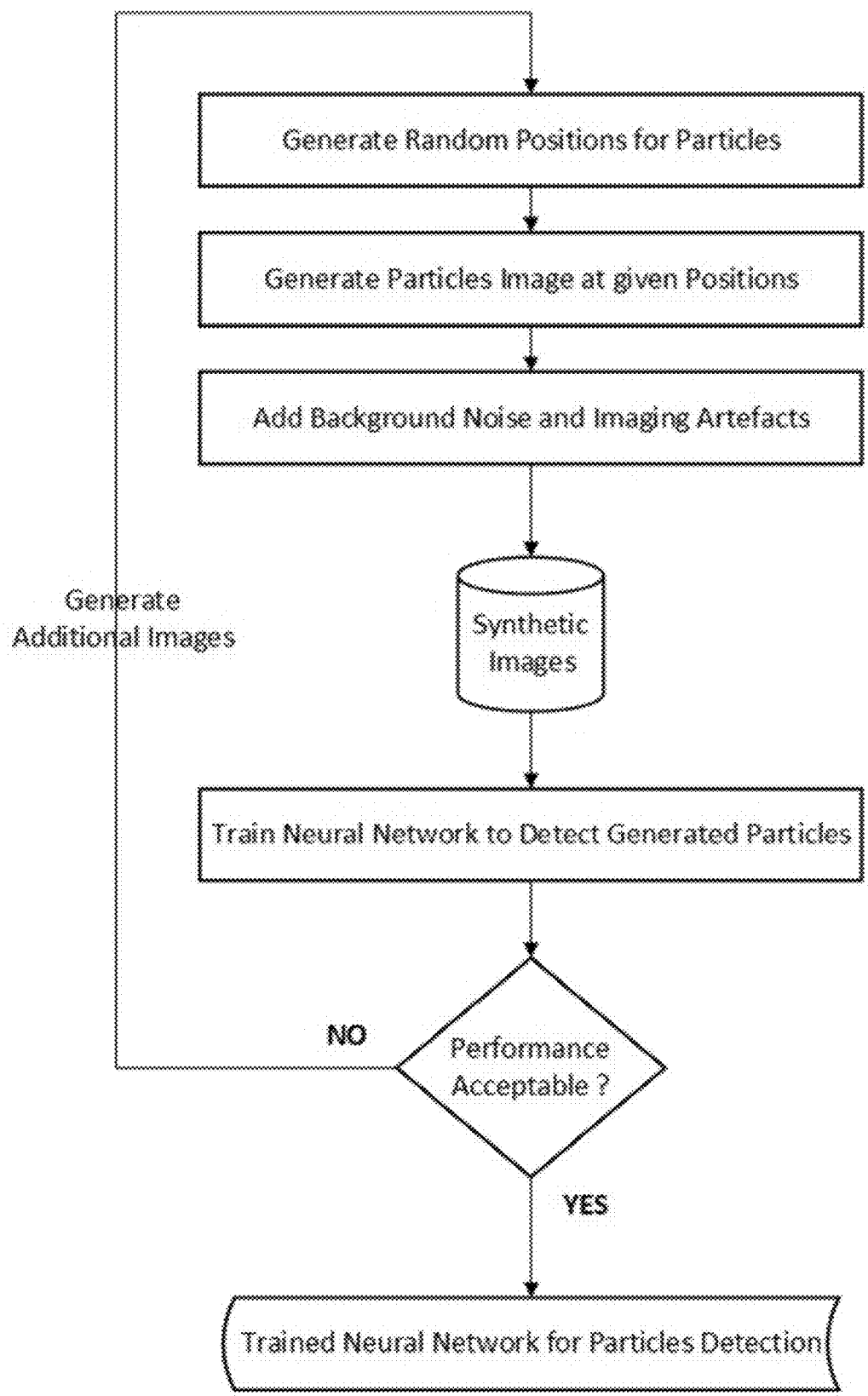
Figure 12:
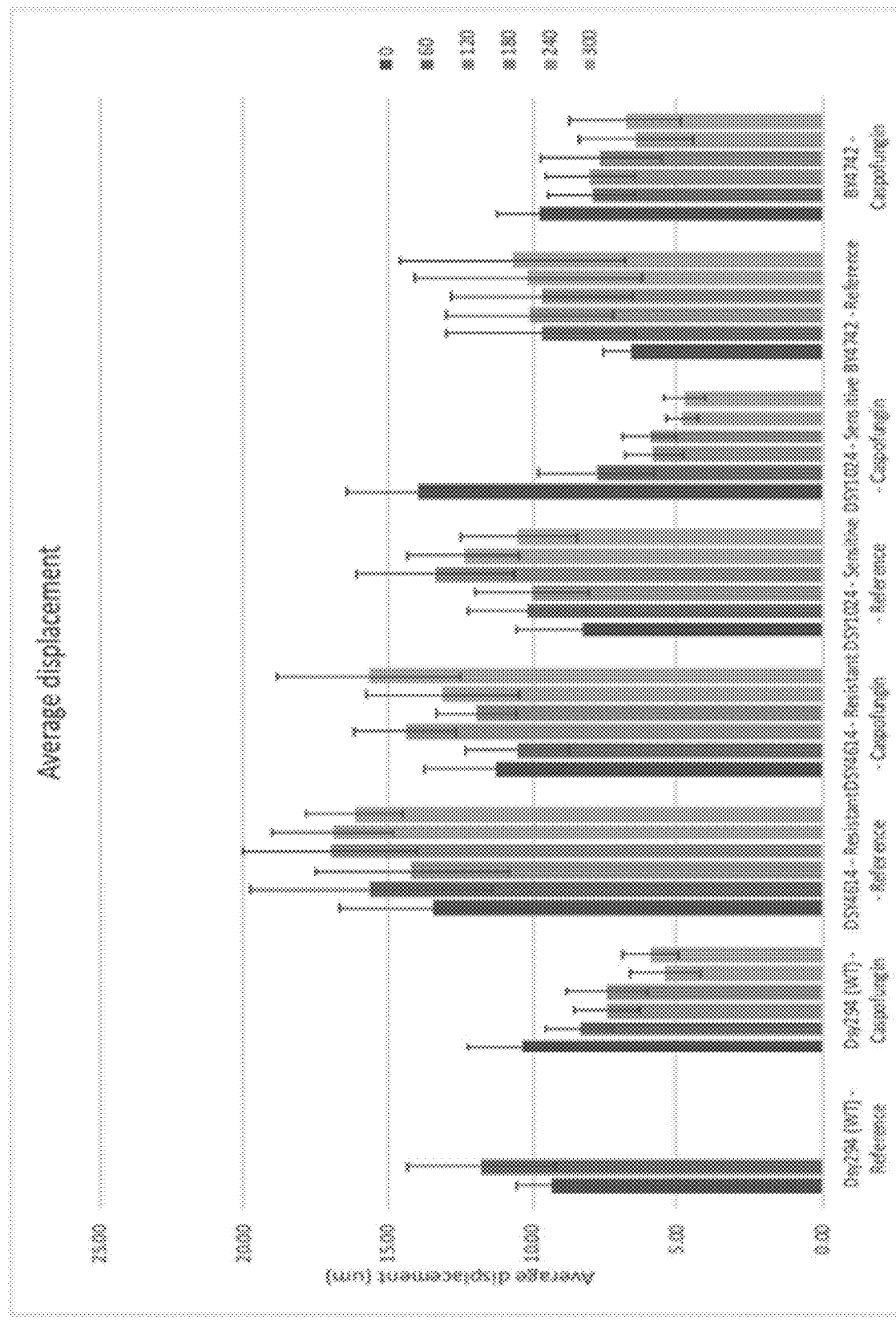
Figure 14A:
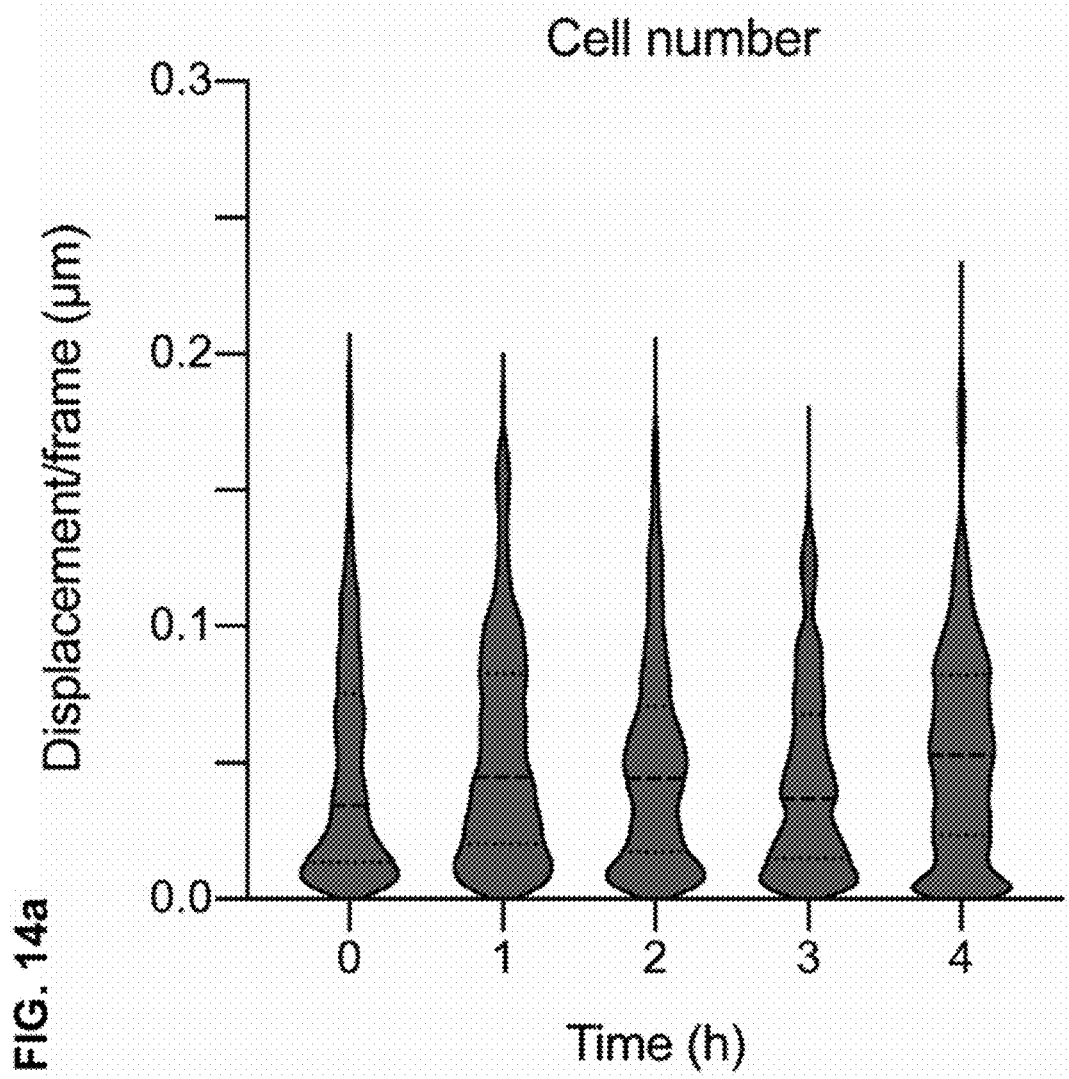
Figure 14B:
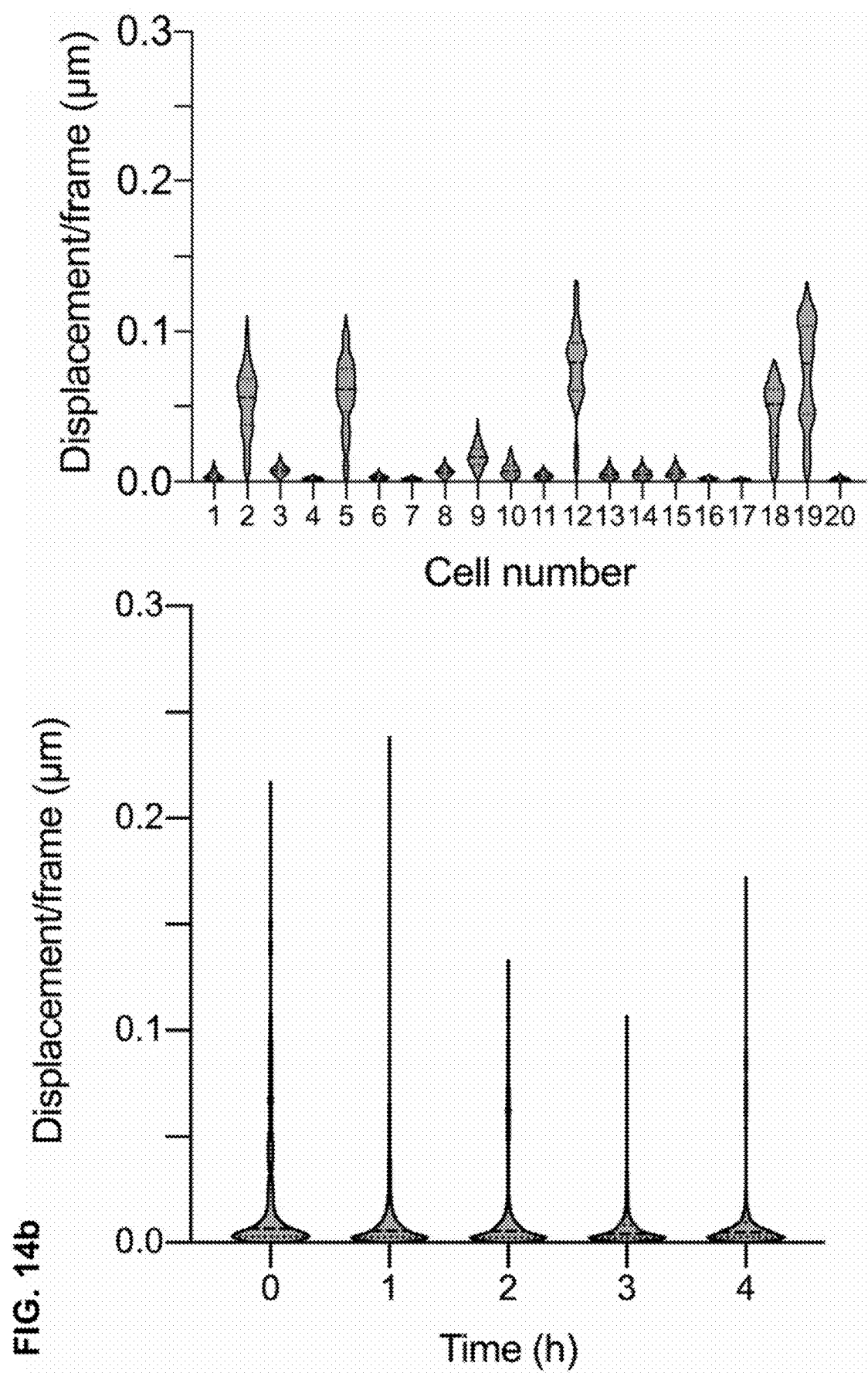
Figure 14C:
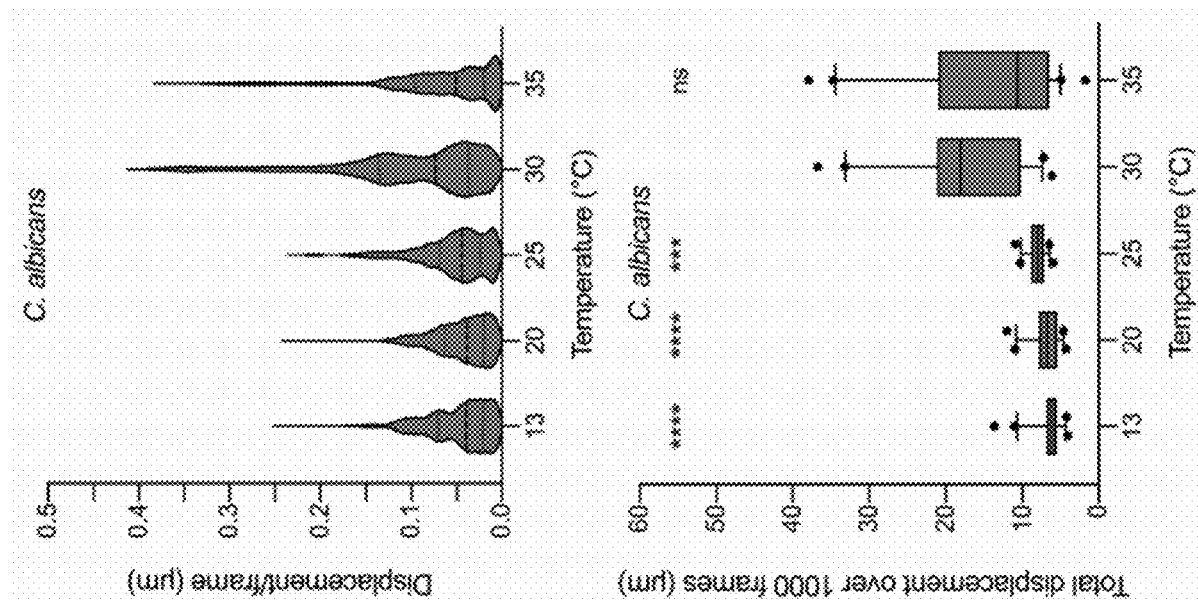
Figure 14D:
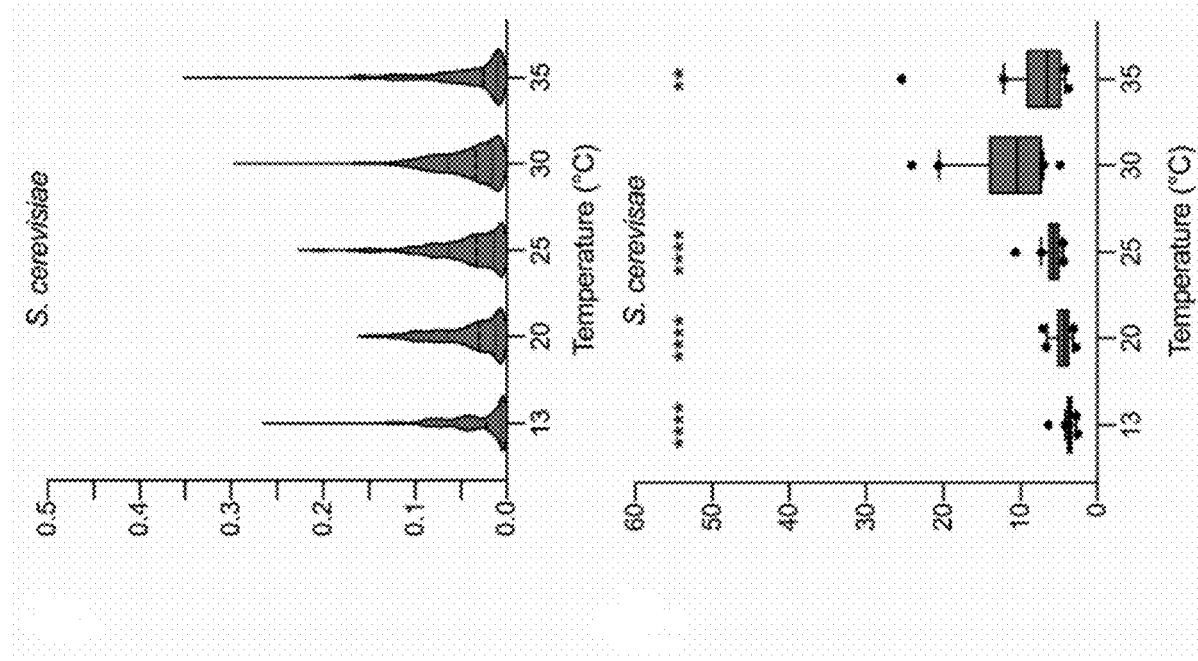
Figure 15A:
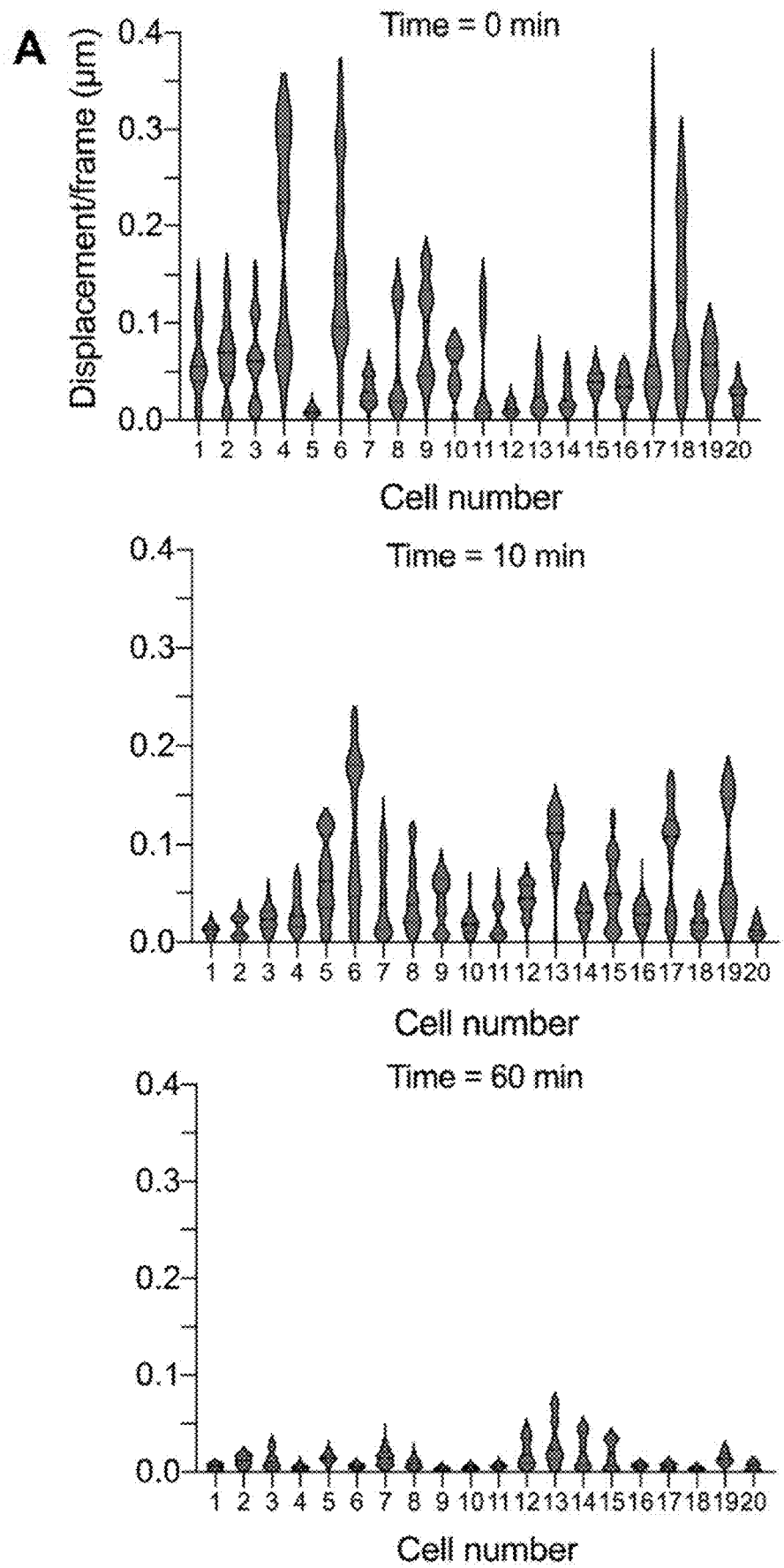
Figure 15B:
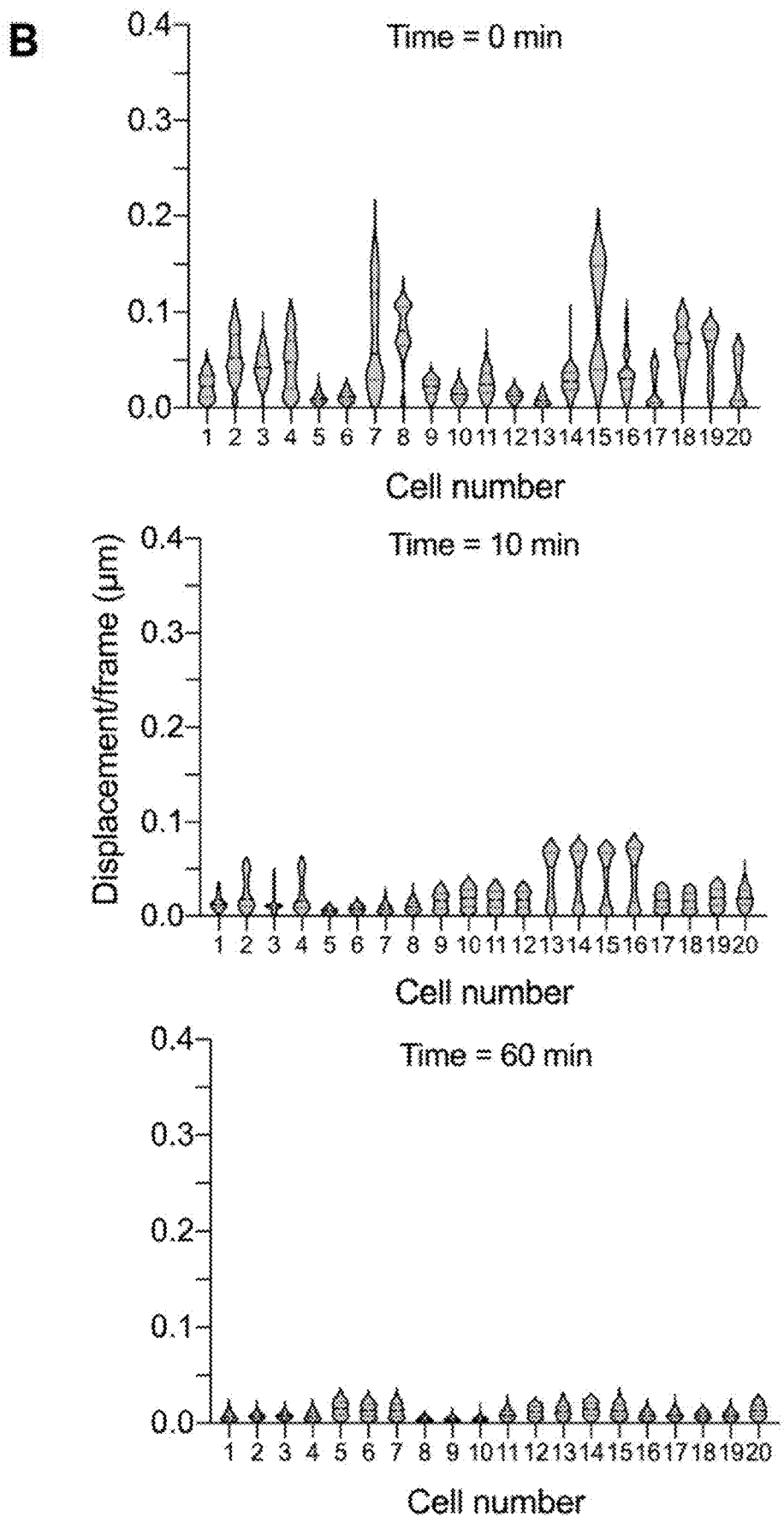
Figure 15C:
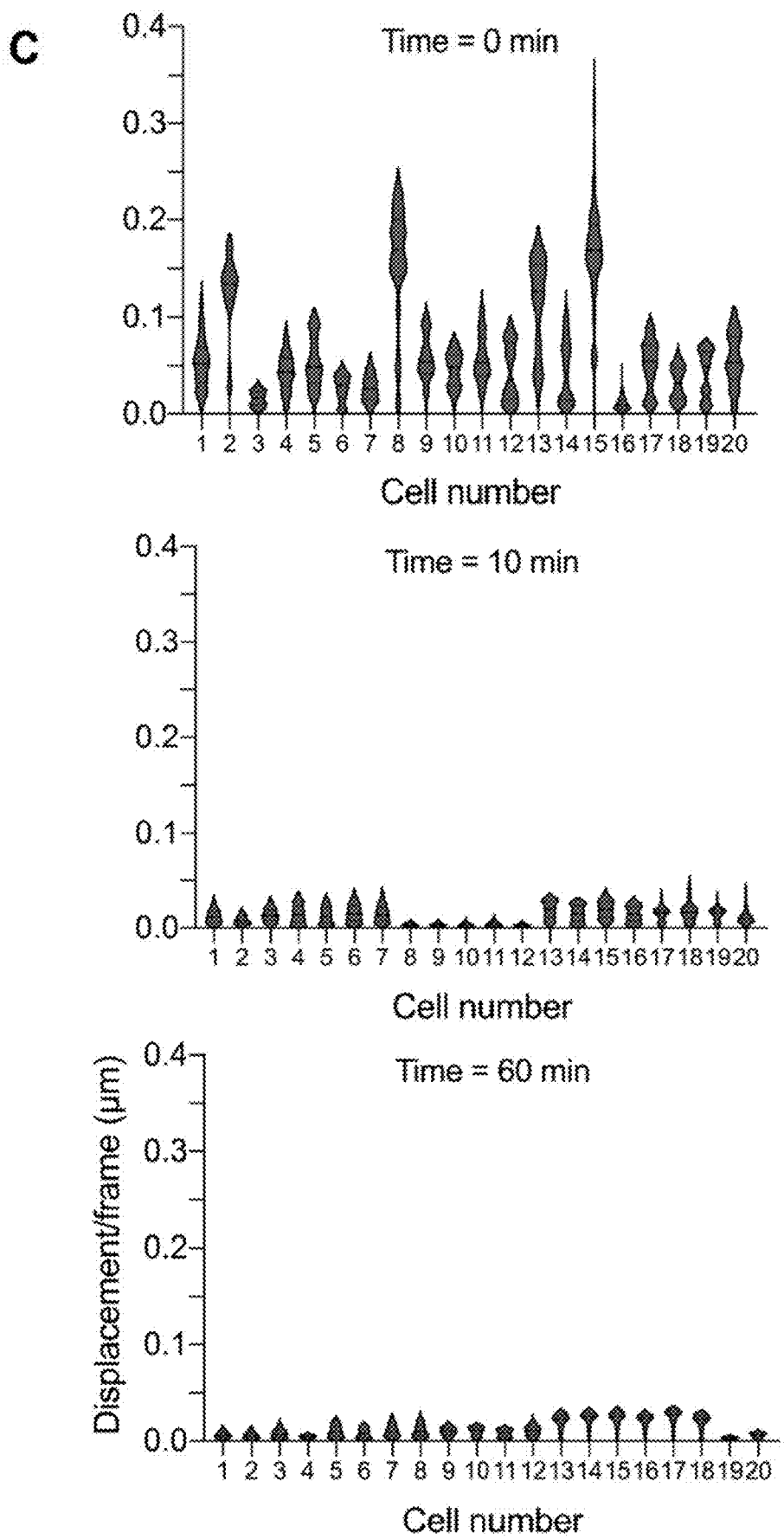
Figure 15D:
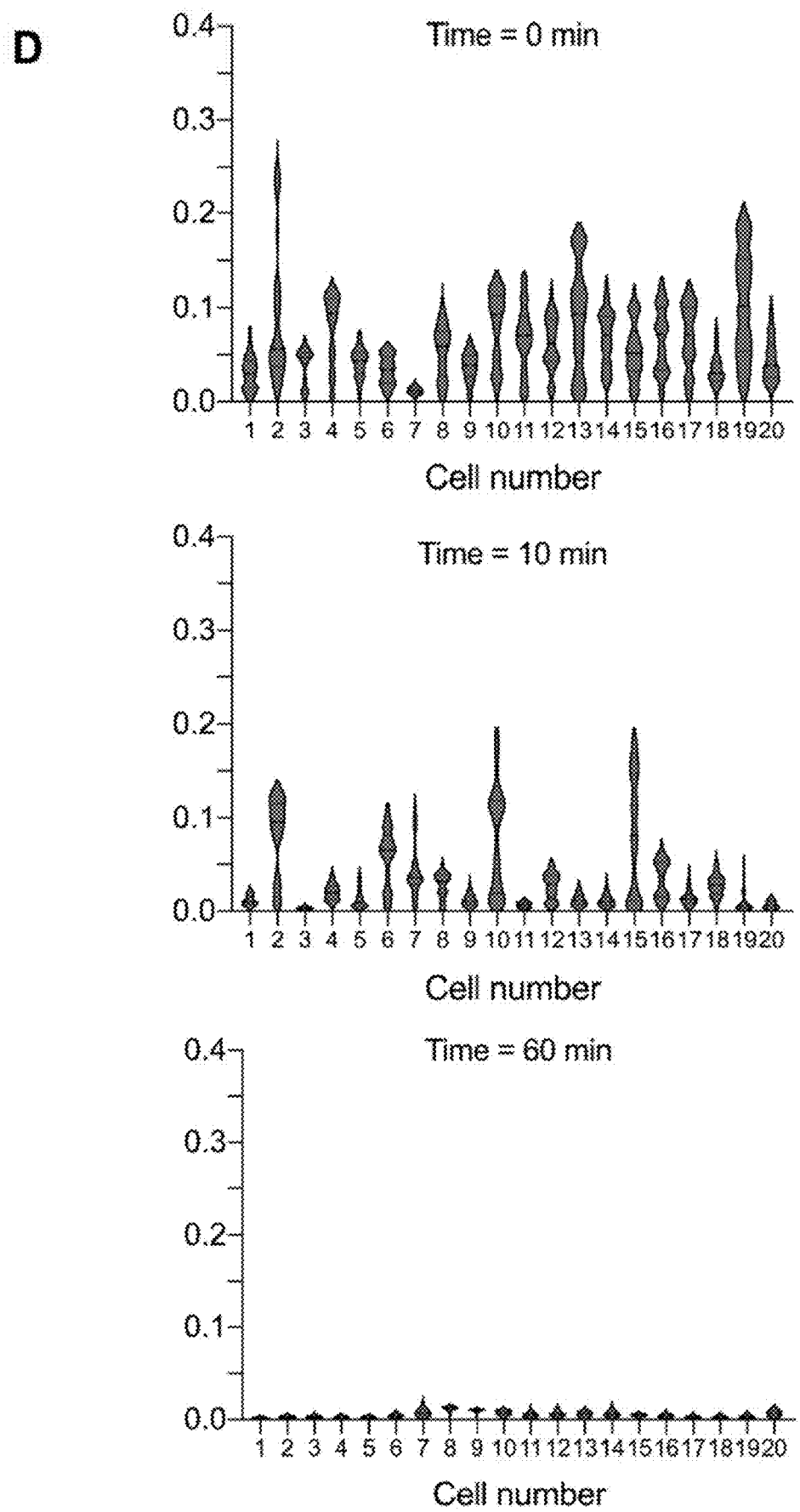
Figure 15E:
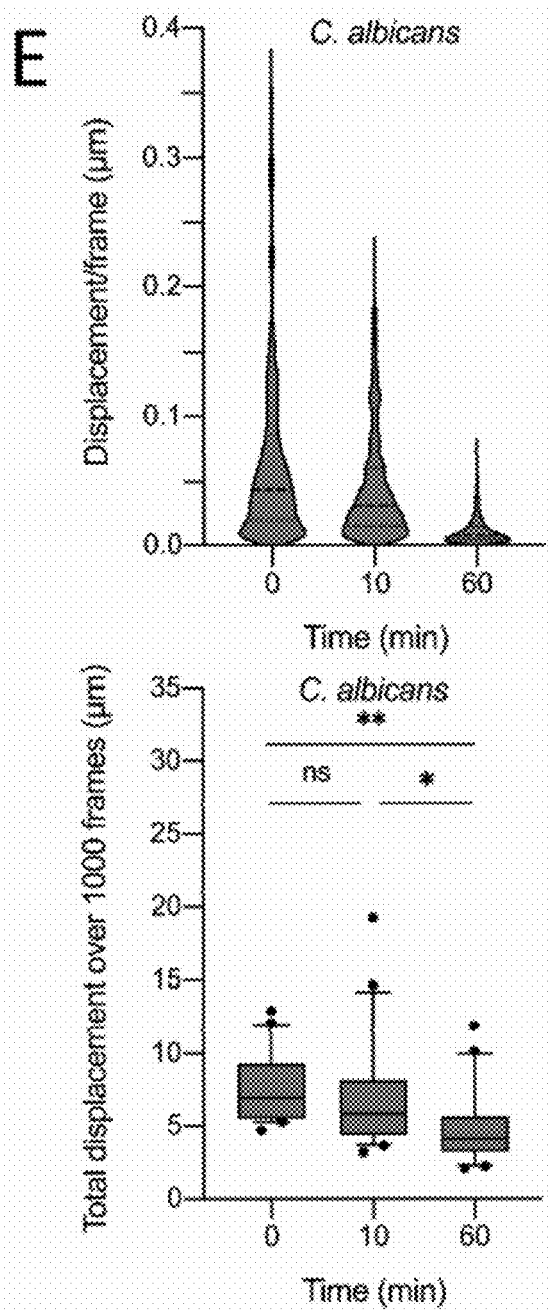
Figure 15F:
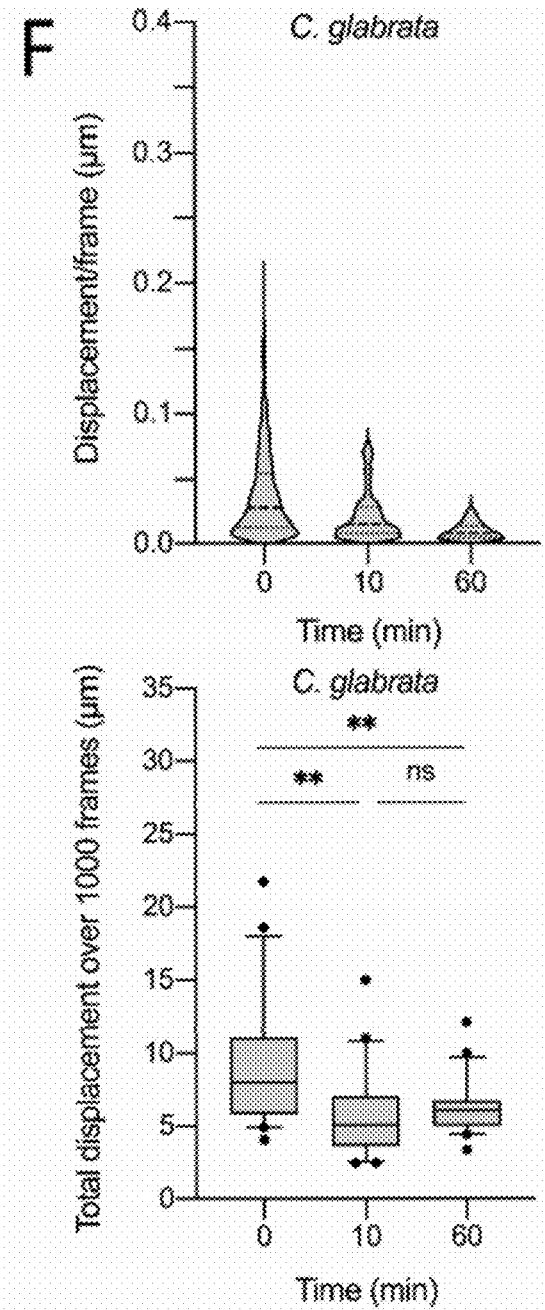
Figures 15G, 15H:
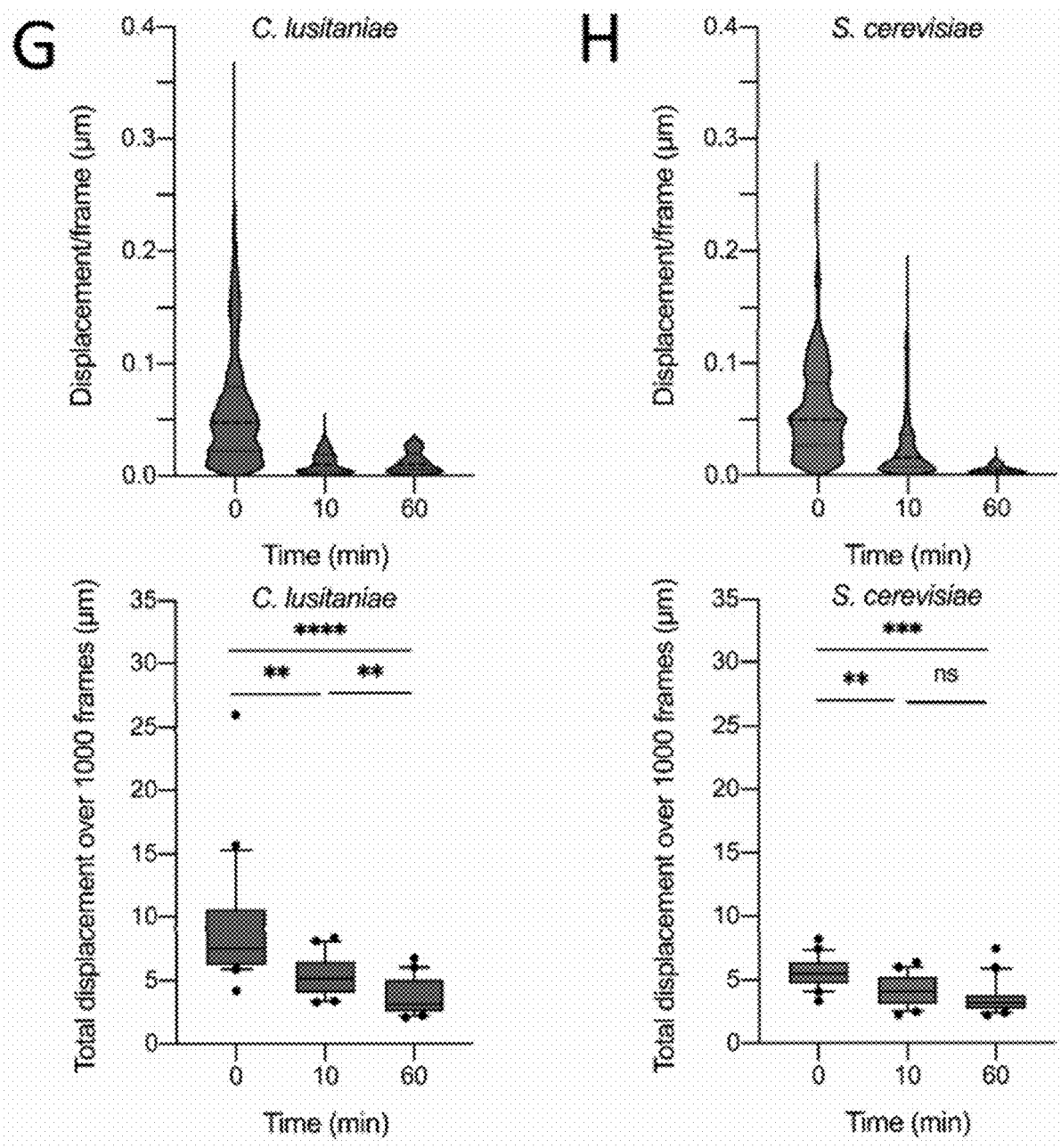
Figure 17A:
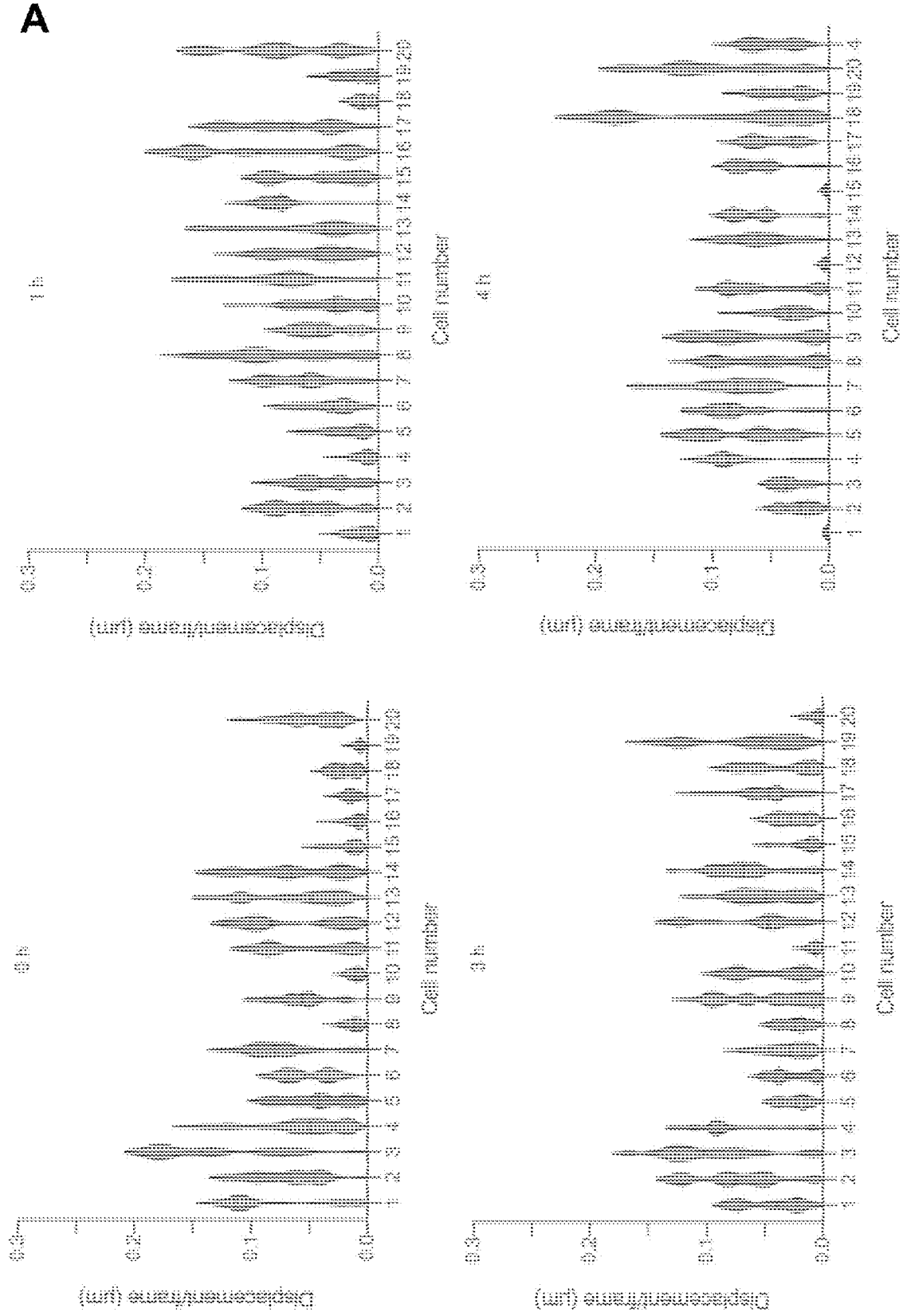
Figure 17B:
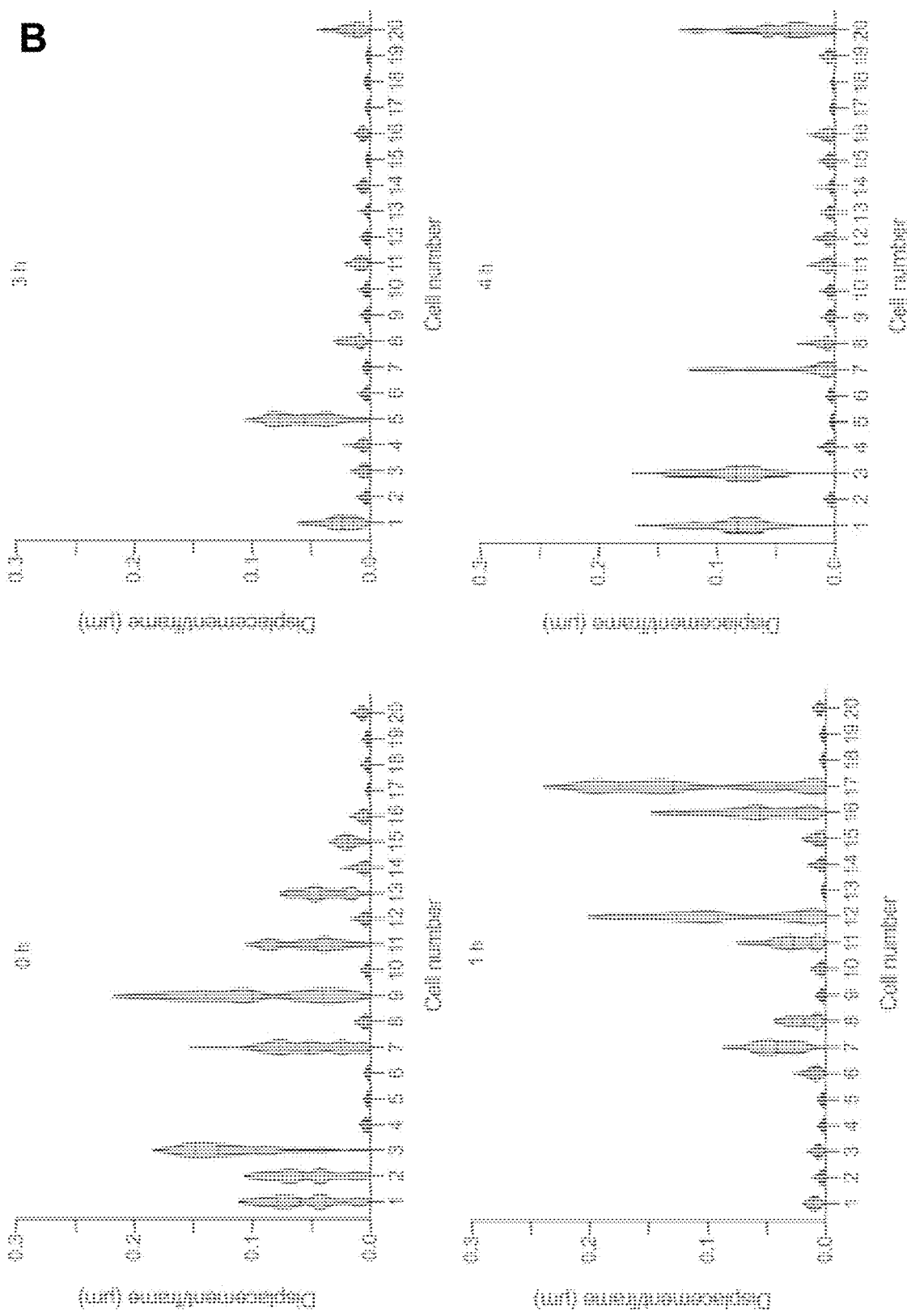
Figure 19A:
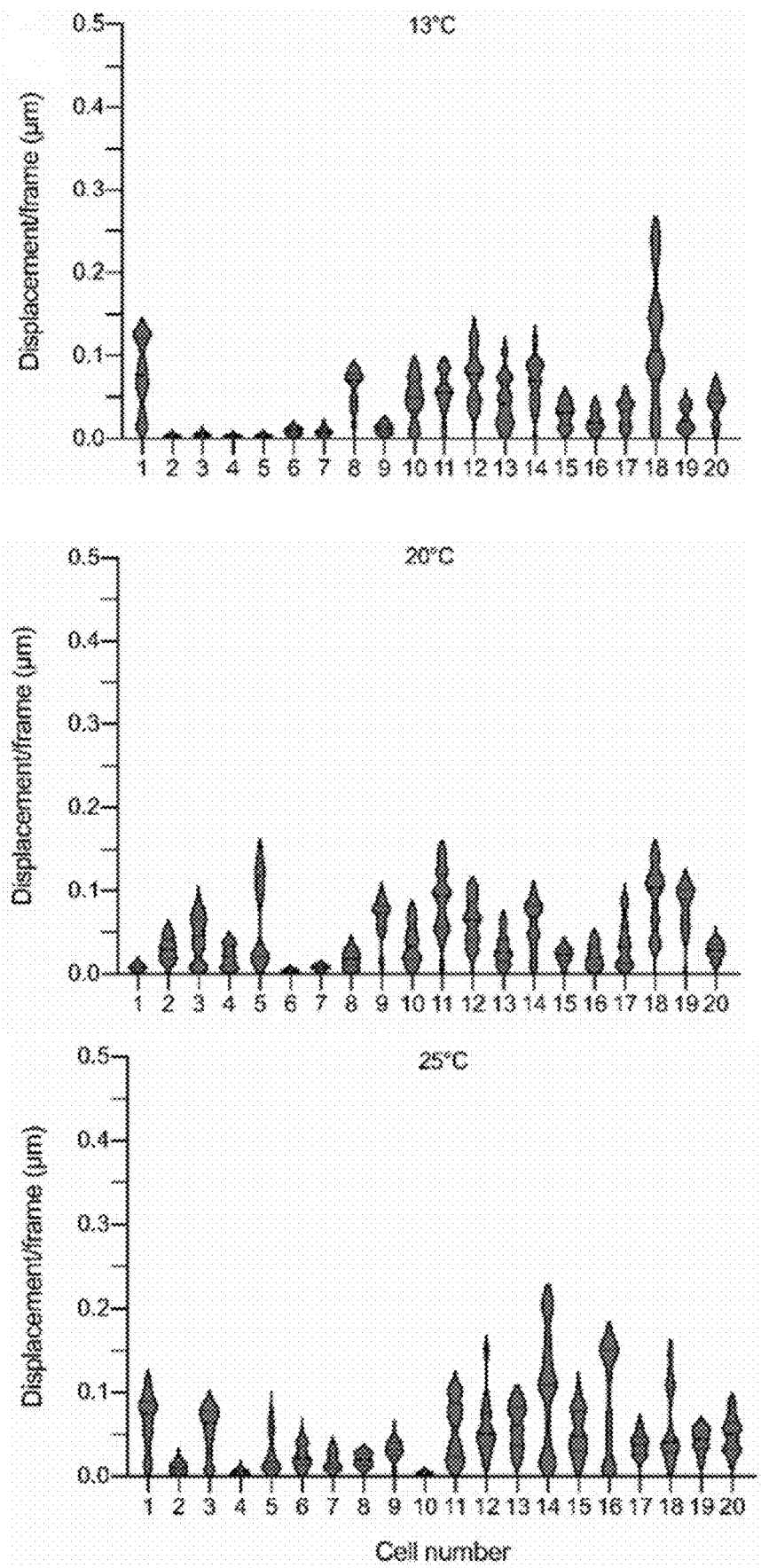
Figure 19C:
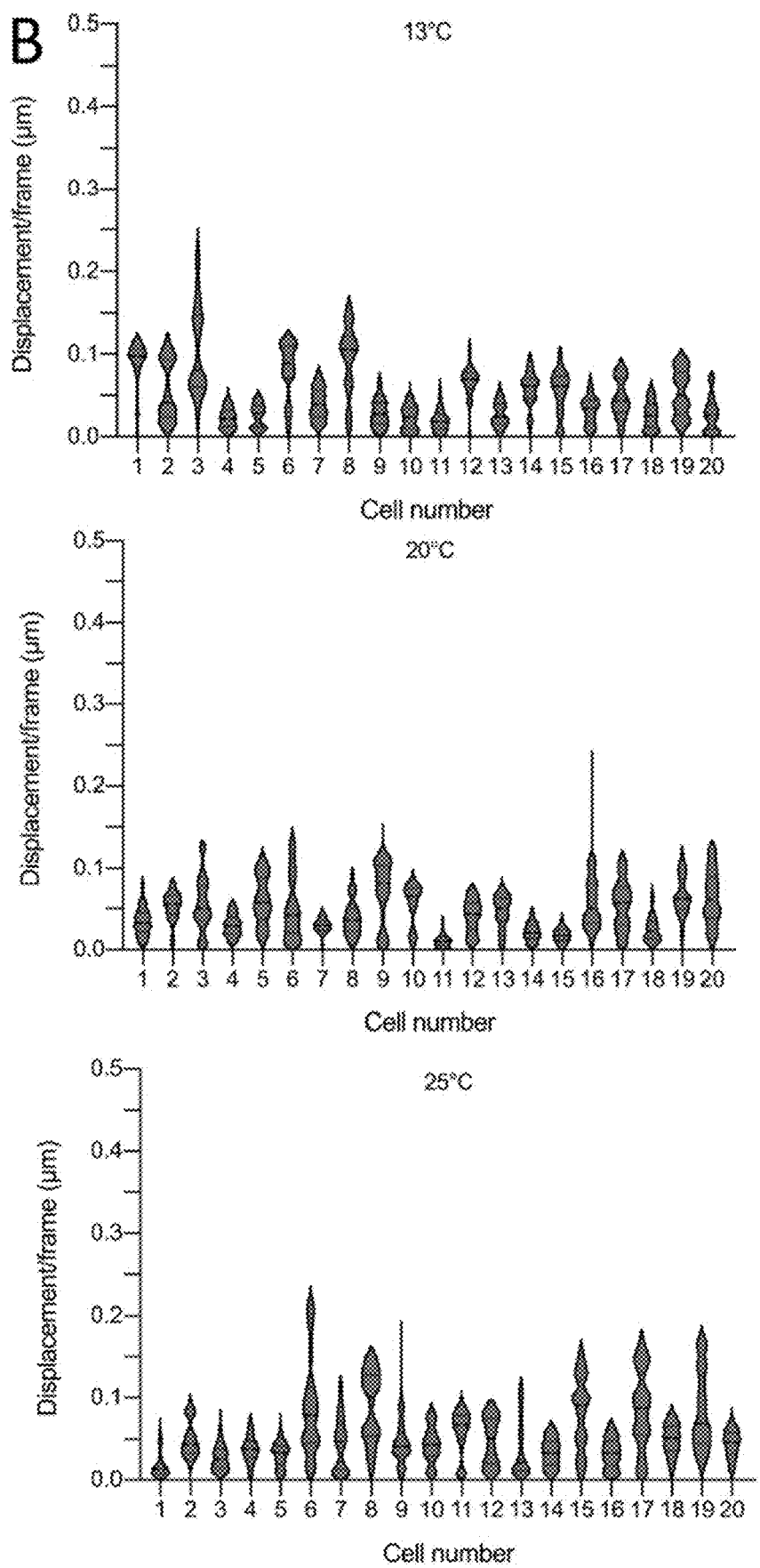
Figure 20B:
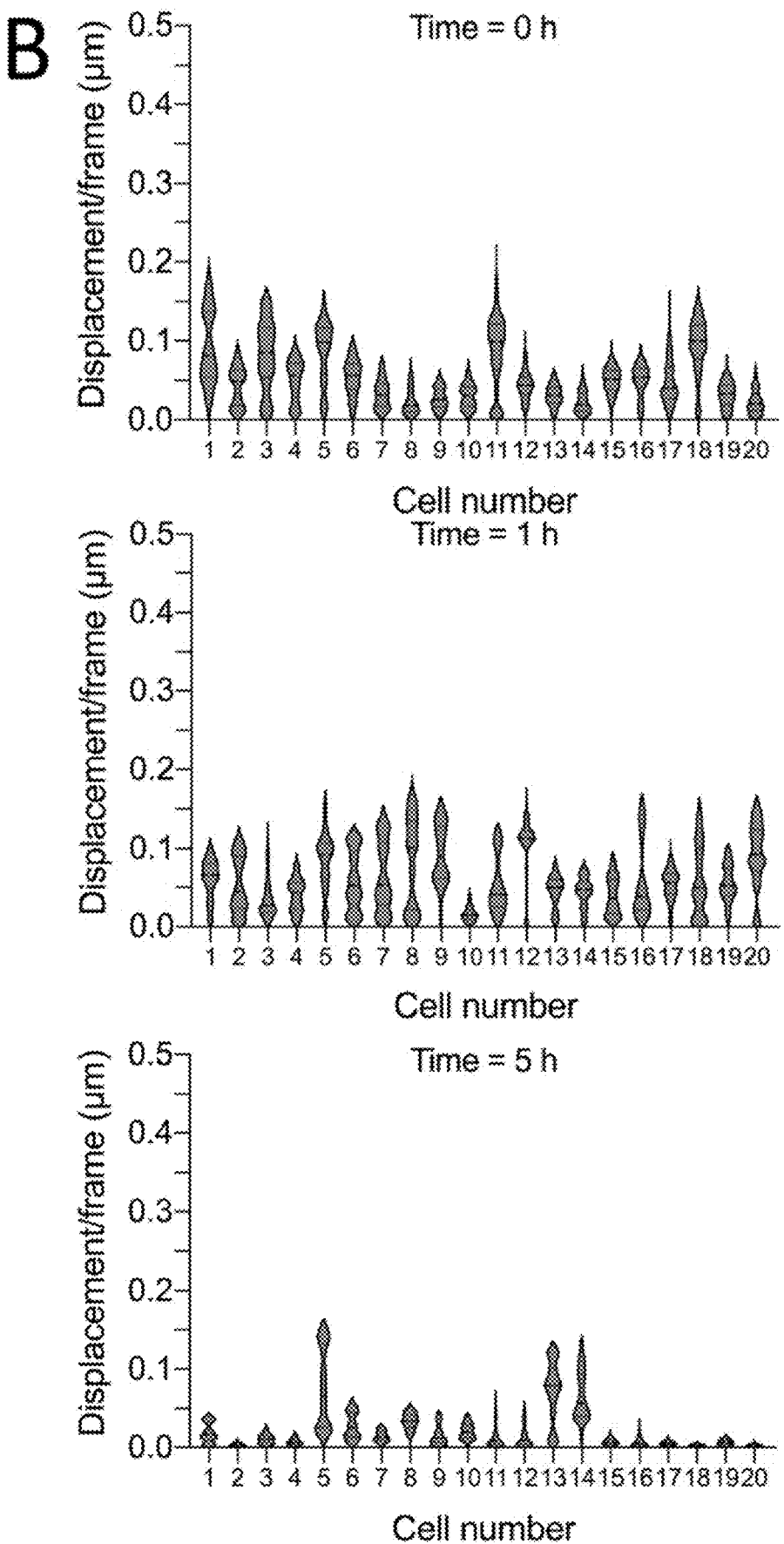
Figure 20C:
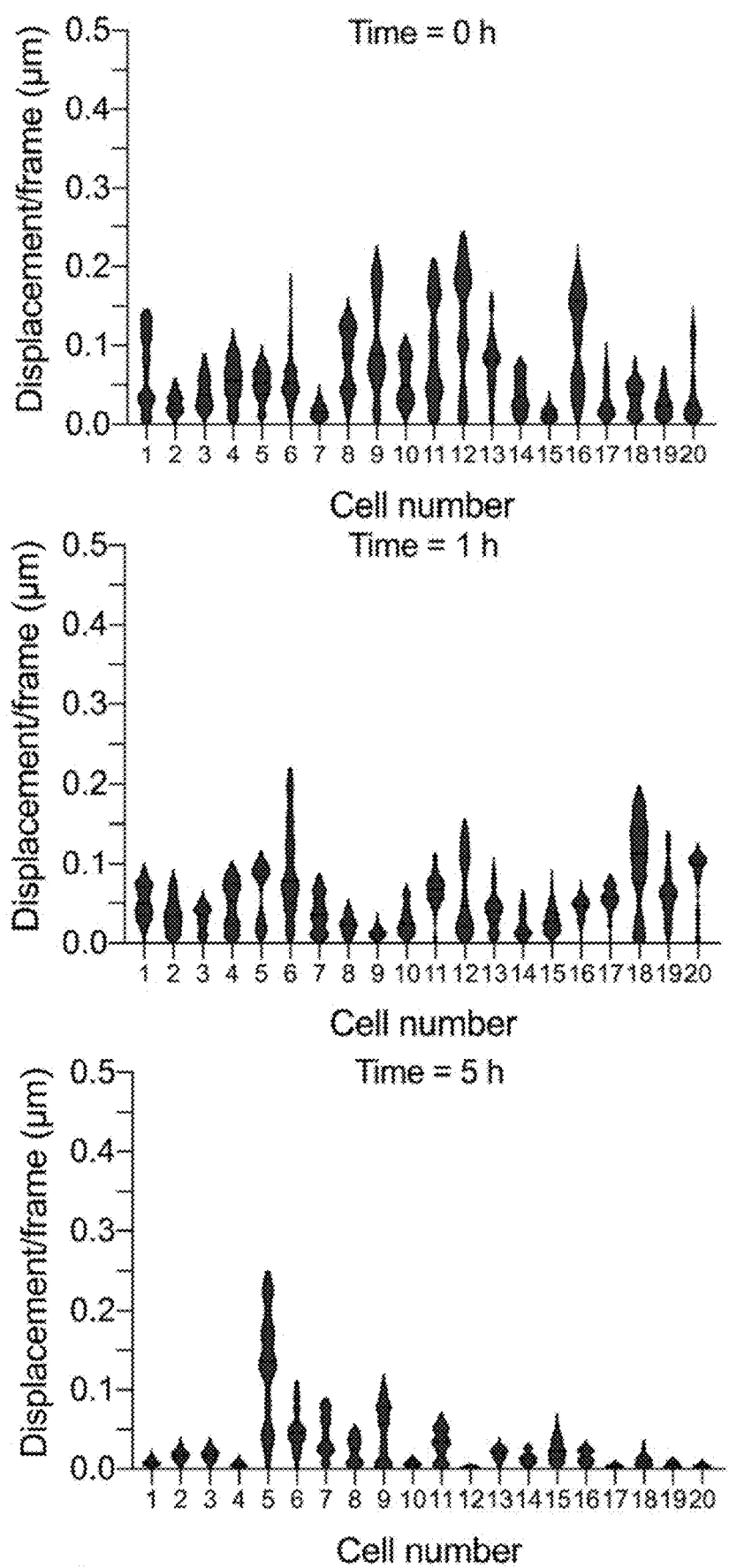
Figure 20D:
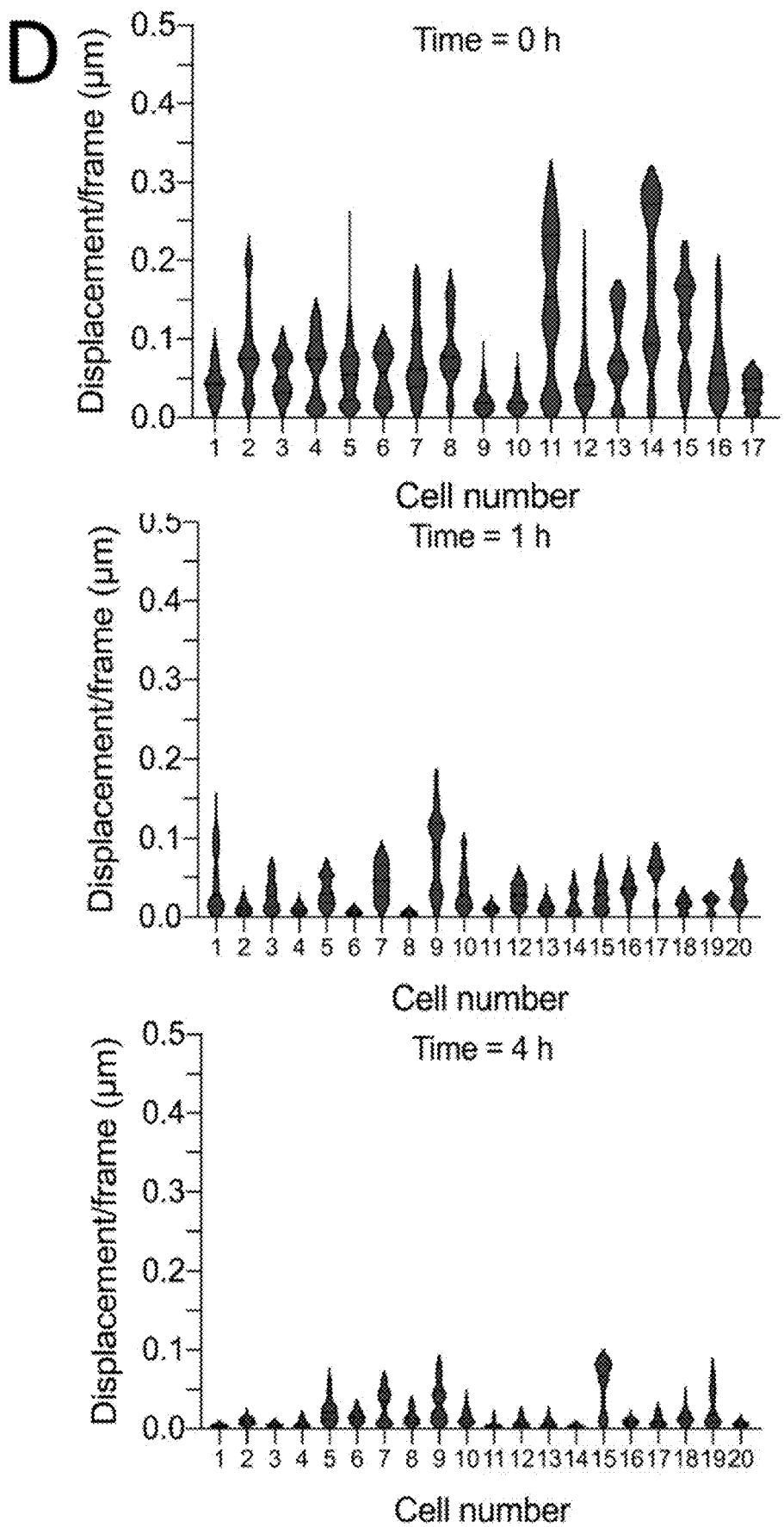
Figure 20E:
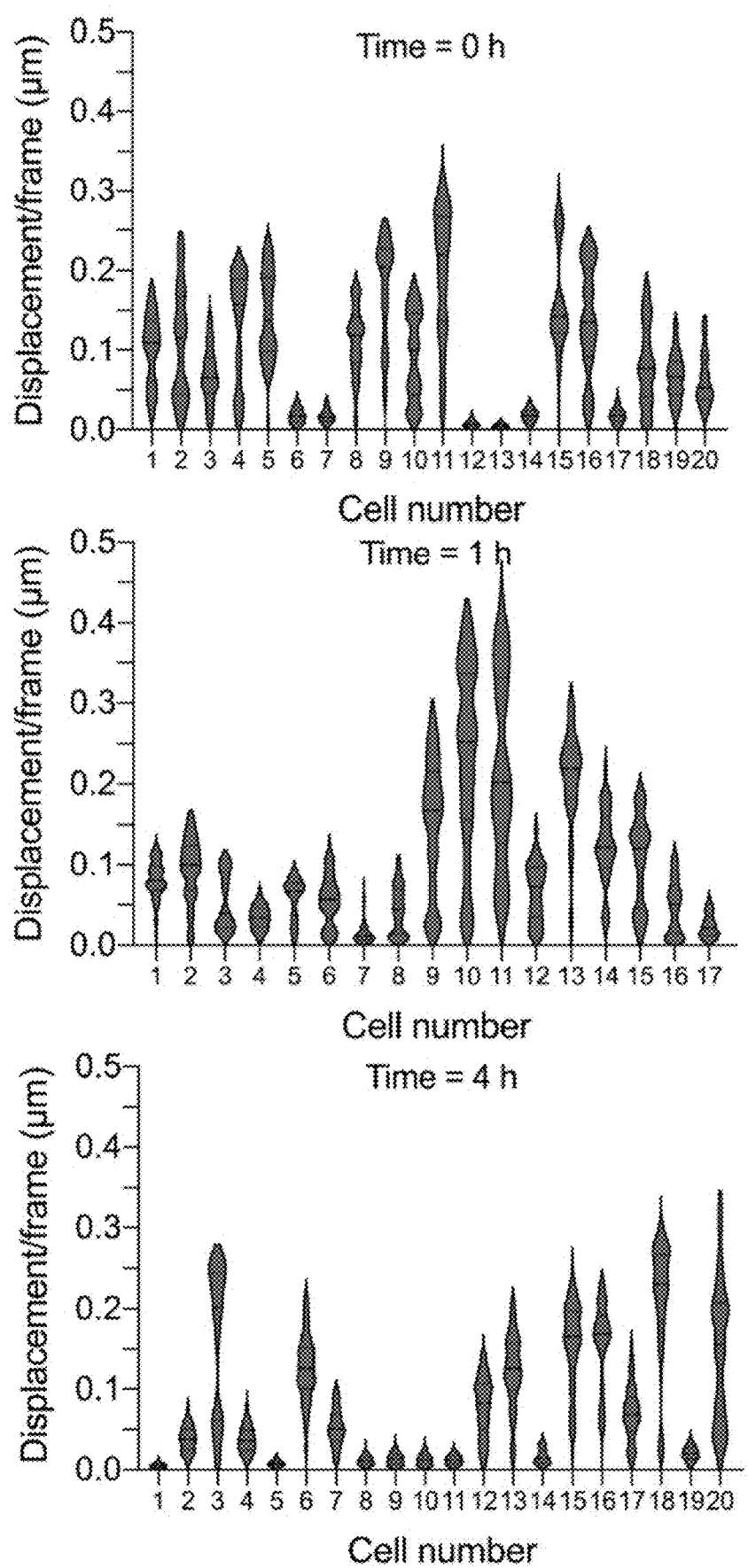
Figure 24:
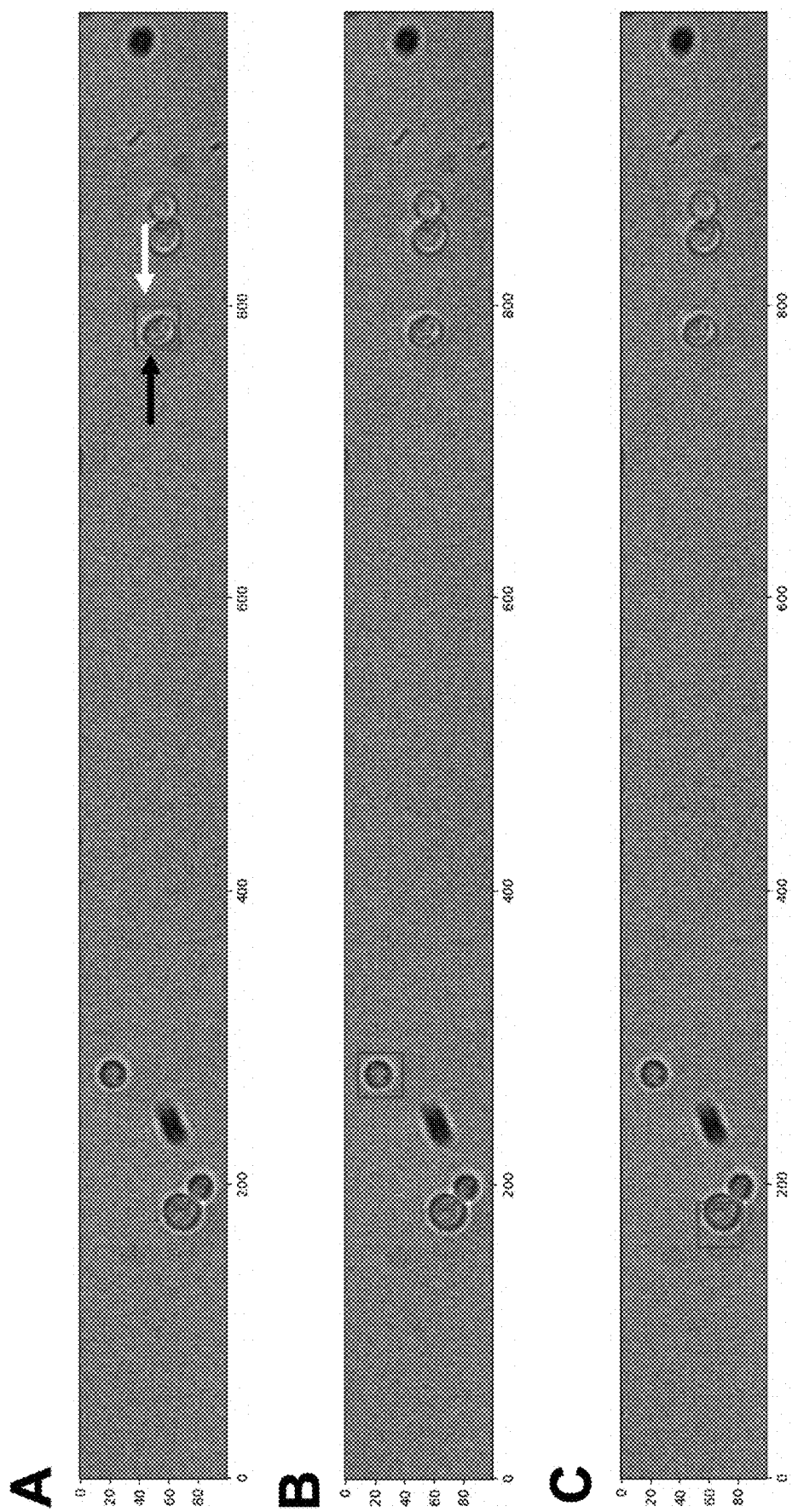

Box plot whiskers within 1.5 IQR of 20 single cells recorded during 12 s; paired Student's t test; **: P<0.0001. *: P<0.001, **: P<0.01, *: P<0.1, ns: not significant;

FIG. 6a-6c shows further supplementary *Candida* results, in particular treatment of *C. albicans* DSY1024 (hypersusceptible). DSY294 (wild type) and DSY4614 (caspofungin resistant) with caspofungin (10 μg/ml) comparing different surface treatments (concanavalin A, untreated glass, and PLL-g-PEG). Box plot whiskers within 1.5 IQR of 20 single cells recorded during 12 s; paired Student's t test; **: P<0.0001, *: P<0.001, **: P<0.01, *: P<0.1, ns: not significant;

FIG. 6d shows further supplementary *Candida* results, in particular treatment of *C. albicans* DSY294, *C. glabrata* DSYS62, *C. lusitaniae* DSY4606 and *S. cerevisiae* BY4742 with ethanol (70% v/v), analysed using longer movies at a lower framerate (1200 frames at 10.5 frames per second). Box plot whiskers within 1.5 IQR of 20 single cells recorded during 12 s; paired Student's t test; **: P<0.0001, *: P<0.001, **: P<0.01, *: P<0.1, ns: not significant;

FIG. 7a shows the determination of the frequency range of cell movements and critical frequency, in particular typical FFT spectra obtained from two optically recorded signals of one *C. albicans* cell movements in the horizontal and vertical directions, as well as their average. Insert: The same FTT spectrum up to 40 Hz;

FIG. 7b shows the determination of the frequency range of cell movements and critical frequency, in particular the determination of the critical frequency via the DRIM method of one typical *S. cerevisiae* BY4742 cell in PBS after 3 h ($f_{crit}$=2.54 Hz);

FIG. 7c shows the determination of the frequency range of cell movements and critical frequency, in particular histograms of $f_{crit}$ for untreated caspofungin resistant DSY4614, sensitive (DSY1024) and wild-type (DSY294 *C. albicans*;

FIG. 7d shows the determination of the frequency range of cell movements and critical frequency, in particular histograms of $f_{crit}$ for caspofungin treated resistant, hypersusceptible and wild-type *C. albicans*. The results are pooled from 1-5-hour treatments;

FIG. 8 shows an exemplary algorithm of a method for characterizing particles according to an embodiment of the present invention with manual selection of the cells;

FIG. 9 shows an exemplary algorithm of a method for characterizing particles according to an embodiment of the present invention with deep learning selection of the cells;

FIG. 10A, 10B show an exemplary algorithm for the training of the detection, as can be used in an embodiment of the present invention;

FIG. 11 shows the effect of antifungals on the nanomotion (average displacement during 12 s measurement) as a function of time using 4 Ibidi microwells. Remark: the antifungal solution was added to the same well at the top and mixing occurred only by diffusion, which increases the time an effect on the viability is observed. Effect of (1) caspofungin on *C. albicans* DSY294 clinical strain (2) amphotericin B on *C. albicans* DSY294, (3) fluconazole on *C. albicans* DSY294 and (4) *S. cerevisiae* BY4741. Error bars represent the standard deviation from the displacement of 20 single cells recorded during 12 s: paired Student's t test * P<0.001; ** P<0.01). B. Effect of the temperature on the average displacement for *S. cerevisiae* BY4741, the clinical strains *C. albicans* DSY294 and *C. lusitaniae* DSY4606. Fifteen minutes after the temperature was stabilised after a step increase of the temperature, the movement of 20 single cells per condition was recorded during ~12 s and analysed;

FIG. 12 shows movement for *Candide albicans*: wild type, sensitive and resistant strains; and *S. cerevisiae* BY4742. The effect of Caspofungin during 5 h incubation. Caspofungin concentration in YPD medium is 10 μg/l;

FIG. 13a shows a time period of cells in growth medium followed by an antifungal treatment;

FIG. 13b shows at movies recorded of 1000 frames at different time points;

FIG. 13c shows the X, Y displacements of individual cells (typically 20 cells) being calculated using the cross-correlation algorithm;

FIG. 13d shows for each cell, the displacement per frame is calculated and this distribution is represented by a combined violin and box plot:

FIG. 13e shows the displacement per frame for all cells for a condition/sampling point being represented as a combined violin plot and box plot:

FIG. 13f shows the mean of the total displacements of 20 cells being calculated for each condition/sampling point and represented in a box plot;

FIG. 14a shows the distribution of the displacements per frame of 20 *S. cerevisiae* BY4742 cells growing in YPD growth medium after 2 h (upper panel) and the time evolution of the merged distributions of the displacements for 20 cells (lower panel);

FIG. 14b shows the distribution of the displacements per frame of 20 *S. cerevisiae* BY4742 cells present in PBS after 2 h (upper panel) and the time evolution of the merged distributions of the displacements for 20 cells (lower panel);

FIG. 14c shows the time evolution of grouped displacements in growth medium. Effect of the temperature on the displacement distribution (20 cells) for *S. cerevisiae* BY4742 and *C. albicans* DSY294:

FIG. 14d shows the effect of the temperature on the total displacement of *S. cerevisiae* BY4742 and *C. albicans* DSY294. Wilcoxon test: **P<0.0001, *P<0.001, **P<0.01, ns: not significant:

FIG. 15a shows the life-dead transition by observing cellular nanomotions of yeast cells in the presence of ethanol, in particular the distribution of the displacements of 20 cells at time 0 min (upper panel), 10 min (middle panel) and 60 min (lower panel) for *C. albicans* DSY294;

FIG. 15b shows the life-dead transition by observing cellular nanomotions of yeast cells in the presence of ethanol, in particular the distribution of the displacements of 20 cells at time 0 min (upper panel), 10 min (middle panel) and 60 min (lower panel) for *C. glabrata* DSY562;

FIG. 15c shows the life-dead transition by observing cellular nanomotions of yeast cells in the presence of ethanol, in particular the distribution of the displacements of 20 cells at time 0 min (upper panel), 10 min (middle panel) and 60 min (lower panel) for *C. lusitanise* DSY4606;

FIG. 15d shows the life-dead transition by observing cellular nanomotions of yeast cells in the presence of ethanol, in particular the distribution of the displacements of 20 cells at time 0 min (upper panel), 10 min (middle panel) and 60 min (lower panel) for *S. cerevisiae* BY4742;

FIG. 15e shows the life-dead transition by observing cellular nanomotions of yeast cells in the presence of ethanol, in particular the time evolution of displacements/frame per frame of 20 cells (upper panel) and the corresponding graphs of the total displacement during 12 s measurement as a function of time (lower panels). Wilcoxon test: ** P<0.0001; * P<0.001; ** P<0.01; * P<0.1; ns: not significant for *C. albicans* DSY294;

FIG. 15f shows the life-dead transition by observing cellular nanomotions of yeast cells in the presence of ethanol, in particular the time evolution of displacements/ frame per frame of 20 cells (upper panel) and the corresponding graphs of the total displacement during 12 s measurement as a function of time (lower panels). Wilcoxon test: ** P<0.0001; * P<0.001; ** P<0.01; * P<0.1; ns: not significant for C. glabrata DSY562:

FIG. 15g shows the life-dead transition by observing cellular nanomotions of yeast cells in the presence of ethanol, in particular the time evolution of displacements/ frame per frame of 20 cells (upper panel) and the corresponding graphs of the total displacement during 12 s measurement as a function of time (lower panels). Wilcoxon test: ** P<0.0001; * P<0.001; ** P<0.01; * P<0.1; ns: not significant for C. lusitaniae DSY4606;

FIG. 15h shows life-dead transition by observing cellular nanomotions of yeast cells in the presence of ethanol, in particular the time evolution of displacements/frame per frame of 20 cells (upper panel) and the corresponding graphs of the total displacement during 12 s measurement as a function of time (lower panels). Wilcoxon test: ** P<0.0001; * P<0.001; ** P<0.01; * P<0.1; ns: not significant for S. cerevisiae BY4742:

FIG. 16a shows the effect of the antifungal amphotericin B (500 µg/ml) on the cellular nanomotion of C. albicans DSY294, in particular the time evolution of displacement distributions of 20 cells of (upper panel) and the corresponding graphs of the total displacement during 12 s (lower panel):

FIG. 16b shows the effect of the antifungal caspofungin (100 µg/ml) on the cellular nanomotion of C. albicans DSY294, in particular the time evolution of displacement distributions of 20 cells of (upper panel) and the corresponding graphs of the total displacement during 12 s (lower panel);

FIG. 16c shows the effect of the antifungal fluconazole (400 µg/ml) on the cellular nanomotion of C. albicans DSY294, in particular the time evolution of displacement distributions of 20 cells of (upper panel) and the corresponding graphs of the total displacement during 12 s (lower panel);

FIG. 16d shows the effect of the antifungal caspofungin (10 µg/ml) on the cellular nanomotion of the hypersusceptible C. albicans DSY1024, in particular the time evolution of displacement distributions of 20 cells of (upper panel) and the corresponding graphs of the total displacement (lower panel);

FIG. 16e shows the effect of the antifungal caspofungin (10 µg/ml) on the cellular nanomotion of the candin-resistant C. albicans DSY4614, in particular the time evolution of displacement distributions of 20 cells of (upper panel) and the corresponding graphs of the total displacement (lower panel);

FIG. 16f shows the effect of increasing amphotencin B concentrations on C. albicans DSY294, in particular cellular displacements (left panel) and the total displacement for 20 cells (right panel) after 1 h treatment, with the Wilcoxon test: ** P<0.0001; * P<0.001; ** P<0.01; * P<0.1; ns: not significant;

FIG. 16g shows the effect of increasing amphotericin B concentrations on C. albicans DSY294, in particular cellular displacements (left panel) and the total displacement for 20 cells (right panel) after 2 h treatment, with the Wilcoxon test: ** P<0.0001; * P<0.001; ** P<0.01; * P<0.1: ns: not significant;

FIG. 17a shows the effect of the nutritional environment on the cellular nanomotions of yeast cells, in particular the distribution of the displacements per frame of 20 S. cerevisiae BY4742 cells growing in YPD growth medium;

FIG. 17b shows the effect of the nutritional environment on the cellular nanomotions of yeast cells, in particular the distribution of the displacements per frame of 20 S. cerevisiae BY4742 cells present in PBS;

FIG. 17c shows the effect of the nutritional environment on the cellular nanomotions of yeast cells, in particular the time evolution of the total displacement during 12 s measurement as a function of time for cells (C) in YPD growth medium, with Wilcoxon test: **** P<0.0001; * P<0.1; ns: not significant:

FIG. 17d shows the effect of the nutritional environment on the cellular nanomotions of yeast cells, in particular the time evolution of the total displacement during 12 s measurement as a function of time for cells in PBS, with Wilcoxon test: **** P<0.0001; * P<0.1; ns: not significant;

FIG. 18a shows movements of silica microbeads and adhesion of cells to the glass surface by concanavalin A. A, in particular the displacement/frame for 20 beads on a glass surface;

FIG. 18b shows movements of silica microbeads and adhesion of cells to the glass surface by concanavalin A. A, in particular the displacement/frame for 20 beads on a PLL-PEG treated surface;

FIG. 18c shows movements of silica microbeads and adhesion of cells to the glass surface by concanavalin A. A, in particular the displacements per frame of all 20 beads on a glass and PLL-PEG treated surface;

FIG. 18d shows movements of silica microbeads and adhesion of cells to the glass surface by concanavalin A. A, in particular the total displacement during 12 s measurement of beads on a glass and PLL-PEG treated surface, with the Wilcoxon test: **** P<0.0001;

FIG. 18f shows movements of silica microbeads and adhesion of cells to the glass surface by concanavalin A. A in particular the displacement/frame of 20 cells untreated (upper) and caspofungin (10 µg/ml) treated cells after 5 h (lower panel) for the wild-type C. albicans DSY294;

FIG. 18g shows movements of silica microbeads and adhesion of cells to the glass surface by concanavalin A. A, in particular the displacement/frame of 20 cells untreated (upper panel) and caspofungin (10 µg/ml) treated cells after 5 h (lower panel) for the hypersusceptible C. albicans DSY1024 strain;

FIG. 18h shows movements of silica microbeads and adhesion of cells to the glass surface by concanavalin A, A, in particular the displacements per frame of all 20 C. albicans DSY294;

FIG. 18i shows movements of silica microbeads and adhesion of cells to the glass surface by concanavalin A. A, in particular the displacements per frame of all 20 C. albicans DSY1024 cells;

FIG. 18j shows movements of silica microbeads and adhesion of cells to the glass surface by concanavalin A. A, in particular the total displacement during 12 s measurement of 20 (H) C. albicans DSY294;

FIG. 18k shows movements of silica microbeads and adhesion of cells to the glass surface by concanavalin A. A, in particular the total displacement during 12 s measurement of 20 (K) C. albicans DSY1024 cells;

FIG. 19a shows the effect of the temperature on the cellular nanomotions of yeast cells, in particular the distribution of the displacements per frame of 20 cells as function of the temperature (13*C, 20° C., 25° C.) for S. cerevisiae BY4742;

FIG. 19b shows the effect of the temperature on the cellular nanomotions of yeast cells, in particular the distribution of the displacements per frame of 20 cells as function of the temperature (30° C., 35° C.) for S. cerevisiae BY4742;

FIG. 19c shows the effect of the temperature on the cellular nanomotions of yeast cells, in particular the distribution of the displacements per frame of 20 cells as function of the temperature (13° C., 20° C., 25° C.) for C. albicans DSY294;

FIG. 19d shows the effect of the temperature on the cellular nanomotions of yeast cells, in particular the distribution of the displacements per frame of 20 cells as function of the temperature (30° C., 35° C.) for C. albicans DSY294;

FIG. 20a shows the effect of antifungals on the cellular nanomotion of C. albicans. The displacement/frame of 20 C. albicans DSY294 cells treated with amphotericin B (500 µg/ml);

FIG. 20b shows the effect of antifungals on the cellular nanomotion of C. albicans. The displacement/frame of 20 C. albicans DSY294 cells treated with caspofungin (100 µg/ml);

FIG. 20c shows the effect of antifungals on the cellular nanomotion of C. albicans. The displacement/frame of 20 C. albicans DSY294 cells treated with fluconazole (400 µg/ml);

FIG. 20d shows the displacement/frame of 20 (D) hyper-susceptible C. albicans DSY1024 cells;

FIG. 20e shows the displacement/frame of 20 (D) hyper-susceptible C. albicans DSY1024 cells (E) the candin-resistant C. albicans DSY4614 cells treated with caspofungin (10 µg/ml);

FIG. 21a shows the effect of increasing amphotericin 8 concentrations on C. albicans DSY294 wildtype strain, in particular cellular displacements per frame after 1 h for untreated cells;

FIG. 21b shows the effect of increasing amphotencin B concentrations on C. albicans DSY294 wild-type strain, in particular cellular displacements per frame after 1 h for 0.1 µg/ml;

FIG. 21c shows the effect of increasing amphotericin 8 concentrations on C. albicans DSY294 wild-type strain, in particular cellular displacements per frame after 1 h for 0.5 µg/ml;

FIG. 21d shows the effect of increasing amphotericin B concentrations on C. albicans DSY294 wild-type strain, in particular cellular displacements per frame after 1 h for 10 µg/ml;

FIG. 21e shows the effect of increasing amphotericin 8 concentrations on C. albicans DSY294 wild-type strain, in particular cellular displacements per frame after 1 h for 4 µg/ml;

FIG. 21f shows the effect of increasing amphotericin B concentrations on C. albicans DSY294 wild-type strain, in particular cellular displacements per frame after 1 h for 10 µg/ml;

FIG. 21g shows the effect of increasing amphotericin B concentrations on C. albicans DSY294 wild-type strain, in particular cellular displacements per frame after 1 h for 50 µg/ml;

FIG. 21h shows the effect of increasing amphotericin B concentrations on C. albicans DSY294 wildtype strain, in particular cellular displacements per frame after 1 h for 100 µg/ml;

FIG. 21i shows the effect of increasing amphotericin B concentrations on C. albicans DSY294 wild-type strain, in particular cellular displacements per frame after 2 h for untreated cells;

FIG. 21j shows the effect of increasing amphotencin B concentrations on C. albicans DSY294 wild-type strain, in particular cellular displacements per frame after 2 h for 0.1 µg/ml;

FIG. 21k shows the effect of increasing amphotericin 8 concentrations on C. albicans DSY294 wild-type strain, in particular cellular displacements per frame after 2 h for 0.5 µg/ml:

FIG. 21l shows the effect of increasing amphotericin B concentrations on C. albicans DSY294 wild-type strain, in particular cellular displacements per frame after 2 h for 1 µg/ml;

FIG. 21m shows the effect of increasing amphotericin B concentrations on C. albicans DSY294 wild-type strain, in particular cellular displacements per frame after 2 h for 4 µg/ml;

FIG. 21n shows the effect of increasing amphotencin B concentrations on C. albicans DSY294 wild-type strain, in particular cellular displacements per frame after 2 h for 10 µg/ml:

FIG. 21o shows the effect of increasing amphotericin B concentrations on C. albicans DSY294 wild-type strain, in particular cellular displacements per frame after 2 h for 50 µg/ml;

FIG. 21p shows the effect of increasing amphotericin B concentrations on C. albicans DSY294 wild-type strain, in particular cellular displacements per frame after 2 h for 100 µg/ml;

FIG. 22a shows the effect of increasing amphotericin B concentrations on C. albicans CAF2-1 wild-type strain, in particular the cellular displacements per frame after 1 h for untreated cells;

FIG. 22b shows the effect of increasing amphotericin B concentrations on C. albicans CAF2-1 wild-type strain, in particular the cellular displacements per frame after 1 h for 0.1 µg/ml;

FIG. 22c shows the effect of increasing amphotericin B concentrations on C. albicans CAF2-1 wild-type strain, in particular the cellular displacements per frame after 1 h for 0.5 µg/ml;

FIG. 22d shows the effect of increasing amphotericin 8 concentrations on C. albicans CAF2-1 wild-type strain, in particular the cellular displacements per frame after 1 h for 1 µg/ml;

FIG. 22e shows the effect of increasing amphotericin B concentrations on C. albicans CAF2-1 wild-type strain, in particular the cellular displacements per frame after 1 h for 4 µg/ml;

FIG. 22f shows the effect of increasing amphotericin 8 concentrations on C. albicans CAF2-1 wild-type strain, in particular the cellular displacements per frame after 1 h for 10 µg/ml;

FIG. 22g shows the effect of increasing amphotericin 8 concentrations on C. albicans CAF2-1 wild-type strain, in particular the cellular displacements per frame after 1 h for 50 µg/ml;

FIG. 22h shows the effect of increasing amphotericin B concentrations on C. albicans CAF2-1 wild-type strain, in particular the cellular displacements per frame after 1 h for 100 µg/ml;

FIG. 22i shows the effect of increasing amphotericin B concentrations on C. albicans CAF2-1 wild-type strain, in particular the cellular displacements per frame after 2 h for untreated cells;

FIG. 22*j* shows the effect of increasing amphotencin B concentrations on *C. albicans* CAF2-1 wild-type strain, in particular the cellular displacements per frame after 2 h for 0.1 µg/ml;

FIG. 22*k* shows the effect of increasing amphotericin 8 concentrations on *C. albicans* CAF2-1 wild-type strain, in particular the cellular displacements per frame after 2 h for 0.5 µg/ml;

FIG. 22*l* shows the effect of increasing amphotericin B concentrations on *C. albicans* CAF2-1 wild-type strain, in particular the cellular displacements per frame after 2 h for 1 µg/ml;

FIG. 22*m* shows the effect of increasing amphotericin 8 concentrations on *C. albicans* CAF2-1 wild-type strain, in particular the cellular displacements per frame after 2 h for 4 µg/ml;

FIG. 22*n* shows the effect of increasing amphotericin B concentrations on *C. albicans* CAF2-1 wild-type strain, in particular the cellular displacements per frame after 2 h for 10 µg/ml;

FIG. 22*o* shows the effect of increasing amphotericin B concentrations on *C. albicans* CAF2-1 wild-type strain, in particular the cellular displacements per frame after 2 h for 50 µg/ml;

FIG. 22*p* shows the effect of increasing amphotericin B concentrations on *C. albicans* CAF2-1 wild-type strain, in particular the cellular displacements per frame after 2 h for 100 µg/ml;

FIG. 22*q* shows cellular displacements per frame (left panel) and the total displacement per frame for 20 cells (right panel) after 1 h treatment, with the Wilcoxon test: **** $P<0.0001$; * $P<0.1$; ns: not significant;

FIG. 22*r* shows cellular displacements per frame (left panel) and the total displacement per frame for 20 cells (right panel) after 2 h treatment, with the Wilcoxon test: **** $P<0.0001$: * $P<0.1$; ns: not significant;

FIG. 23*a* shows the effect of the surface on cellular movement of *C. albicans*, in particular the displacement/frame of 20 *C. albicans* DSY294 cells untreated (upper panel) and caspofungin (10 µg/ml) treated cells (lower panel) on a PLL-PEG treated glass surface;

FIG. 23*b* shows the displacements per frame of all 20 cells on a PLL-PEG treated surface;

FIG. 23*c* shows the total displacement during 12 s measurement of 20 cells on a PLL-PEG treated surface, with the Wilcoxon test: ** $P<0.0001$, * $P<0.001$;

FIG. 23*d* shows the effect of the surface on cellular movement of *C. albicans*, in particular the displacement/frame of 20 *C. albicans* DSY294 cells untreated (upper panel) and caspofungin (10 µg/ml) treated cells (lower panel) on glass surface;

FIG. 23*e* shows the displacements per frame of all 20 cells on a glass treated surface FIG. 23*f* shows the total displacement during 12 s measurement of 20 cells on a glass treated surface, with the Wilcoxon test: ** $P<0.0001$, * $P<0.001$ FIG. 23*g* shows the displacement/frame of 20 *C. albicans* DSY1024 cells untreated (upper panel) and caspofungin (10 µg/ml) treated cells (lower panel) on a PLL-PEG treated;

FIG. 23*h* shows the displacements per frame of all 20 cells on a PLL-PEG treated surface;

FIG. 23*i* shows the total displacement during 12 s measurement of 20 cells on a PLL-PEG treated surface, with the Wilcoxon test: ** $P<0.0001$, * $P<0.001$ FIG. 23*j* shows the displacement/frame of 20 *C. albicans* DSY1024 cells untreated (upper panel) and caspofungin (10 µg/ml) treated cells (lower panel) on glass surface;

FIG. 23*k* shows the displacements per frame of all 20 cells on a glass treated surface FIG. 23*l* shows the total displacement during 12 s measurement of 20 cells on a glass treated surface, with the Wilcoxon test: ** $P<0.0001$, * $P<0.001$;

FIG. 24 shows an example of a manual selection of individual cells that will be analysed by a cross-correlation algorithm.

DESCRIPTION OF PREFERRED EMBODIMENTS

The present invention will be described with respect to particular embodiments and with reference to certain drawings but the invention is not limited thereto but only by the claims.

The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In one aspect, the present invention can relate to a method for deriving particle characteristics. The method may comprise detecting characteristics of one particle or a plurality of particles. The particles may be any type of particles, such as in one example being cells. The method comprises imaging the movement of at least one free-floating particle in a liquid environment at at least one moment in time. The particles thereby typically do not need to be attached to a surface or to larger particles. They thus may be unattached. The imaging may be optical imaging. The imaging may be video recordings. Such video recording may be a video of the movement over a predetermined time, such as for example at least 2 seconds, at least 5 seconds or at least 10 seconds. These video recording may be repeated a plurality of times. This may correspond with different recordings spaced with predetermined time intervals between the recordings.

The method also comprises determining for at least one moment in time a movement parameter based on the imaged movement of the free-floating particles in the liquid environment. The movement parameter may be an x,y movement of a particle. The movement parameter may be an oscillation frequency of an oscillation movement of the free-floating particle. The method also comprises deriving from the movement parameter a characteristic of the at least one particle.

According to some embodiments of the present invention, for determining a movement parameter, the method may make use of an algorithm for registering images. One example of such an algorithm derivation of the movement of particles over time may make use of an algorithm for registering images such as for example described by Manuale Guizar-Sicairos et al. in Optics Letters 33, 156-158 (2008) entitled "Efficient subpixel image registration algorithms". Alternatively also other algorithms may be used.

In some embodiments, the method may be an algorithm as illustrated in FIG. 8. In other embodiments, the method may be an algorithm as illustrated in FIG. 9.

In some embodiments use may be made of a self-learning algorithm for the automated selection of the cells before the nanomotion is measured. Use may for example be made of a neural network. In one example use may be made of a self-learning algorithm as shown in FIGS. 10A, 10B. Such a method may comprises for example generating images of simulated cells. e.g. a large number of images such as for example about 50000 images or more, and thus obtaining a set of synthetic cell images, providing such images to a cell detection model for training the model and updating the model, assessing the model and improving it, so as to end up with a trained model.

By way of illustration, embodiments of the present invention not being limited thereto, features and advantages of an embodiment of the present invention will be illustrated below. The below example illustrates advantages of method for rapid, label-free and attachment-free characterisation of single-cell antifungal susceptibility using optical nanomotion detection.

The example shown below is framed in the dramatically increased global incidence of fungal disease in recent years. The emergence of antifungal resistant yeast strains represents nowadays a serious challenge for humanity. The development of rapid antifungal susceptibility testing (AFST) to guide treatment and clinical management decisions is one of the options to limit the spread of these organisms. In the exemplary embodiment shown below, a rapid and simple method is described that permits to assess the susceptibility of single fungal cells to antifungal drugs with very basic laboratory material. i.e. an optical microscope, a camera and a computer. Advantageously, the technique is label-free and does not require the attachment of the cells onto a substrate, which dramatically simplifies and broadens its applicability, even in remote doctor's practices in developing countries. An "optical nanomotion detection" (ONMD) method was developed that is based on cross-correlation of consecutive recorded optical images by a microscope, and it is demonstrated that the recorded "nanomotion" magnitude is proportional to the cell's activity. A deep learning single-cell detection algorithm is implemented in the video analysis pipeline to automate the detection of the individual cells amid the hundreds to thousands cells within the video sequence. Consequently, the developed method can address the nanomotion pattern of single cells as well as whole cellular populations. This methodology was applied in the present example to evaluate the antifungal susceptibility of various *Candida albicans, C. glabrata* and *C. lusitaniae* strains (including clinical strains), and the model yeast *Saccharomyces cerevisiae* for various antifungals. Additionally, amphotericin B dose-response curves were setup for *C. albicans* strains, which allowed the determination of the minimal inhibitory concentration (MIC). Apart from detecting life-death transition, the method is also sensitive to the metabolic activity of the cells as demonstrated by the correlation that was found between the nanomotion pattern of the cells and the temperature and the nutrients availability. An analysis of the yeast nanomotion pattern in the frequency domain was performed for this particular example which highlighted that the oscillation frequencies that change the most between living and death yeast cells are located between 0.5 and 4 Hz.

In the present example it is illustrated that an optical microscope equipped with a video camera can detect living cells nanometric scale oscillations. The oscillations are monitored by periodically recording (in the present example every hour) 12 s long movies of the cells in the absence and presence of a drug and processing the movies with an algorithm that can highlight sub-pixel scale movements (FIG. 1). Interestingly and contrarily to the state of the art techniques, the cells do not have to be attached onto a cantilever nor a substrate. The lack of attachment makes cell oscillations easier to detect with medium to high magnification optical microscopy. The technique is also label-free permitting a very rapid and simple setup. Importantly, the method applies to single cells as well as to whole populations (100-1000 cells) due to the implementation of a deep learning detection algorithm and further automation that dramatically accelerates the data processing.

The method was tested on different types of yeasts such as different *Candida* species and the model yeast *S. cerevisiae*. These *Candida* species can be involved in candidiasis, which is a human fungal infection that can be hard to treat due to the acquired resistance. Some of the evaluated yeast strains were hypersusceptible or resistant to the applied antifungal drugs to challenge their viability. In every case, the results corroborated with classical sensitivity tests. Antifungal dose dependence as well temperature dependence tests were carried out and demonstrated that optical nanomotion detection (ONMD) is not limited to life—death transition detection but can also monitor metabolic rate variations.

To track single cells, in the present example a cross-correlation image registration algorithm was used. The method was documented to efficiently track subtle modifications of keratin networks in living cells and displacements of myoblasts. The algorithm is based on the initial estimation of the cross-correlation peak between the first and every subsequent frame. It provides a numerical value for the image translation with a sub-pixel (sub-µm) resolution and does not require heavy calculations. Our program calculates the cell displacement for each frame and saves the trajectories of tracked cells as well as the root mean square of the displacement to an MS Excel file.

Figure 2A:
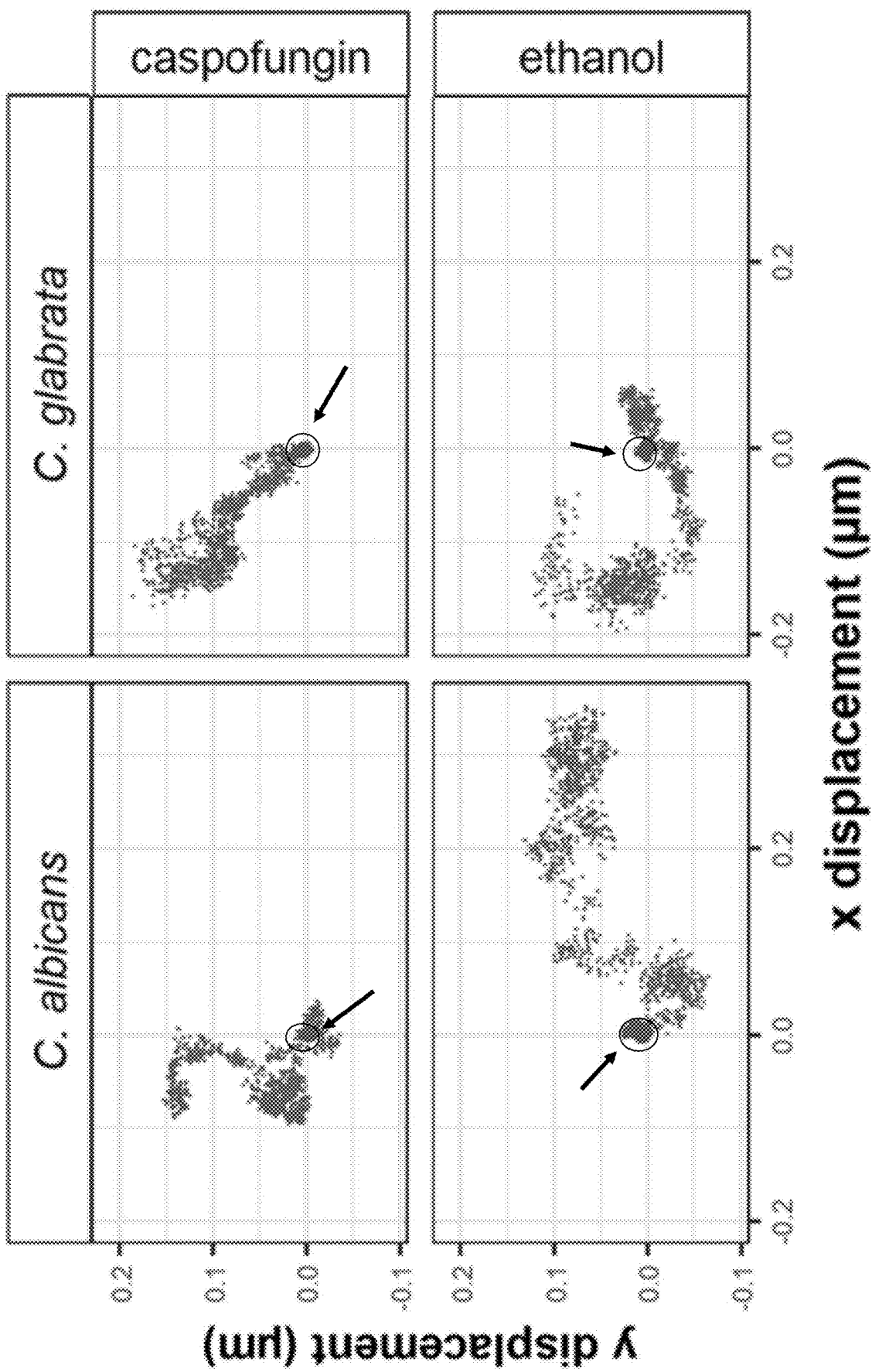
FIG. 2a shows the effect of ethanol and antifungals on the optical nanomoton detection (ONMD) of yeast cells, in particular the effect of ethanol (70% v/v) and caspofungin (100 µg/ml) on the x y displacements of *C. albicans* DSY294, *C. glabrata* DSY562 during 12 s (1000 frames, 83 fps). The dots within circle represent the position of the cell after the treatment with the antifungal caspofungin or ethanol.
Figure 2B:
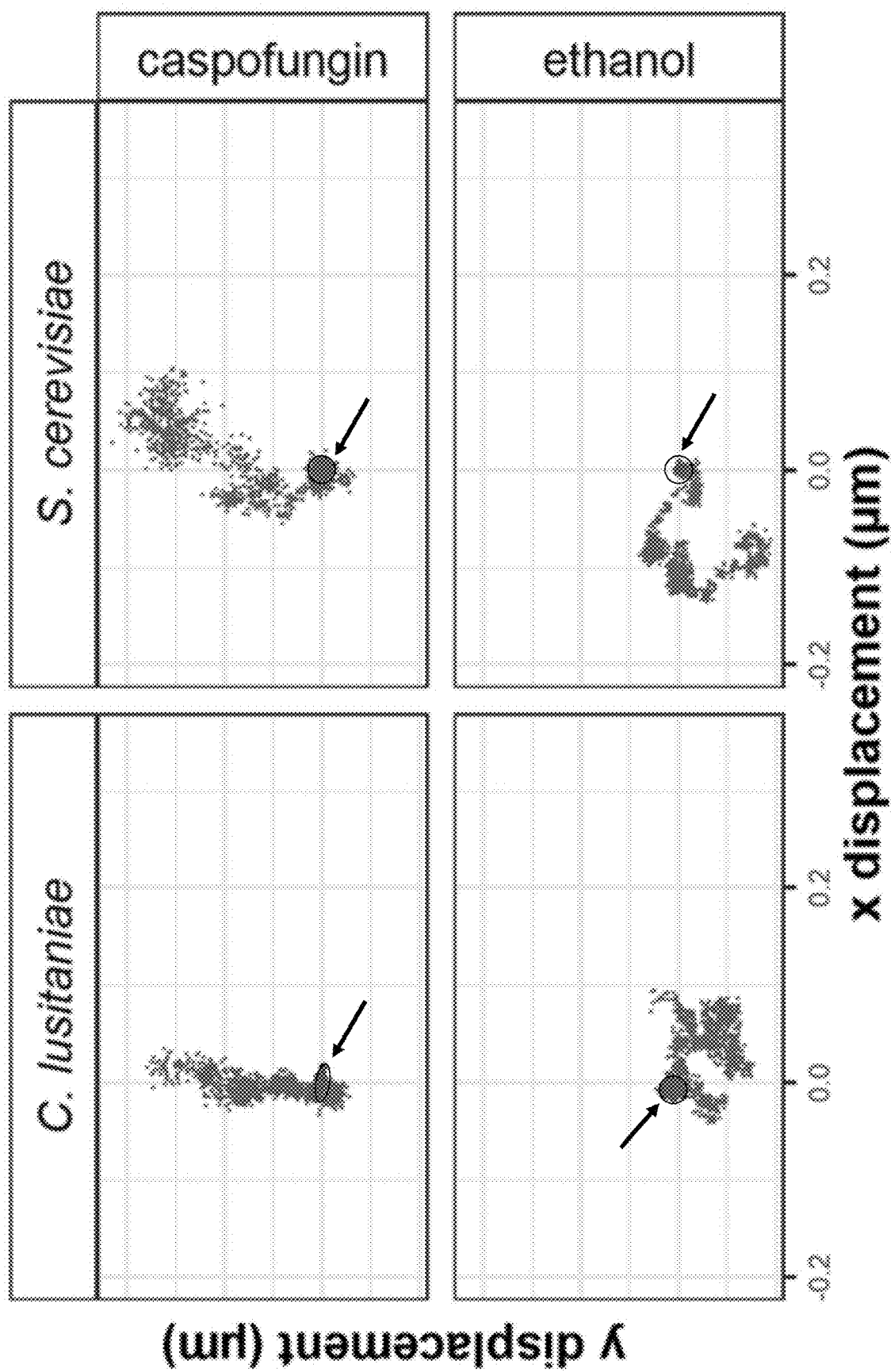
FIG. 2b shows the effect of ethanol and antifungals on the optical nanomotion detection (ONMD) of yeast cells, in particular the effect of ethanol (70% v/v) and caspofungin (100 µg/m) on the x y displacements of *C. lusitanise* DSY4606, and *S. cerevisiae* BY4742 cells during 12 s (1000 frames, 83 fps) The dots within circle represent the position of the cell after the treatment with the antifungal caspofungin or ethanol.
Figure 2C:
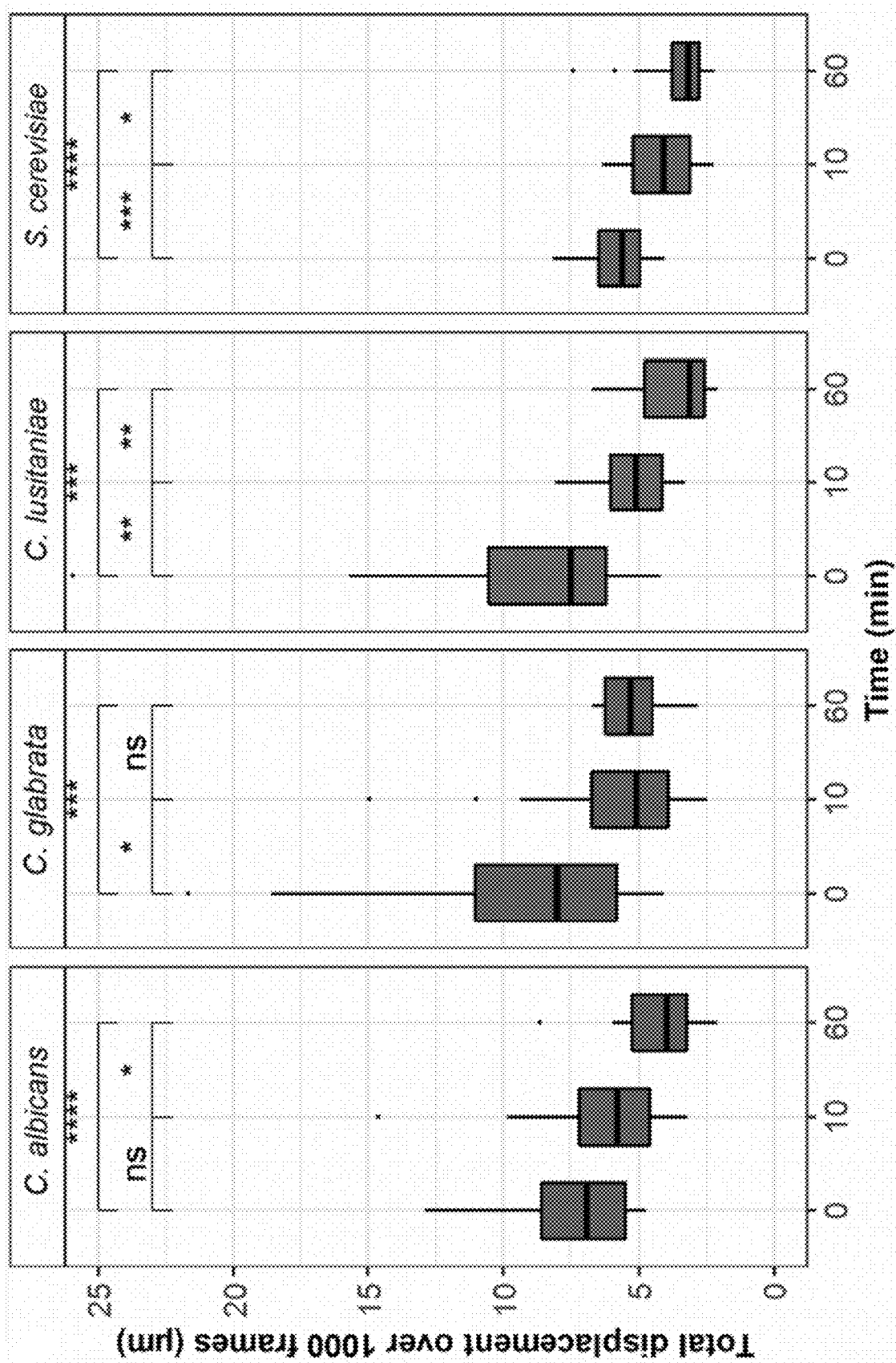
FIG. 2c shows the effect of ethanol and antifungals on the optical nanomotion detection (ONMD) of yeast cells, in particular the effect of ethanol (70% v/v) on the total displacement during 12 s measurement as a function of time on *C. albicans* DSY294, *C. glabrata* DSY562, *C. lusitaniae* DSY4606, and *S. cerevisiae* BY4742. Remark: the ethanol solution was added to the same well at the top and mixing occurred only by diffusion, which increases the time an effect on the viability is observed. Box plot whiskers within 1.5 IQR of 20 single cells recorded during 12 s; paired Student's t test; **: P<0.0001, *: P<0.001, **: P<0.01, *: P<0.1, ns: not significant.

In a first set of experiments, the antimicrobial activity of ethanol on the nanomotion of various *Candida* strains and the model yeast *S. cerevisiae* was assessed. Therefore, the effect of high ethanol concentration (70%) on the x y displacements of *C. albicans, C. glabrata, C. lusitaniae* and *S. cerevisiae* cells (FIGS. 2a and 2b lower panels) was explored. The results show that the x y displacements are quickly and drastically reduced for ethanol treated cells. The total displacements over 1000 frames were reduced significantly after only 10 min of treatment (FIG. 2c). Ten minutes after the addition of ethanol and diffusive mixing, a significant (t-test) decrease is detected for *C. glabrata, C. lusitanise* and *S. cerevisiae*, *C. albicans* seems somewhat better ethanol tolerant since a significant decrease of the total displacement was measured only after 60 min. Ethanol is one of the products of the metabolism of glucose by *Candida* strains. It can be used as a sole carbon source and its tolerance was documented to be strain dependent. *S. cerevisiae* can also produce ethanol, it affects the growth rate at moderate concentrations (5-7%), and at higher concentrations (>10%) it will impair the cell membrane integrity, eventually leading to apoptotic cell death. Ethanol alters the fluidity of the yeast cell membrane and dissipates the transmembrane electrochemical potential, which results in ionic species permeability and leakage of metabolites. Ethanol can freely diffuse inside the cell, and will directly perturb and denature intracellular proteins.

Figure 2D:
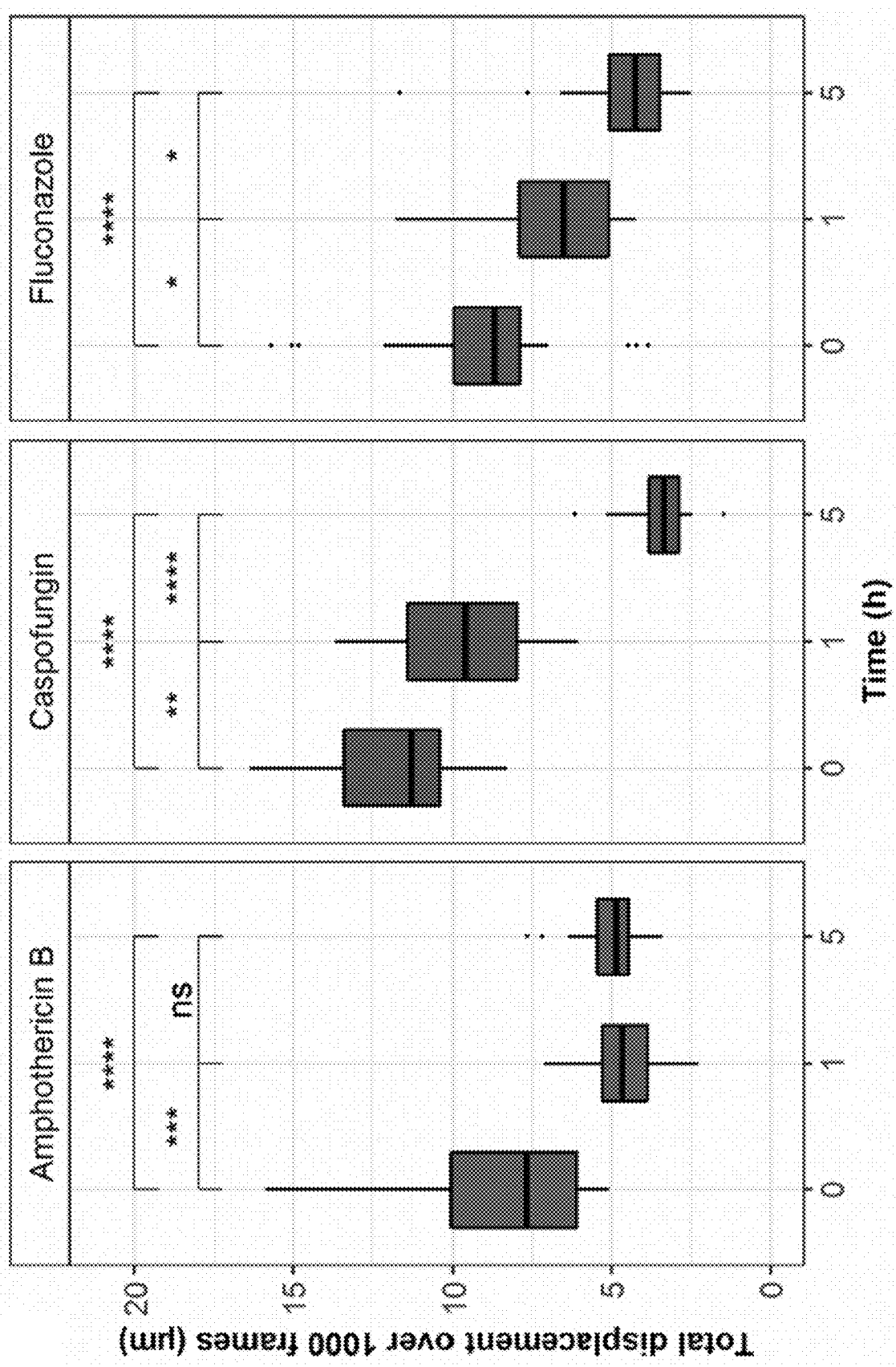
FIG. 2d shows the effect of ethanol and antifungals on the optical nanomotion detection (ONMD) of yeast cells, in particular the effect of amphotericin 8 (100 µg/ml), caspofungin (100 µg/ml) and fluconazole (400 µg/ml) on *C. albicans* DSY294. Box plot whiskers within 1.5 IQR of 20 single cells recorded during 12 s; paired Student's t test; **: P<0.0001, *: P<0.001, **: P<0.01, *: P<0.1, ns: not significant.
Figure 2E:
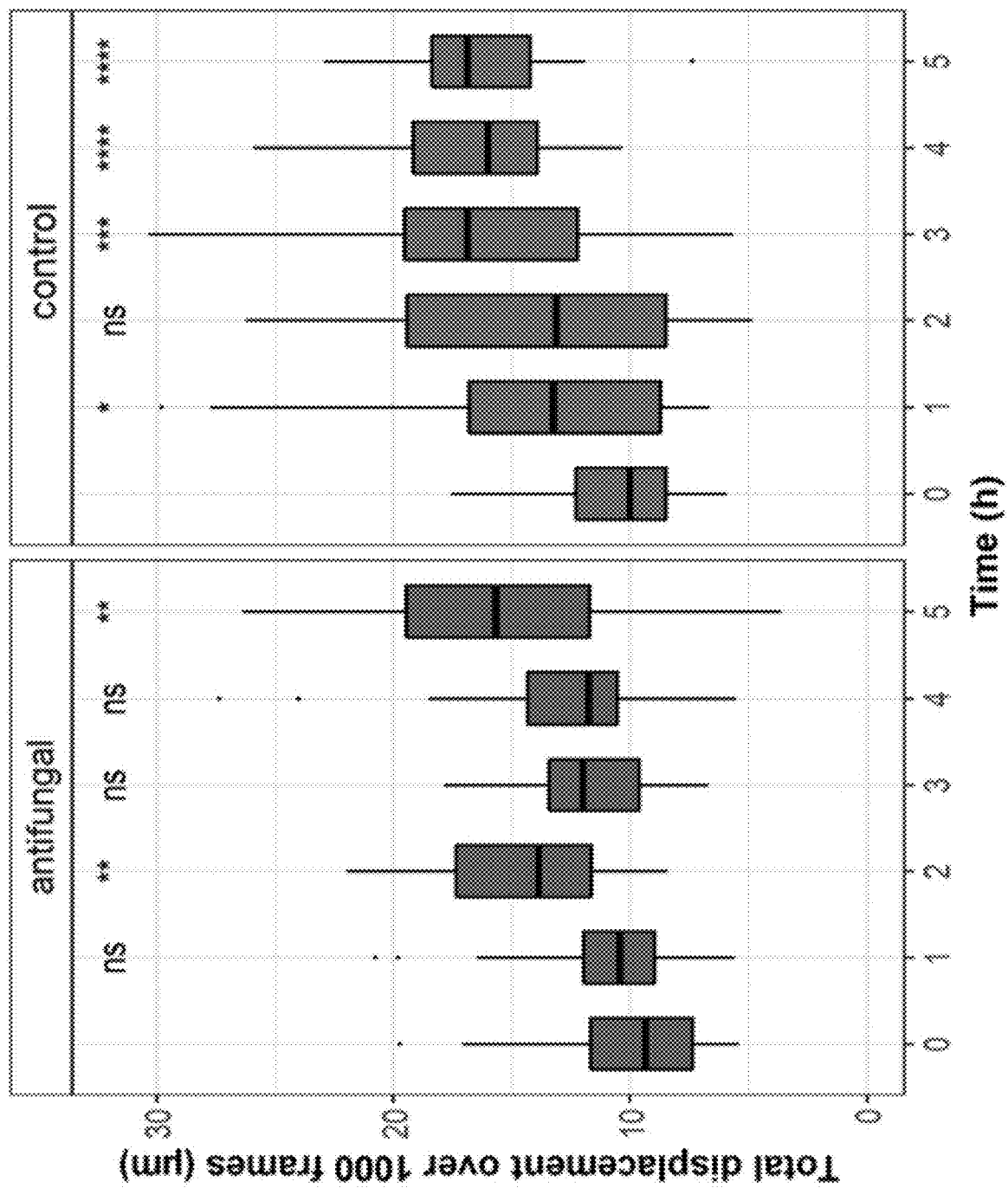
FIG. 2e shows the effect of ethanol and antifungals on the optical nanomotion detection (ONMD) of yeast cells, in particular the effect of caspofungin (10 µg/ml) on candin-resistant *C. albicans* DSY4614 clinical strain. The "control" represents the untreated cells that were grown in YPD growth medium. Box plot whiskers within 1.5 IQR of 20 single cells recorded during 12 s; paired Student's t test; **: P<0.0001, *: P<0.001, **: P<0.01, *: P<0.1, ns: not significant.
Figure 2F:
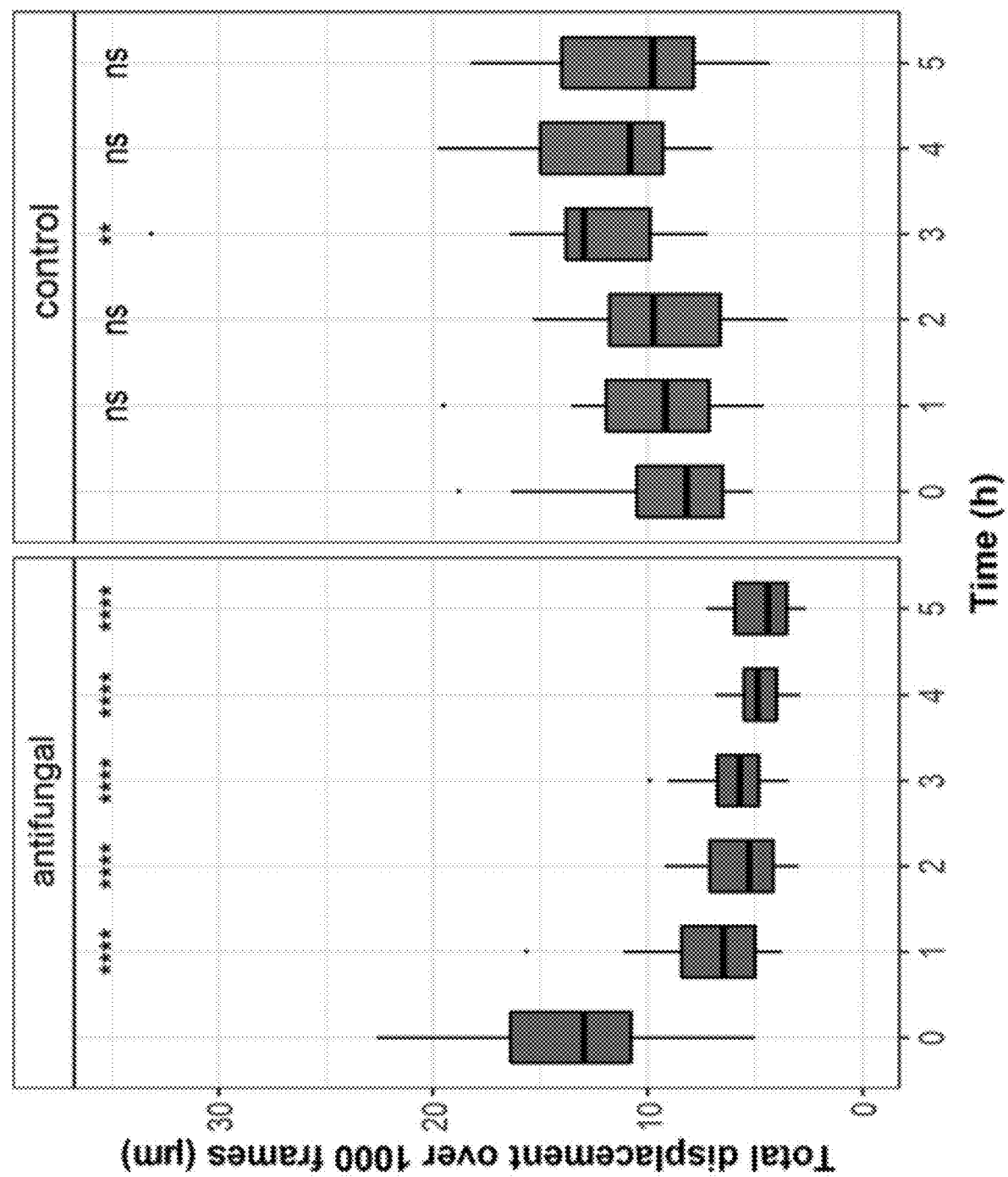
FIG. 2f shows the effect of ethanol and antifungals on the optical nanomotion detection (ONMD) of yeast cells, in particular the effect of caspofungin (10 on the hypersusceptible (mutant for efflux systems) *C. albicans* DSY1024 strain. The "control" represents the untreated cells that were grown in YPD growth medium. Box plot whiskers within 1.5 IQR of 20 single cells recorded during 12 s; paired Student's t test; **: P<0.0001, *: P<0.001, **: P<0.01, *: P<0.1, ns: not significant.
Figure 4A:
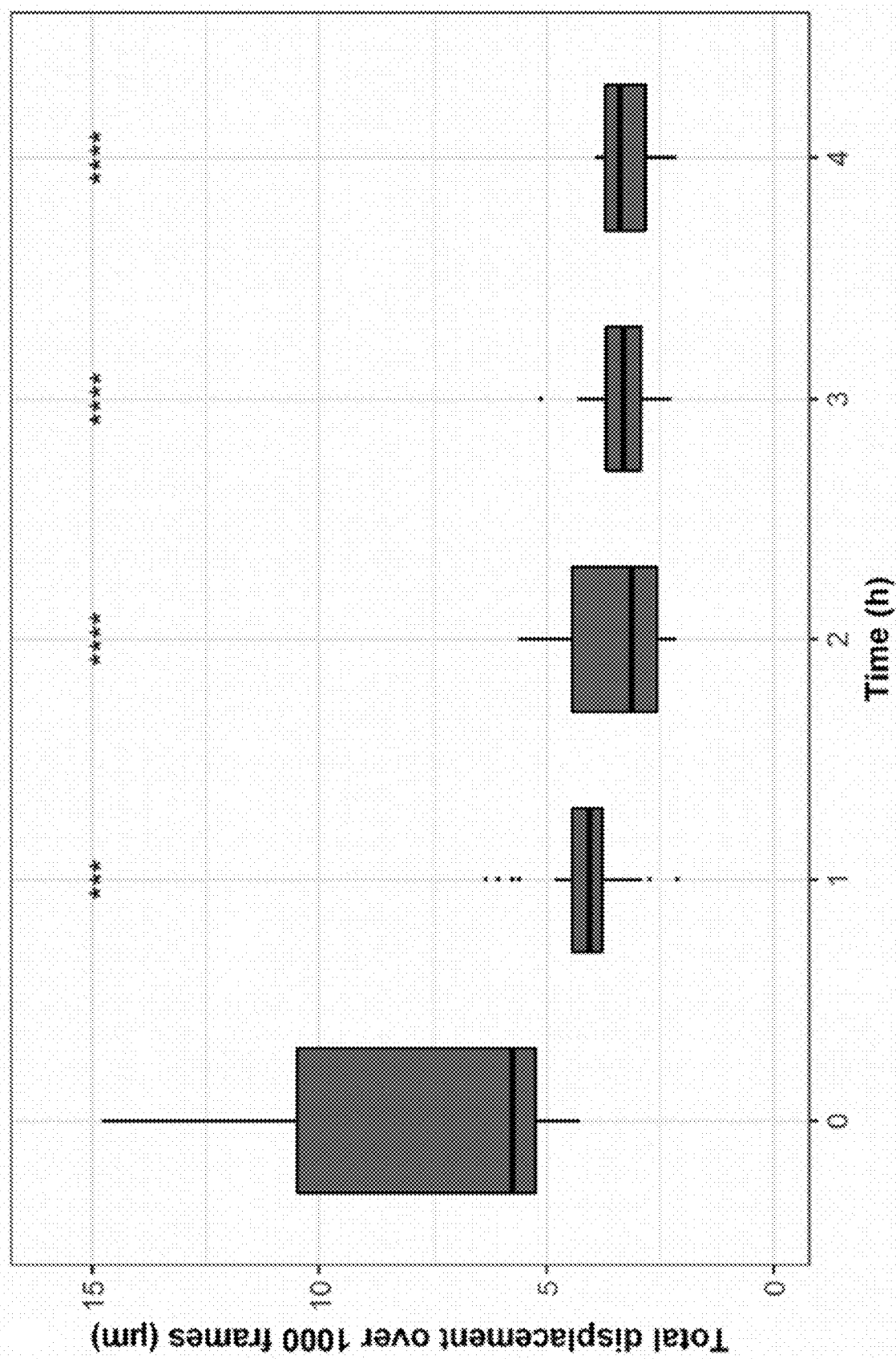
FIG. 4a shows supplementary *Candida* results, in particular the effect of caspofungin on *C. glabrata* DSY582. Box plot whiskers within 1.5 IQR of 20 single cells recorded during 12 s; paired Student's t test **: P<0.0001, *: P<0.001, **: P<0.01. *: P<0.1, ns: not significant.
Figure 4B:
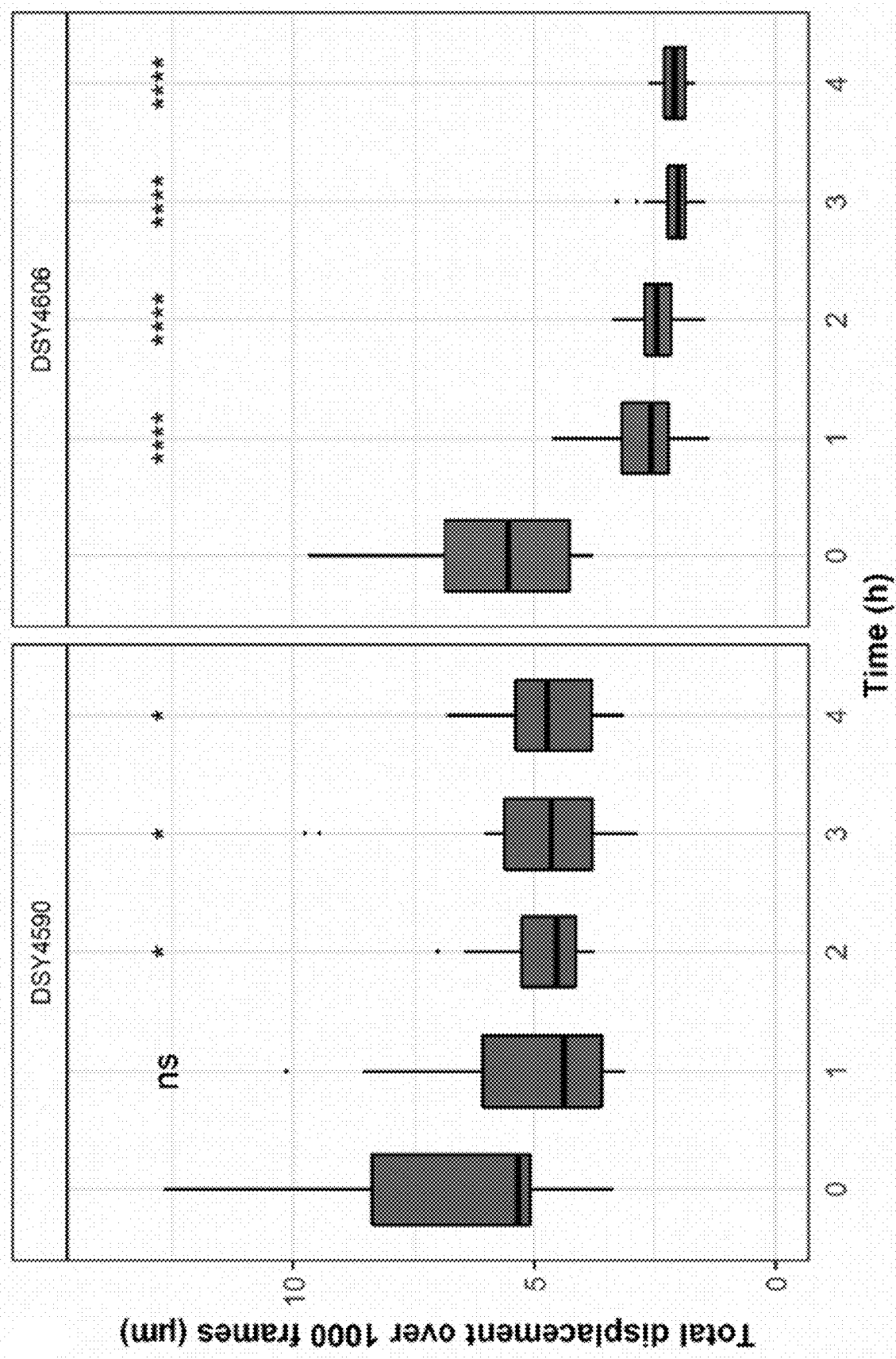
FIG. 4b shows supplementary *Candida* results, in particular the effect of caspofungin (10 µg/ml) on *C. lusitaniae* DSY4606 clinical wild-type and resistant strain DSY4590. Box plot whiskers within 1.5 IQR of 20 single cells recorded during 12 s; paired Student's t test; **: P<0.0001, *: P<0.001, **: P<0.01, *: P<0.1, ns: not significant.
Figure 5A:
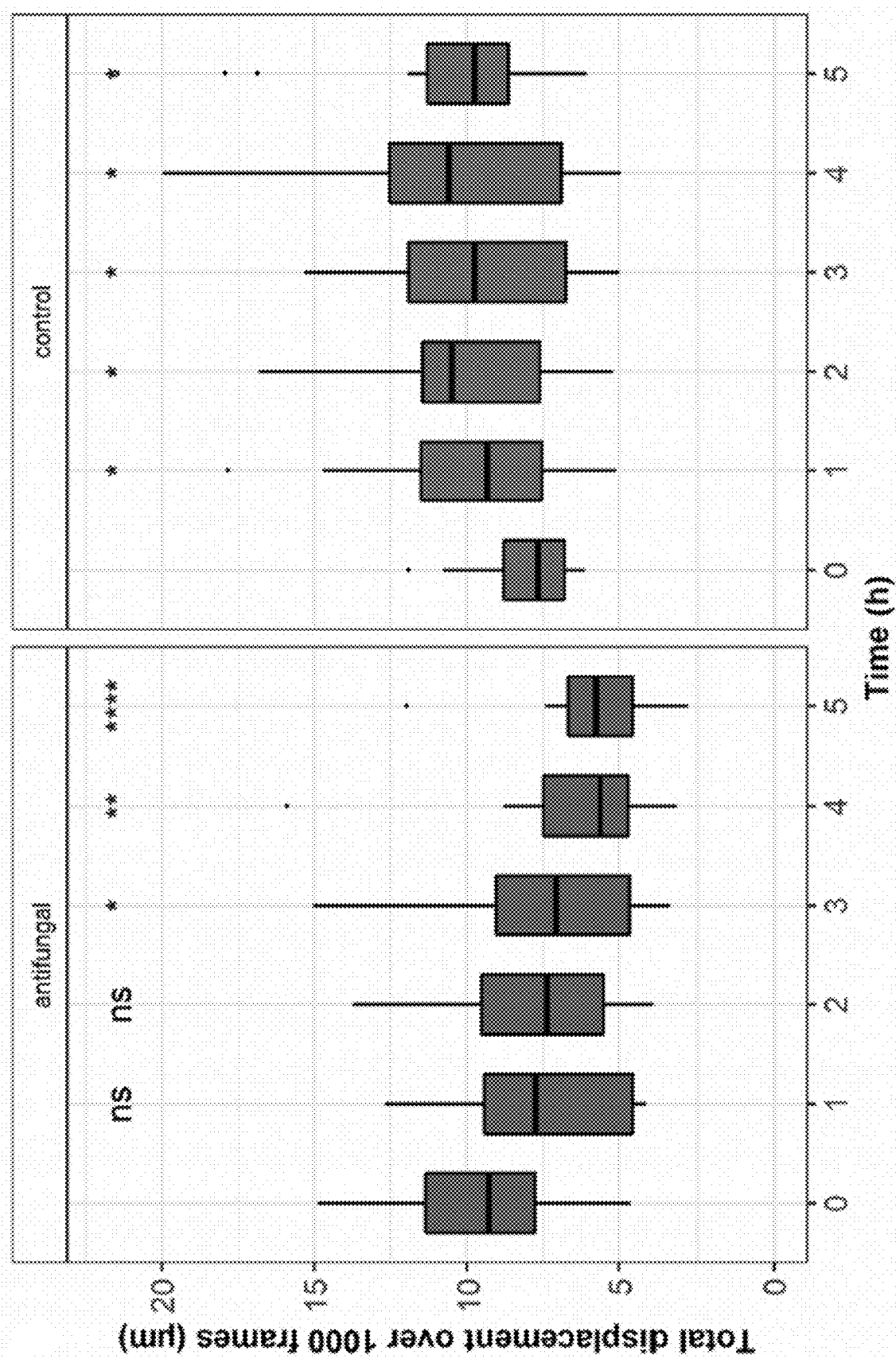
FIG. 5a shows the *S. cerevisiae* results, in particular the effect of caspofungin (10 µg/ml) on *S. cerevisiae* BY4742. Box plot whiskers within 1.5 IQR of 20 single cells recorded during 12 s; paired Student's t test. **: P<0,0001, *: P<0.001, **: P<0.01, *: P<0.1, ns: not significant.
Figure 5B:
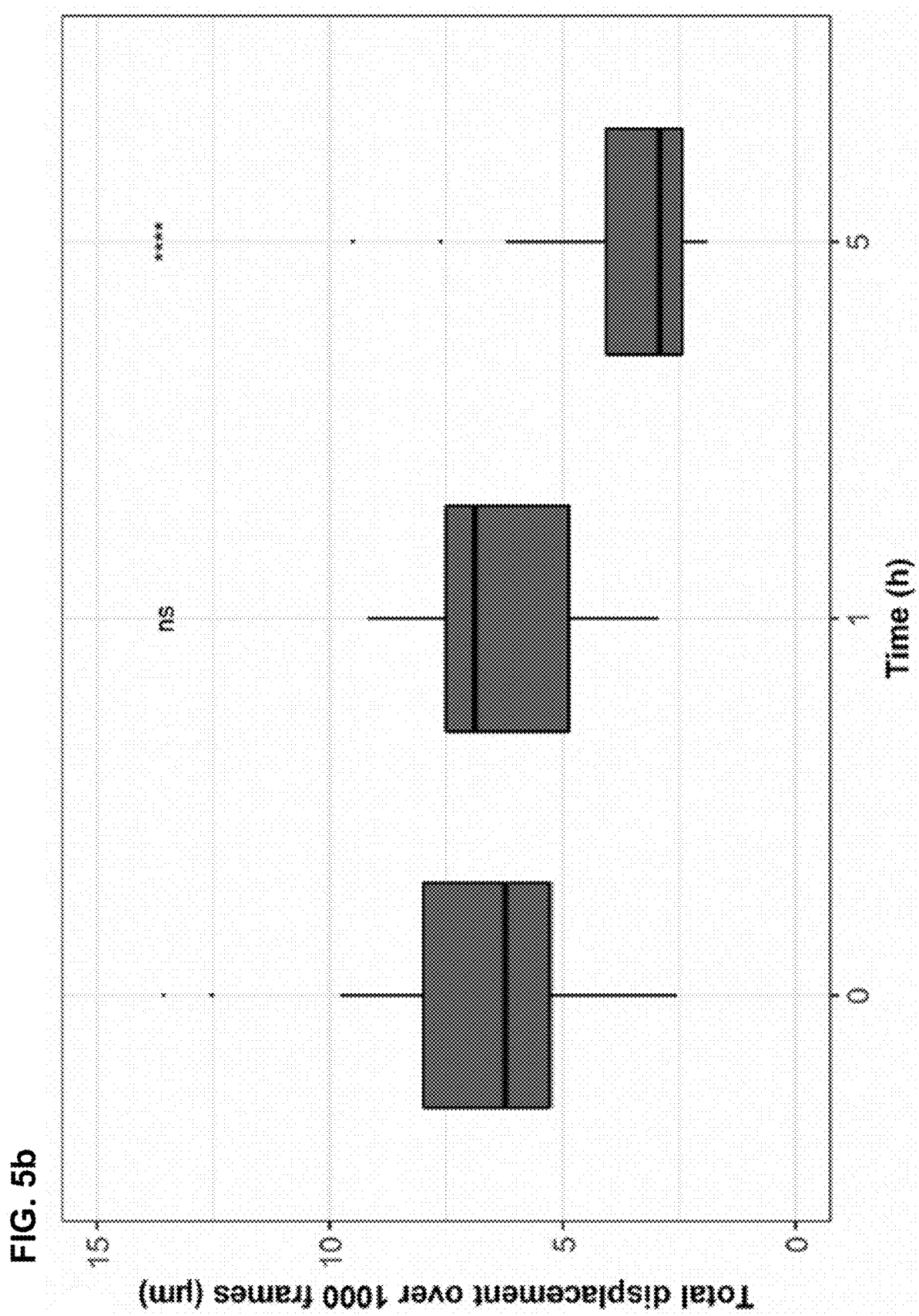
FIG. 5b shows the *S. cerevisiae* results, in particular the effect of fluconazole (400 µg/ml) on *S. cerevisiae* BY4742.

In a next step, the efficiency of ONMD to perform AFST was evaluated. The x y displacement reduced significantly after treatment of the yeast cells with antifungals. As an example, FIGS. 2a and 2b (upper panels) shows the reduced displacement of a *C. albicans, C. glabrata, C. lusitaniae* and *S. cerevisiae* cells after treatment with caspofungin. The effect of the antifungals amphotericin B, caspofungin and fluconazole on *C. albicans* DSY294 wild-type strain is shown in FIG. 2d. For all 3 antifungals, a significant decrease in the mean total displacement was detected after 1 h treatment (FIG. 2d). Amphotericin B is the most effective antifungal for this strain since after already 1 h the nanomotion signal decreased to values close to those recorded on dead cells. The polyene amphotericin B selectively binds to ergosterol in the cell membrane and causes the formation of pores (which results in a quicker dead), whereas the azole fluconazole selectively inhibits cytochrome P450-dependent lanosterol-14-α-demethylase and the echinocandin caspofungin inhibits fungal β-1,3-glucan synthase. The reported amphotencin B MIC value for *C. albicans* DSY strains was 0.5 µg/ml. Caspofungin did not affect the nanomotion of the candin-resistant *C. albicans* DSY4614 clinical strain (FIG. 2e) but did kill the hypersusceptible (mutant for efflux systems) (Table 1) *C. albicans* DSY1024 strain (FIG. 2f). The reported caspofungin MIC values for *C. albicans* are in the range of 0.03 to 8 µg/ml. Nanomotion AFST of caspofungin on *C. glabrata* DSY562 clinical wild-type strain showed that the cells were dead after 2 h of treatment (FIG. 4a). Caspofungin killed also *C. lusitaniae* DSY4606 clinical wild-type strain quickly (FIG. 4b right panel), whereas the resistant DSY4590 clinical strain was not affected by the treatment (FIG. 4b left panel). The effect of caspofungin on *S. cerevisiae* BY4742 was detected after 3 h of treatment as a significant decrease of the total displacement was observed (FIG. 5a). There was no effect of fluconazole on *S. cerevisiae* after 1 h of treatment (FIG. 5b) in contrast to the effect on *C. albicans* DSY294 (FIG. 2d); a significant decrease in total displacement was obvious after 5 h of treatment. This can be explained by the larger fluconazole MIC value (1-8 µg/ml) for *S. cerevisiae* compared to the one for *C. albicans* DSY294 (0.3 µg/l).

Figure 2G:
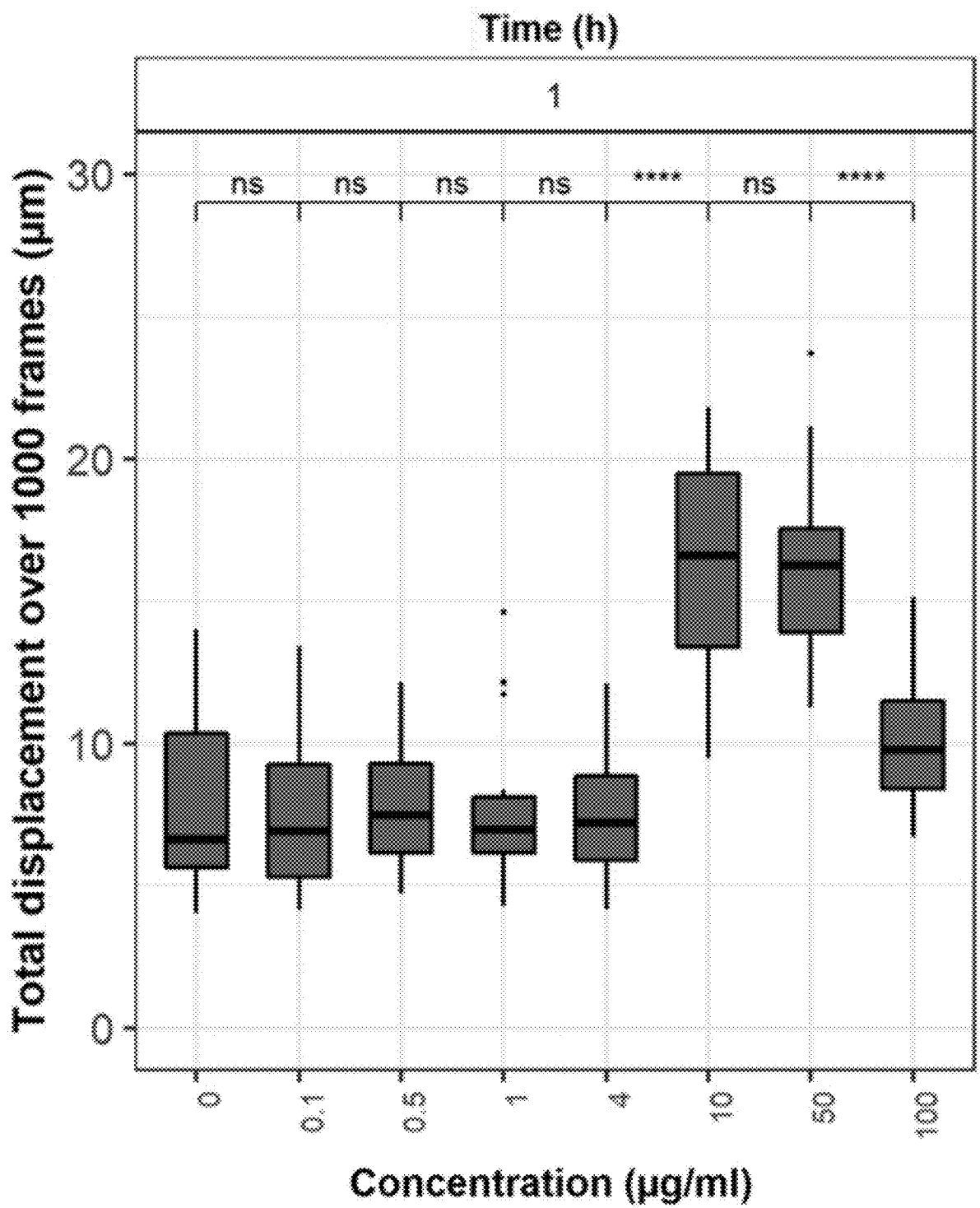
FIG. 2g shows the effect of ethanol and antifungals on the optical nanomotion detection (ONMD) of yeast cells, in particular the effect Amphotericin B dose-response curve for *C. albicans* CAF2-1 wild-type strain after 1 h treatment. Box plot whiskers within 1.5 IQR of 20 single cells recorded during 12 s; paired Student's t test; **: P<0.0001, *: P<0.001, **: P<0.01, *: P<0.1, ns: not significant.
Figure 2H:
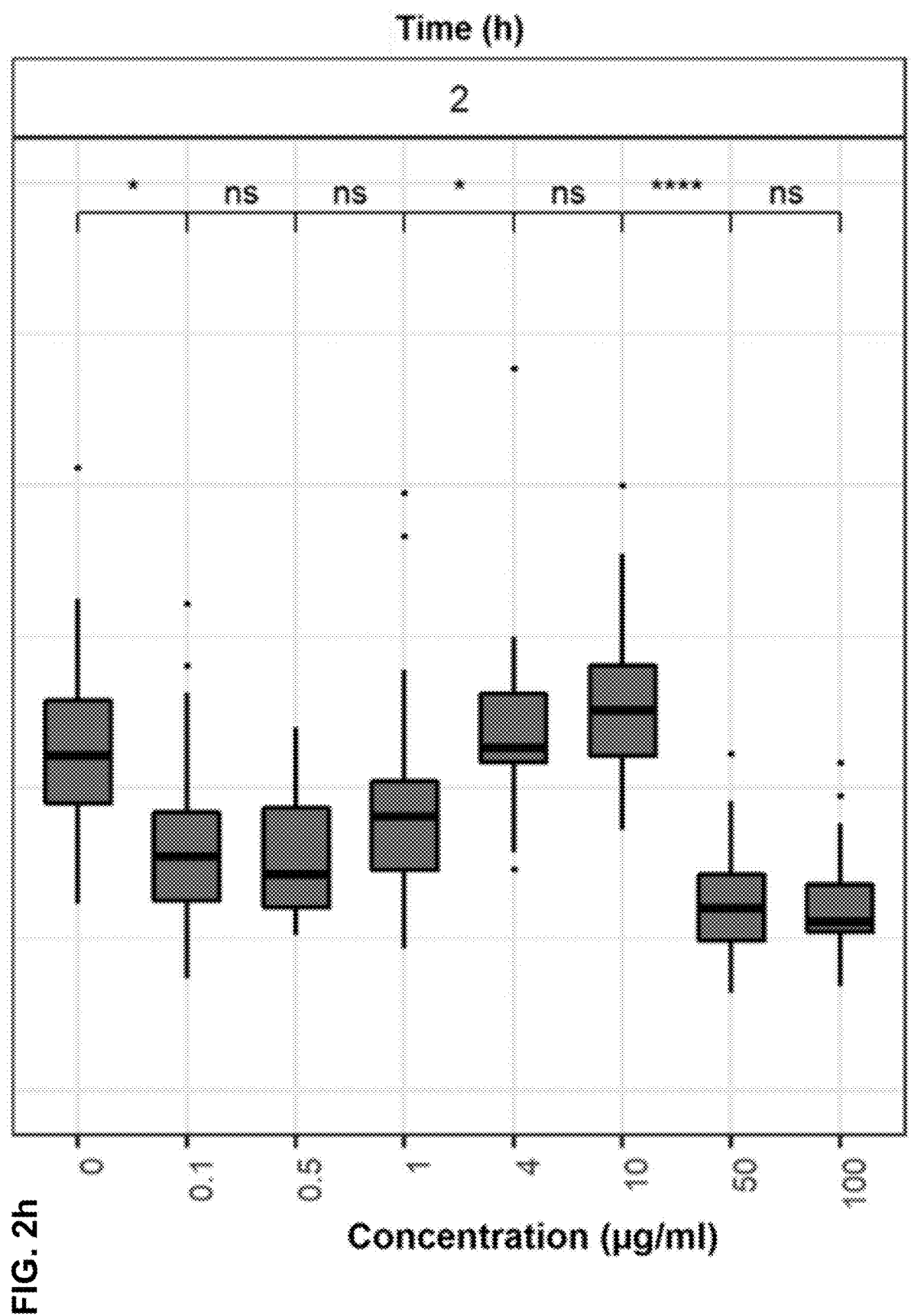
FIG. 2h shows the effect of ethanol and antifungals on the optical nanomotion detection (ONMD) of yeast cells, in particular the effect Amphotericin B dose-response curve for *C. albicans* CAF2-1 wild-type strain after 2 h treatment. Box plot whiskers within 1.5 IQR of 20 single cells recorded during 12 s; paired Student's t test; **: P<0.0001, *: P<0.001. **: P<0.01, *: P<0.1, ns: not significant.
Figure 2I:
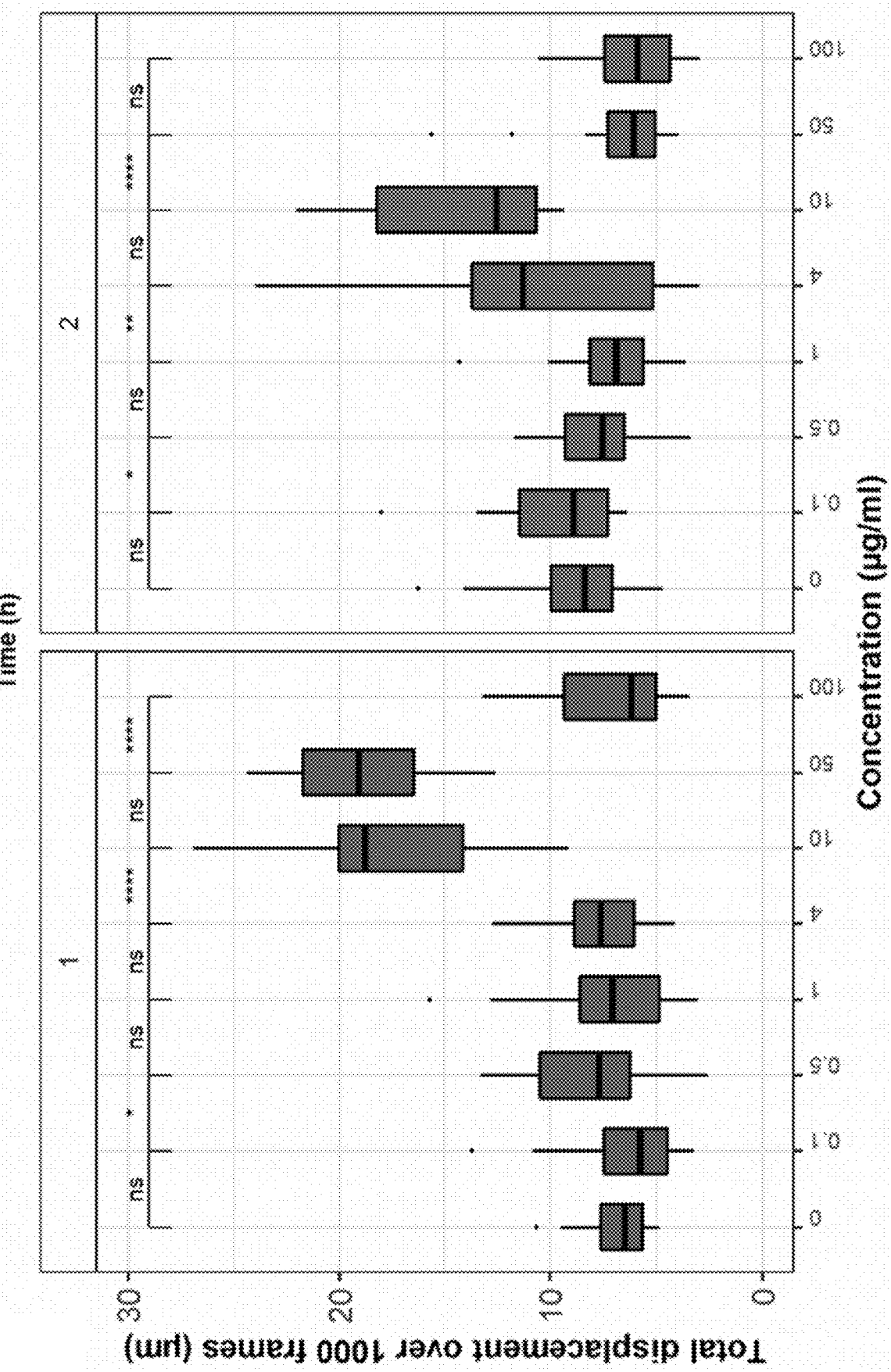
FIG. 2i shows the effect of ethanol and antifungals on the optical nanomotion detection (ONMD) of yeast cells, in particular the effect Amphotericin B dose response curve for *C. albicans* DSY294. Box plot whiskers within 1.5 IQR of 20 single cells recorded during 12 s: paired Student's t test; **: P<0.0001. *: P<0.001, **: P<0.01, *: P<0.1, ns: not significant.

The amphotericin B dose-response curve for the *C. albicans* CAF2-1 wild-type strain was also explored by using the ONMD method (FIGS. 2g and 2h). The mean total displacement increased after 1 h for a concentration of 10 µg/ml (FIG. 2gl) and after 2 h for a concentration of 4 µg/ml (FIG. 2h); whereas it decreased for higher drug concentrations. A similar amphotericin B dose-response curve was recorded for the *C. albicans* DSY294 clinical wild-type strain (FIG. 2i). This indicates that the mechanism of action of amphotericin increases the movement of the cells around its MIC, i.e. the antifungal action increases the metabolic activity of the cells. An increase of the nanomotion (measured using the AFM-cantilever method) of the bacterium *Bordetella pertussis* around the MIC for the antibiotic was also previously observed. Our results also show that it takes more time for lower concentrations to be detectable as a change in nanomotion, and that the ONMD allows to record the dynamics of cell death. The lowest concentration where a change in nanomotion can be observed, corresponds to the MIC value. We detected a MIC value of 1-4 µg/ml, and 0.3 µg/ml was reported using the classical "microtitre plate method" for this strain, and a range of 0.1 to 4.0 µg/ml was reported for *C. albicans*.

Figure 3A:
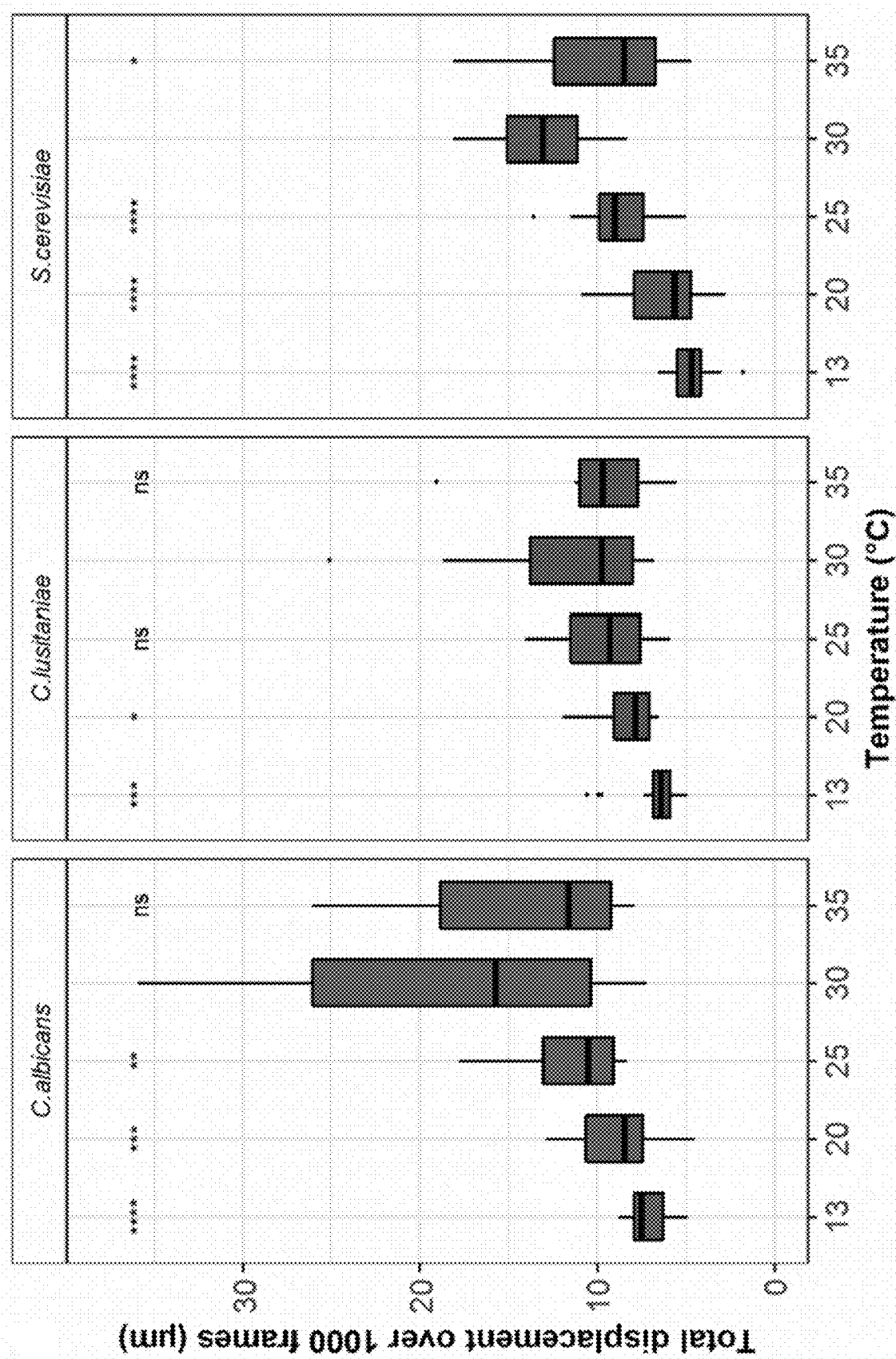
FIG. 3a shows the effect of the temperature and nutritional environment on the optical nanomotion of yeast cells, in particular the effect of the temperature on the total displacement of *C. albicans* DSY294, *C. lusitaniae* DSY4606, and *S. cerevisiae* BY4742. Box plot whiskers within 1.5 IQR of 20 single cells recorded during 12 s: paired Student's t test; **: P<0.0001, *: P<0.001, **: P<0.01, *: P<0.1, ns: not significant.
Figure 3B:
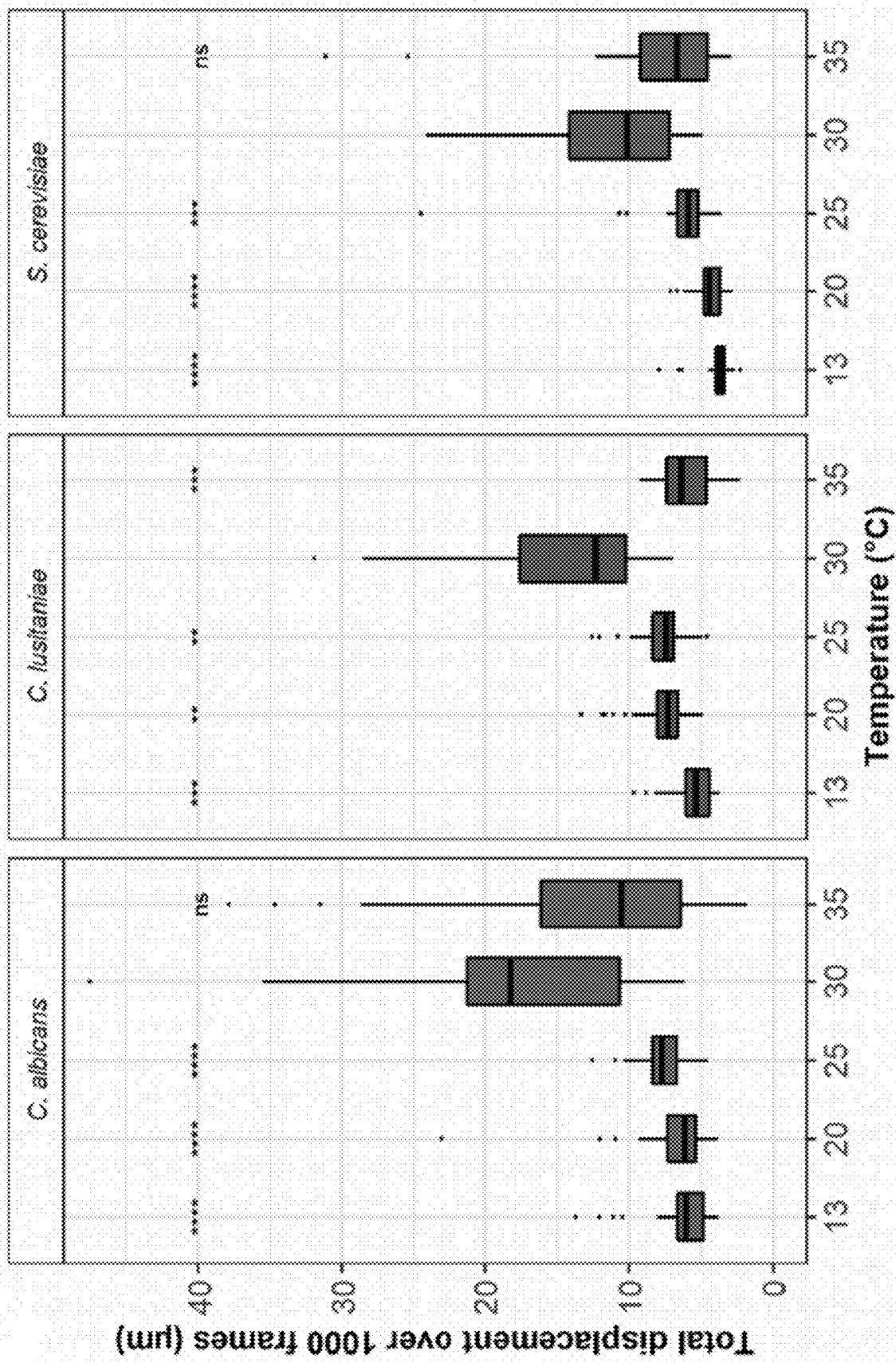
FIG. 3b shows the effect of the temperature and nutritional environment on the optical nanomotion of yeast cells, in particular the effect of the temperature on the total displacement: results obtained with the automated detection method. Box plot whiskers within 1.5 IQR of 20 single cells recorded during 12 s; paired Student's t test; **: P<0.0001, *: P<0.001, **: P<0.01, *: P<0.1, ns: not significant.
Figure 3C:
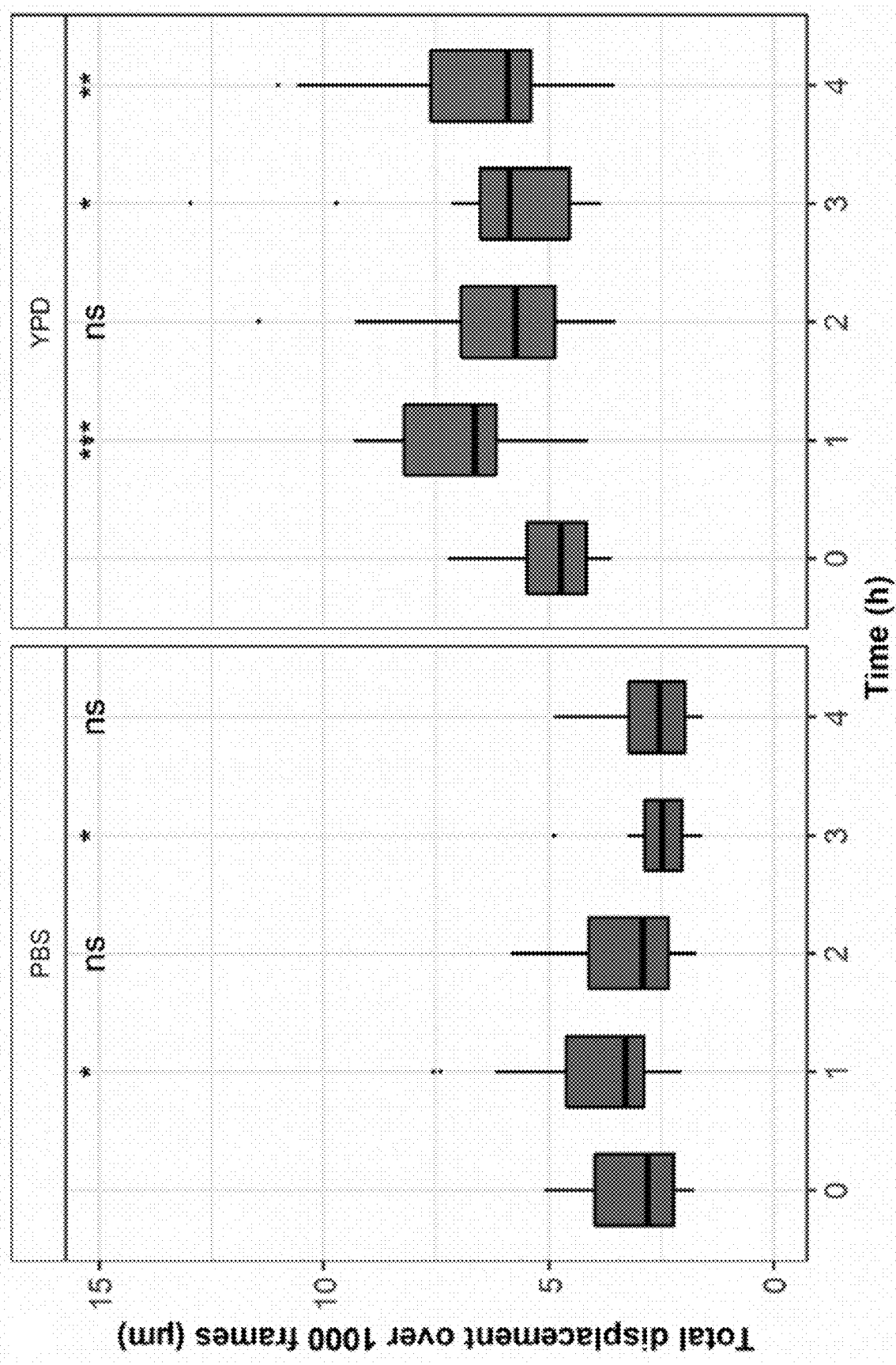
FIG. 3c shows the effect of the temperature and nutritional environment on the optical nanomotion of yeast cells, in particular the time evolution of the total displacement of *S. cerevisiae* BY4742 present in PBS or in YPD growth medium. Box plot whiskers within 1.5 IQR of 20 single cells recorded during 12 s; paired Student's t test; **: P<0.0001, *: P<0.001, **: P<0.01, *: P<0.1, ns: not significant.

In a next set of experiments, the capacity of the ONMD method to monitor metabolic changes in yeast upon chemico-physical stimulations was explored. Firstly, the effect of the temperature (in the range of 13 to 35° C.) on *C. albicans, C. lusitaniae*, and *S. cerevisiae* (FIG. 3a) was assessed. For all three yeast strains, a maximal activity was detected at around 30° C. This value is in concordance with the documented optimal growth temperature, i.e. 33-38° C. for *C. albicans* and 30-35° C. for *S. cerevisiae* BY4247. Secondly, the way nutrients affect the ONM activity of the yeast cells was assessed by comparing the total displacement of cells suspended in growth medium to those suspended in phosphate buffered saline (PBS). As depicted in FIG. 3c, the nanomotion activity of the cells in growth medium increased significantly after 1 h, in contrast with the measurements obtained in PBS.

Finally, it was evaluated if the ONMD could be used to perform AFST of surface-attached cells. Therefore. *C. albicans* DSY1024 (sensitive). DSY294 (wild type) and DSY4814 (caspofungin resistant) were strongly attached onto a glass surface coated with concanavalin A (FIGS. 6a-6c upper panels). Concanavalin A is a lectin, which cross-links the yeast cell wall through its mannose glycans to the surface of the glass. In such a case, no significant decrease of the total displacement was detected, contrarily to Syal and co-workers who performed antibiotic susceptibility testing on loosely attached *E. coli* cells. Eventually caspofungin AFST was carried on yeast cells deposited onto an antifouling-coated surface, i.e. PLL-g-PEG treated glass slides. These experiments showed somewhat comparable results to those obtained on untreated glass surfaces (FIGS. 6a-6c). However, a faster significant decrease in nanomotion could be detected for the untreated glass surface in the case of the hypersusceptible and wild-type strain. Untreated glass and PLL-g-PEG coated glass gave comparable results for the resistant strain. Based on these experiments, we can conclude that our method observes the "natural" nanomotion of suspended, non-attached cells.

Numerical analysis was performed in the frequency domain to highlight differences in the oscillation pattern occurring during the life-death transition (FIG. 7a, b). Every frequency range is characterized by its low and high frequency limit. With the present method of recording, the low frequency limit is determined as the reciprocal value of the signal duration, which equals to 0.083 Hz for 12 s. Calculating the high limit is more complex and varies between different cells. The high frequency limit was named as critical frequency ($f_{crit}$) and a procedure for its calculation was devised. These analyses revealed that untreated resistant *C. albicans* cells show a maximum activity in a frequency range (0.083–$f_{crit}$) where $f_{crit}$ varied varying from 0.7 to 1.5 Hz. Interestingly, *C. albicans* DSY294 wild-type cells had also an $f_{crit}$ at a higher frequency (2.5-3.0 Hz) (FIG. 7c) whereas caspofungin treated cells, presented a broadening of their $f_{crit}$ which was most extended for the hypersusceptible (sensitive) DSY1024 cells (FIG. 7d). In that case, an additional $f_{crit}$ around 2 Hz was observed. These results demonstrate that the largest difference of the oscillation pattern in the frequency domain between living and death yeast cells is located in the very low frequency range. These results complement those published by Gimzewski and coworkers who highlighted a periodical motion of *S. cerevisiae* in the range of 0.8-1.6 kHz. These measurements were accomplished by AFM on yeast cells that were mechanically trapped into a filter pore. Unfortunately, our present ONMD setup cannot reach such high sampling rates to confirm or contradict these results.

In order to accelerate the data processing, a deep learning algorithm was developed that detects individual yeast cells (FIG. 3d) and tracks their nanomotion at a subpixel resolution Deep learning models have been widely successful in automated objects and cells detection tasks. A medium-size shallow YOLO architecture was used. Compared to a manual selection of cells, this approach permits to analyse automatically a significantly larger number of cells (100-1000). As a proof of principle, we reanalysed the video data demonstrating the influence of the temperature on the three yeast strains (FIG. 3b). Compared to the 20 manually selected cells per temperature condition used in the first analysis, more cells could be automatically detected: 194 cells (on average 39 cells per condition) were analysed for *C. albicans*, 159 cells (average 32 cells per condition) for *C. lusitaniae*, 147 cells (average 29 cells per condition) for *S. cerevisiae*. As expected, such an increase in the samples size for the analysis resulted in a smaller distribution of the total displacements, and provided a more accurate value for the calculated average displacements (FIG. 3b versus 3a).

In an attempt of further increasing the efficiency of the method and reduce its computational costs, additional experiments were performed with low frequency recording rates (10.5 fps instead of 83 fps). These modifications were motivated by the obtained results which demonstrated that the largest difference between living and death yeast cells occurs at frequencies lower than 4 Hz. We performed the same treatment with ethanol as before for the higher framerate acquisition of 83 fps (FIG. 2c) for *C. albicans, C. glabrata, C. lusitaniae* and *S. cerevisiae* (FIG. 6d). These results show that comparable results can be obtained for smaller data files with faster analysis.

Figure 11A:
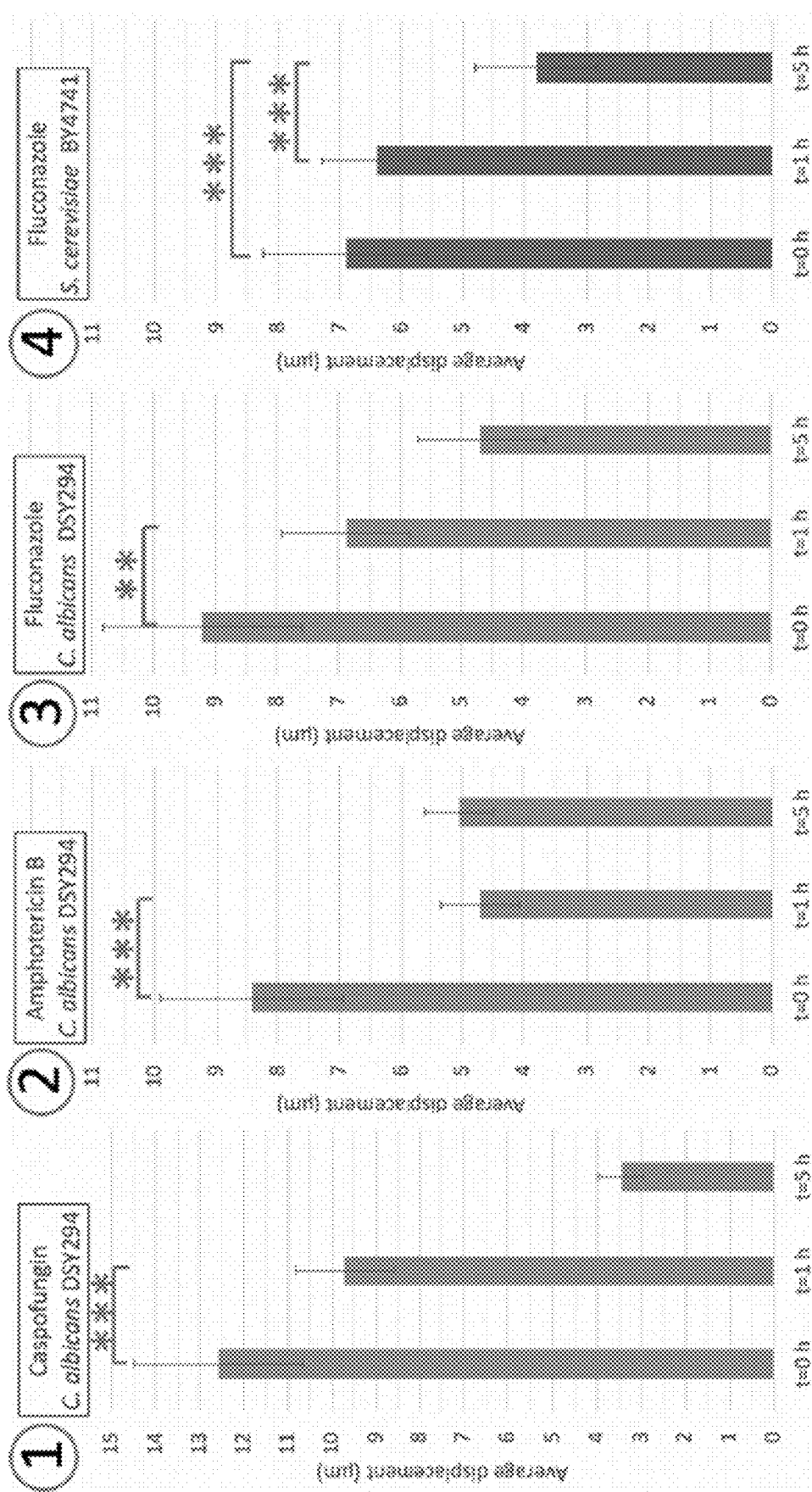
Figure 11B:
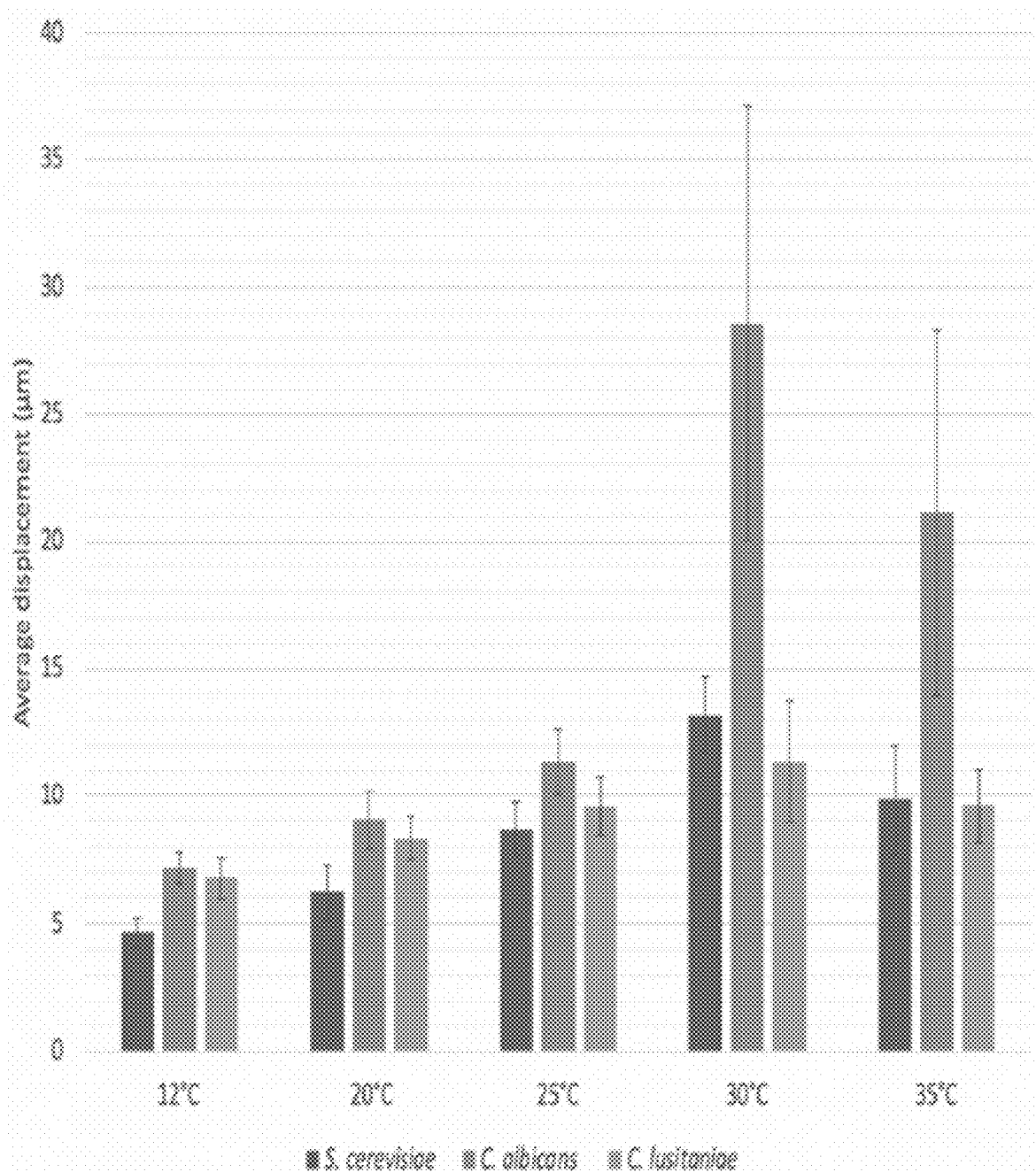

Further by way of illustration, the average displacement of cells exposed to antifungals are studied and shown in FIG. 11a, FIG. 11b and FIG. 12. The 2D displacements of individual cells were determined using a dedicated algorithm that monitors cellular displacements with sub-µm resolution. In the present example, the movement were measured in microwell inserts from Ibidi (Germany), which have a conical shape with a diameter of 400 µm at the bottom. The average displacement of cells exposed to the antifungal was compared to the non-treated control for a few cells and antifungal compounds (FIG. 1A). A Student's t-test was performed to determine if the decrease of movement of the cells is significant. In FIG. 11a, the effect is shown on the average displacement during 12 s measurement as a function of time. The measurements were performed in 4 Ibidi microwells. The antifungal solution was added to the same well at the top and mixing occurred only by diffusion, which increases the time an effect on the viability is observed. The effect is shown for (1) caspofungin on *C. albicans* DSY294 clinical strain (2) amphotericin B on *C. albicans* DSY294, (3) fluconazole on *C. albicans* DSY294 and (4) *S. cerevisiae* BY4741. Error bars represent the standard deviation from the displacement of 20 single cells recorded during 12 s; paired Student's t test; * P<0.001;  P<0.01). The activity of the cells (*C. albicans, C. lusitaniae* and *S. cerevisiae*) as a function of the temperature were also studied. Effect of the temperature on the average displacement for *S. cerevisiae* BY4741, the clinical strains *C. albicans* DSY294 and *C. lusitaniae* DSY4606 is shown in FIG. 11b. Fifteen minutes after the temperature was stabilised after a step increase of the temperature, the movement of 20 single cells per condition was recorded during ~12 s and analysed.

The effect of caspofungin on the average displacement of a wild type, resistant and sensitive *C. albicans*, and *S. cerevisiae* Is shown in FIG. 12. The effect of Caspofungin during 5 h incubation is shown. The caspofungin concentration in YPD medium was 10 µg/l.

The experiments showing measurement movements of cells in 4 wells, illustrate features and advantages of embodiments of the present invention.

As mentioned initially, an AFM-based assay to assess the effects of chemicals on the viability of bacteria has been developed previously [8]. The detection is based on the observation that living organisms oscillate at a nanometric scale and transfer these oscillations to the AFM cantilever onto which they are attached. These oscillations stop as soon as the viability of the cells is compromised. It has been demonstrated that these oscillations are present in living bacteria, yeasts, plant and mammalian cells [9]. The nanomotions of living bacterial cells that are attached to a surface, have been confirmed by using other detection methods such as plasmonic imaging of the z-movement of bacteria [10], tracking the submicron scale x-y movement of attached bacteria [11], sensing of attached bacterial vibrations with phase noise of a resonant crystal [12], and sub-cellular fluctuation imaging [13].

As was also already mentioned, it has been noticed that an optical microscope equipped with a video camera can detect the movements of single yeast cells that are sedimented on a glass surface. Living single yeast cells show a specific cellular movement at the nanometer scale with a magnitude that is proportional to the cellular activity of the cell. We characterized this cellular nanomotion pattern of non-attached single yeast cells using classical optical microscopy. The distribution of the cellular displacements over a short time period are distinct from random movement. The range and shape of such nanomotion displacement distributions change significantly according to the metabolic state of the cell. The analysis of the nanomotion frequency pattern demonstrated that single living yeast cells oscillate at relatively low frequencies of around 2 Hz. The simplicity of the technique should open the way to numerous applications among which antifungal susceptibility tests seems the most straightforward.

FIGS. 13 to 24 further illustrate the present invention. In particular, the nanomotion of non-attached yeast cells using this optical nanomotion detection (ONMD) method was explored. The statistical analysis was further based on Violin and box-and-whisker (10-90 percentile) plots that were created with Prism8 (GraphPad). A Wilcoxon matched-pairs signed rank test was performed to determine the significant differences between conditions (boxplots of mean total displacements over 1000 frames).

The cellular x-y movements were monitored by recording 12 s long movies (1000 frames) taken at a magnification of 400× (FIG. 13). By periodically recording these movies, temporal behavior of the cells was characterized as a function of different chemical and physical stimuli (FIG. 13A-B). To track the cellular movements of single cells, we used a cross-correlation image registration algorithm [14]. The algorithm is based on the initial estimation of the cross-correlation peak between the first and every subsequent frame. It provides a numerical value for the image translation with a sub-pixel (sub-$\mu$m) resolution. The cell displacement for each frame, the trajectories of tracked cells (FIG. 13C) as well as the root mean square of the total displacement (FIG. 13F) were calculated. Single cell nanomotions were characterized by plotting the distribution of the displacements per frame as a violin plot (FIG. 13D). The movements of the set of 20 cells were characterized by plotting grouped cellular displacements per frame as violin plots and the total displacements of 20 cells over 1000 frames as box-and-whisker plots (FIG. 13E).

In a further set of experiments, we compared single-cell nanomotions of Saccharomyces cerevisiae cells that were grown in the presence of nutrients (by growing them in YPD growth medium) to cells that were in a nutrient-free physiological PBS buffer. Single cell displacements were recorded every hour during 4 h (FIGS. 14A-B and 17A-B). Actively growing single cells showed a large distribution of displacements. The distribution of the displacements is not symmetric, and this reflects the non-random behavior of the cells (as could also be observed from the x-y displacements graphs (FIG. 2a-2b)), i.e. cells can make jumps from time to time. This movement behavior is also reflected in the shape of the violin plots that represents the displacements distribution. In this set, a few cells (1 to 3) display a very small displacement distribution and can be classified as inactive. In contrast, significantly more inactive cells were present in the absence of nutrients, especially after 3-4 h of incubation (FIGS. 14B and 17B). This behavior is also reflected in the grouped displacements violin plots (FIG. 14A-8 lower panels) and the total displacements boxplots (FIG. 17C-D). In these last plots, the adaptation of the cells to the new growth condition can clearly be observed, i.e. a significant increase of the total displacement after 1 h, in contrast with the measurements obtained in PBS.

The cellular nanomotions were also compared to the movements of silica beads recorded in the same conditions (FIG. 18A-D). The distributions of the displacements were symmetric. The magnitudes of the movements were much reduced compared to living cells and were of the same order of dead cells (FIG. 18E).

To assess the effect of the temperature on the nanomotion pattern of yeast, we monitored the cellular oscillations at different temperatures in the range of 13 to 35° C. (FIGS. 14C-D and 19). Each strain is characterized by a different distribution of grouped displacement distributions. For both yeast strains, a maximal activity was detected at around 30° C. This value is in concordance with the documented optimal growth temperature of 30-35° C. for *S. cerevisiae* BY4742 [15] and 33-38° C. for *C. albicans* [16]. These experiments demonstrate that the magnitude of the cellular activity is proportional to the magnitude of the distribution of the displacements and the total displacement over 1000 frames.

Next, we characterized the cellular movements of *Candida* and *S. cerevisiae* cells when they are exposed to a killing agent. The *Candida* species can be involved in candidiasis, which is a human fungal infection that can be hard to treat due to the acquired resistance [17]. Some of the evaluated yeast strains were hypersusceptible or resistant to the applied antifungal drugs to challenge their viability. Firstly, we explored the effect of a high ethanol concentration (70%) on *C. albicans, C. glabrata, C. lusitaniae* and *S. cerevisiae* cells. The x-y displacements are quickly and drastically reduced after adding ethanol (FIG. 2a-2b). The displacement distributions of the single cols (FIG. 15), the grouped displacements of 20 cells (FIG. 15E-F, upper panels) and the total displacements (FIG. 15E-F, lower panels) were reduced. Ten minutes after the addition of ethanol, a reduction of the displacements in the set of 20 cells for all strains is observed. *C. glabrata* and—in a lesser extent—*S. cerevisiae* are somewhat more ethanol tolerant than *C. glabrata* and *C. lusitaniae*, since a significant decrease of the total displacement was only observed after 60 min. Ethanol tolerance is strain dependent [18, 19], affects the growth rate and will impair the cell membrane integrity [20], which results in ionic species permeability and leakage of metabolites [21]; and freely diffuses inside the cell, where it directly perturb and denature intracellular proteins [22].

Secondly, we assessed the effect of killing of cells on the change in cellular nanomotions by exposing them to different concentration of various antifungals. The x-y displacements were significantly reduced after treatment of the cells with antifungals (FIG. 2a-2b). The effect of amphotericin B, caspofungin and fluconazole on the cellular movements of *C. albicans* DSY294 wild-type strain is shown in FIGS. 16A-C and 20A-C. The polyene amphotericin 8 selectively binds to ergosterol in the cell membrane and causes the formation of pores (which results in a quicker dead), whereas the azole fluconazole selectively inhibits cytochrome P450-dependent lanosterol-14-a-demethylase and the echinocandin caspofungin inhibits fungal b-1,3- glucan synthase [23]. For all 3 antifungals, a significant decrease in the cellular displacements and total displacement was detected after 1 h treatment. Amphotericin B at a high concentration is very effective since after already 1 h the cellular nanomotion decreased to values close to those recorded on dead cells in the whole set of 20 cells (FIG. 20A) Caspofungin did not affect the nanomotion of the candin-resistant *C. albicans* DSY4614 clinical strain (FIG. 16E) but did kill the hypersusceptible (mutant for efflux systems) *C. albicans* DSY1024 strain (FIG. 16D) (Table 1). The reported caspofungin MIC values for *C. albicans* are in the range of 0.03 to 8 µg/ml (24-26). Fluconazole decreased the cellular nanomotions of *C. albicans* DSY294 significantly after 1 h (FIG. 18C).

To observe the life-dead transition. *C. albicans* DSY294 clinical wild-type strain was exposed to lower amphotericin concentrations, including the minimal inhibitory concentration (MIC) (which has been reported for *C. albicans* DSY strains as 0.5 µg/ml [6, 27]. The total displacements curves show that there is an increase after 1 h for a concentration of 10 µg/ml (FIG. 16F); the increase is reduced after 2 h treatment (FIG. 16G). A similar amphotericin B response was recorded for the *C. albicans* CAF2-1 wild-type strain (FIG. 22). On the single cell level, a larger number of cells show a significantly reduced movement for amphotericin 8 concentration in the range of 0.1 to 0.5 µg/ml (FIG. 21-22), which corresponds to the reported MIC value of 0.3 µg/ml for this strain [24].

To evaluate if the cells interact significantly with the glass surface, which could influence the measured displacements, the cellular nanomotions on a cell-repellent surface (PLL-PEG coated glass surface) were compared to the ones on a non-treated glass surface. Comparable results were obtained for *C. albicans* DSY294 and DSY1024 treated with caspofungin (FIG. 23). The movement of silica beads on a PLL-PEG coated surface showed that there was a small effect on the displacement distribution and the total displacement (FIG. 18A-D). When the *Candida* cells were adhered to the glass surface by concanavalin A, the displacements were reduced strongly and no significant difference between caspofungin treated and non-treated cells could be detected (FIG. 18F-K).

To highlight differences in the oscillation pattern occurring during the life-death transition, we performed numerical analysis in the frequency domain (FIG. 7a-7d). Every frequency range is characterized by its low and high frequency limit. With the present method of recording, the low frequency limit is determined as the reciprocal value of the signal duration, which equals to 0.083 Hz for 12 s. Calculating the high limit is more complex and varies between different cells. We named the high frequency limit as critical frequency ($f_{crit}$) and devised a procedure for its calculation. These analyzes revealed that untreated resistant *C. albicans* cells show a maximum activity in a frequency range (0.083– $f_{crit}$) where $f_{crit}$ varied varying from 0.7 to 1.5 Hz. Interestingly, *C. albicans* DSY294 had also an $f_{crit}$ at a higher frequency (2.5-3.0 Hz) (FIG. 7C) whereas caspofungin treated cells, presented a broadening of their $f_{crit}$, which was most extended for the hypersusceptible DSY1024 cells (FIG. 7D). In that case, we also observed an additional $f_{crit}$ around 2 Hz. These results show that dying cells exposed to low antifungal concentrations, are characterized by an increased cellular oscillation frequency, and the largest difference of the oscillation pattern in the frequency domain between living and death yeast cells is located in the very low frequency range.

Figure 3D:
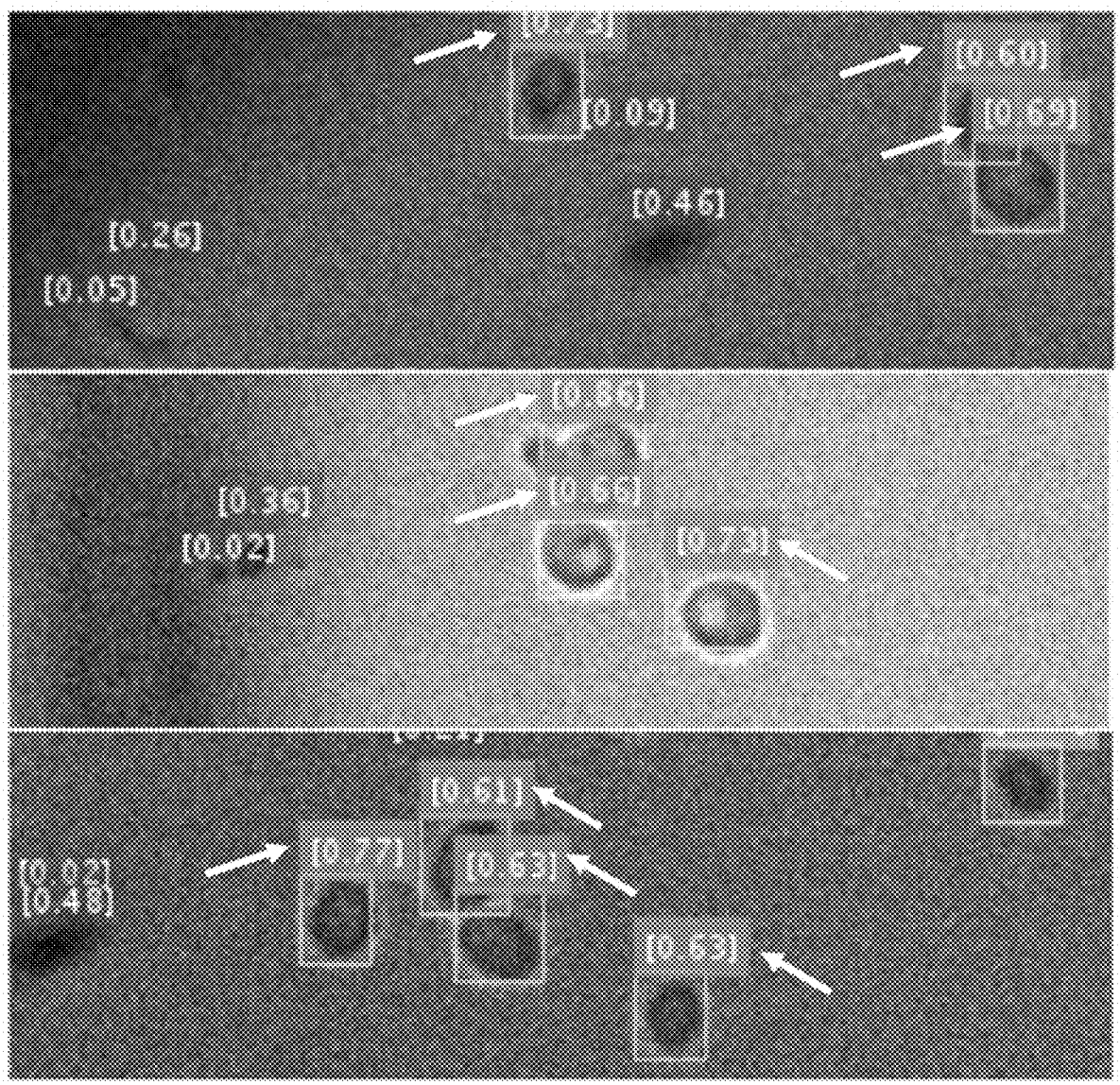
FIG. 3d shows the effect of the temperature and nutritional environment on the optical nanomotion of yeast cells, in particular deep learning cells detection method. Cells automatically detected with high confidence (indicated by arrows) when processing different videos. Although a few cells are missed, most of them are property detected with high confidence. Cells indicated with white arrows denotes high confidence cells, the cell indicated with a black arrow denotes in threshold confidence, detected artifacts are indicated with low values in brackets without a surrounding square.

The data processing was further accelerated by using a deep learning algorithm that detects individual yeast cells (FIG. 3d). Deep learning models have been widely successful in automated objects [28, 29] and cells detection [30, 31] tasks. Compared to a manual selection of cells, this approach could permit to analyze automatically a significantly larger number of cells (100-1000). The developed algorithm is based on a medium-size shallow YOLO [30] architecture.

This newly developed ONMD method for AFST used in this example was based on basic laboratory material, i.e. an optical microscope, a camera and a computer. The technique is label free and does not require the attachment of the living sample onto a substrate. It permits to rapidly determine antifungal susceptibility and metabolic activity of numerous yeast species; and can probably be extended to other microorganisms such as bacteria and to mammalian cells. The technique also permitted to highlight that living yeast cells oscillate at relatively low frequencies, i.e. below 4 Hz. The method can address the nanomotion pattern of single cells as well as whole cellular populations. ONMD has the potential to detect a single resistant cell in a large population. A limitation of the current ONMD method is that only the x-y movements are recorded. The measurement envelope could be extended by considering also the z axis movement [10], which will further increase the sensitivity of the method.

We could link the cellular nanomotions of single yeast cells to its metabolic activity by comparing the nanomotions of the cells in the presence and absence of nutrients, as well as by detecting a maximum cellular movement at the optimal growth temperature. Living single-cell nanomotions show a non-random behavior as was clear from the x-y displacements graphs and the distribution of the displacements during 1000 frames.

The nanomotion analysis of increasing amphotericin B concentration on *C. albicans* DSY294 and *C. albicans* CAF2-1 showed that the analysis based on the distribution of the displacements per frame of single cells seems to be more sensitive than those based on the total displacement of the whole cellular population. The effect of concentrations as low as the MIC of this antifungal became noticeable in a population of 20 cells. Additionally, the results showed that at amphotericin B concentrations of around 10 times the MIC, the cellular nanomotion is increased. This indicates that the mechanism of action of amphotericin B (which binds selectively to ergosterol in the cell membrane and causes the formation of pares [32]) increases the movement of the cells, i.e, the antifungal action increases the metabolic activity of the cells, probably due to an increased activity of the efflux pumps. An increase of the nanomotion (measured by the AFM-cantilever method) of the bacterium *Bordetella pertussis* for the antibiotic was also previously observed [33].

The analysis of the nanomotion frequency pattern demonstrated that single living yeast cells oscillate at relatively low frequencies of around 2 Hz. These results complement those published by Gimzewski and coworkers [34] who highlighted a periodical motion of the *S. cerevisiae* cell wall in the range of 0.8-1.6 kHz. These measurements were accomplished by AFM on yeast cells that were mechanically trapped into a filter pore. An ultrasonic excitation and interferometric motion detection permitted to detect resonance frequencies of single *S. cerevisiae* cells in the range of 330 kHz, which correspond to rigid body oscillations of the cell [35]. Such high frequency ranges are too high to be measured with our optical microscopy setup. Therefore, the low frequency oscillations that we observed, probably correspond to the whole-body displacements of single yeast cells. Future experiments involving high speed optical microscopy and AFM-based measurements should highlight the full spectrum of cellular oscillations and a possible contribution of low frequency cell wall oscillations.

The molecular processes that could cause the observed oscillations, have not been investigated yet in detail Additional experiments consisting in blocking or activating molecular actors (processes) would permit to better understand the observed phenomena. The nanomotion signal is made of vibrations arising from many metabolically-related sources that combine energy consumption with local movement or molecule redistributions[38]. Cellular nanomotion could arise from processes such as DNA replication, DNA transcription, protein assembly, cytoskeleton rearrangement, ionic pumps activity, organelle transport, etc. The involvement of the cytoskeleton has already been demonstrated by depolymerizing the actin cytoskeleton of osteoblasts by cytochalasin, which resulted in a reduced cellular movement (as measured by the AFM-cantilever method) [9]. Also conformational changes of proteins (as was demonstrated for human topoisomerase II [37]) could contribute to nanomotion.

By automatizing the cell recognition using a deep learning algorithm, we could avoid manual cell detection and extend the number of analysed cells and reduce the processing time. Additionally, this opens the way to analyze a larger population of cells. Future developments will include dedicated microfluidic chip development and software optimization to run the acquisition and/or the data processing steps onto a low-end computer. These developments could eventually lead to an easy operational mobile device that can be directly implemented in hospitals or even in remote doctor's practices in developing world countries where it will allow to perform antifungal susceptibility testing in the earliest possible treatment stage and make the appropriate decision for a personalized effective antifungal therapy. An alternative for the software used may in one example be MobileNet instead of the YOLO deep learning architecture, to run the acquisition and/or the data processing steps onto a low-end computer.

In the example discussed above, strains and cell growth were as follows:

AN yeast strains (Table 1) were cultured by inoculating 10 ml of YPD (10 g/l yeast extract, 20 g/l peptone, 20 g/l dextrose) medium with a colony from a YPD agar (20 g/l) plate. The cultures were grown overnight in Erlenmeyer flasks (30° C. and 200 rpm). The overnight cultures were 10- to 20-fold diluted in 5 ml YPD medium to obtain an $OD_{600}$ nm of 0.5 and were then allowed to grow in Erlenmeyer flasks for 1 h at 30° C. and 200 rpm. The cultures were further diluted afterwards, depending on the cell concentration ($OD_{600nm}$ value) to obtain an optimal number of cells for visualisation.

In the example, the optical nanomotion experiment was performed as follows:

Ten µl of each yeast cell culture was dispensed in one of the microwells, using a 4 Well FulTrac micro-Insert (ibidi, Germany) in an imaging micro-dish (Ibidi, Germany). The yeast cells were allowed to sediment for a period of 10 min before starting the measurement. The movement of cells was observed by taking movies of 1000 frames with a framerate of 84 fps using an EMCCD camera (Andor iXon, Oxford Instruments) using a Nikon TE-2000 microscope with a 40× objective. The Petri dish was kept at 30° C. using a microscope stage top incubator (ibidi, Germany).

The effect of ethanol on the viability of the cells was compared with cells grown in YPD medium as a reference. Therefore, first cell nanomotion videos were recorded and next (after approximately 1 min), 200 µl of ethanol (70% v/v) was added to the top chamber of the 4 micro-Insert wells. Videos were recorded every hour during a period of 5 h. Caspofungin, amphotericin B and fluconazole were used as antifungals in the antifungal susceptibility testing, i.e. to assess their effect on cell viability. Before starting the treatment with the antifungal, reference (no treatment) videos were recorded of yeast cells in YPD medium (time=0 h). Then (at time=1 min) 200 µl of a certain concentration of antifungal was added to the chamber (200 µl) above the 4 microwells. Measurements were taken every hour during a period of 5 h. As abiotic reference particles, silica microbeads (monodisperse silica standard, Whitehouse Scientific) with a diameter of 3 µm were used. The beads were dissolved in YPD medium and the measurements were performed at 30° C.

For the experiments where the effect of the temperature on the metabolism was evaluated, the temperature inside the microwells was controlled by adapting the temperature of water (from a recirculating water bath) circulating around the microwells. The temperature was successively adapted from 13° C. to 20, 25, 30 and finally 35° C. The yeast cells were allowed to adapt during 20 min to each temperature before measuring the nanomotion of the cells. For the experiments where the cell activity in PBS (phosphate buffered saline; 8 mg/ml NaCl, 0.20 mg/ml KCl, 1.44 mg/ml $Na_2HPO_4$, 0.24 mg/ml $KH_2PO_4$) was compared to YPD growth medium, the overnight cultured cells were 1000-fold diluted in either YPD medium or PBS, and immediately dispensed in the microwells. The nanomotions of yeast cells were measured every hour during 4 h. For the experiments with glass surface treatment, the glass surface was coated with concanavalin A (2 mg/ml. Sigma) or PLL-g-PEG (0.1 mg/ml, SuSoS AG, Switzerland) by incubating the glass surface for 30 min with the coating solutions.

The nanomotion detection software used in the current example was as follows:

The optical nanomotion detection algorithm calculates the cell displacement for each frame and saves the trajectories of tracked cells as well as the root mean square of the displacement to a MS Excel file. The main part of the program is based on the algorithm of Guizar-Sicairos et al.[14], ported from Matlab to Python in the open source image processing library sci-kit image [38]. The Python package nd2 reader (Verweij R, Online: http://www.lighthacking.nl/nd2reader/) was employed to import the videos in the ND2 Nikon format.

The Deep learning cell detection algorithm used was as follows:

The described nanomotion analysis previously described starts from the position of each individual cell, which is currently provided through a manual selection of the bounding box of a cell in the first video-frame. However, the number of videos and cells present in the videos can be considerably large, especially when determining the MIC or the impact of different temperature conditions. More importantly, providing cell detection at every few frames instead of only in the first video-frame, allows rectifying the position of those cells that drifts away from their initial positions. In these cases, manual detection efforts could span over several hours for multiframe annotations, and thus must be replaced by an automatic detection process of the cells. Therefore, we decided to use a deep learning algorithm, i.e. a medium-sized YOLO architecture, to automatize cell detection. The training process is performed using a set of 50,000 synthetic cell images randomly generated. These synthetic images, obtained using a phase contrast imaging model we previously proposed [39], look very similar compared to the cell images obtained with the microscope in terms of cells distribution, illumination and imaging artefacts. Once the YOLO model has been trained, it is then used to automatically detect cells in real microscopic images, and each detection is then used as initial position to calculate the optical nanomotion with the cross-correlation algorithm previously described. The overall processing pipeline starts from a bulk of video sequences and performs a per-frame automated single-cell detection. Next, the results are refined by averaging the cells position and detection confidence across frames to correct abrupt changes between consecutive frames. Finally, the position of cells detected with high confidence (i.e. >0.6) is provided as input to the nanomotion analysis algorithm (FIG. 3d).

Further Automation of the process was as follows:

The overall process consists of reading a sequence of frames as images containing the cells and applying the above described cell detection process every 10 frames to obtain a set of bounding boxes indicating the location of each individual cell automatically detected. Based on their positions, the cells are tracked across time as the video analysis process unfolds. At the end, in a subsequence refinement stage, one finds the contours of cells indicated by the bounding boxes in order to confirm that their centre roughly corresponds to that of the bounding boxes, and any mismatch is then used to penalize the cells detection confidence proportionally. In addition, the bounding boxes position and detection confidence is averaged across frames to avoid sharp changes the cells detection positions.

The calculation of the frequency region of optically recorded cell movements and the critical frequency was as follows:

The approach based on calculating FFT amplitude spectrum, computed for two signals of cell movements—one in the horizontal ("x"), the other in the vertical ("y") direction—was developed to calculate the frequency region and critical frequency of optically recorded yeast cell movements. We named this method Double Region Interpolation Method (DRIM). The idea is two perform two linear interpolations on these averaged amplitudes, in two different frequency regions. One should be done on the wideband noise part of the spectrum, sufficiently distant from the cell activity region (e.g. 5-10 Hz). The other is performed on the low frequency region, where the cell is active. Crossing point between these two straight lines determines the upper critical frequency of the cell activity region. The approach to determine the frequency range of the cell movements is based on the direct application of the FFT algorithm on two detrended signals: one obtained for movements in the horizontal (x), the other in the vertical (y) direction. Both x and y spectra have similar profiles; however, some amplitudes were slightly different. We therefore derived their frequency-by-frequency average in order to equally incorporate frequencies of cell movements in both directions. Since signals were recorded with a sampling frequency of 83 frames/s, we visually inspected frequencies up to 41 Hz, and confirmed that cell movements are confined to a few Hz only (FIG. 7a insert). As each signal contained 1000 samples (duration of 12.0482 s), each FFT spectrum was taken from the first 12 s, resulting in a frequency resolution of 0.083 Hz. In order to maintain his resolution. FFT was applied to each 12 s signal as a whole, thus avoiding any shorter moving windows. The task of determining the frequency range of cell movements implies assessing both its upper and lower critical frequencies.

FIG. 24 shows a cross-correlation program, in particular a manual selection of individual cells that will be analysed by the cross-correlation algorithm. Two boxes are positioned in such a way that they enclose at least part of the cell. Box 1 (touched by white arrow) is used for x axis shift tracking, box 2 (touched by black arrow) is used for y-axis shift tracking.

The data availability was as follows:

The data that support the plots within this paper and other findings of this study are available from the corresponding authors upon request.

TABLE 1

Yeast strains used in this study.

| Microorganism | Type | Strains | Characteristics | Genotype/Description | Ref |
|---|---|---|---|---|---|
| Candida albicans | Lab Strain | CAF2-1 | Wild type strain | Δura3::imm434/URA3 | [3] |
| Candida albicans | Lab strain | DSY1024 | Mutant for efflux systems | Δcdr1:hisG/Δcdr1::hisG; Δcdr2::hisG; Δflu1::hisG/Δflu1::hisG; Δmdr1::hisG-URA-3-hisG/Δmdr1::hisG | [4] |
| Candida albicans | Lab strain | DSY2621 | Mutant for efflux systems, sensitive to stress | Δcdr1:hisG/Δcdr1::hisG; Δcdr2::hisG; Δflu1::hisG/Δflu1::hisG; Δmdr1::hisG/Δmdr1::hisG; Δcna::hisG-URA3-hisG | [5] |
| Candida albicans | Clinical strain | DSY294 | Azole-susceptible strain | Wild type | [2] |
| Candida albicans | Clinical strain | DSY296 | Azole-resistant strain | Mutant for TAC1 and ERG11 | [2] |
| Candida albicans | Clinical strain | DSY4614 | Candin-resistant strain | FSK1 mutant P649H | [7] |
| Candida glabrata | Clinical strain | DSY562 | Azole-susceptible strain | Wild type | [6] |
| Candida lusitaniae | Clinical strain | DSY4606 | Wild type strain | Wild type | [7] |
| Candida lusitaniae | Clinical strain | DSY4590 | FKS1, S638Y, erg4 Resistant to candins and amphotericin B | FKS1 mutant S638Y, loss of function in ERG4 | [7] |
| Saccharomyces cerevisiae | Lab strain | BY4742 | Wild type strain | MATα his3Δ1 leu2Δ0 lys2Δ0 ura3Δ0 | [1] |

[1] Brachmann C B. Davies A, Cost G J. Caputo E, Li J, Hieter P, Boeke J D. Designer deletion strains derived from *Saccharomyces cerevisiae* S288C: a useful set of strains and plasmids for PCR-mediated gene disruption and other applications. Yeast. 1998 Jan. 30:14(2):115-32.

[2] Coste A T, Karababa M, Ischer F, Bille J, Sanglard D. TAC1, transcriptional activator of CDR genes, is a new transcription factor involved in the regulation of *Candida albicans* ABC transporters CDR1 and CDR2. Eukaryot Cell. 2004 December; 3(6):1639-52.

[3] Fonzi W A, Irwin M Y. Isogenic strain construction and gene mapping in *Candida albicans*. *Genetics*. 1993 July; 134(3):717-728.

[4] Marchetti O, Majcherczyk P A, Glauser M P, Bille J, Moreillon P, Sanglard D. Sensitive bioassay for determination of fluconazole concentrations in plasma using a *Candida albicans* mutant hypersusceptible to azoles. Antimicrob Agents Chemother. 2001 March; 45(3): 696-700.

[5] Rochat B. Pascual A, Pesse B, Lamoth F. Sanglard D, Decosterd L A, Bille J. Marchetti O. Ultra-performance liquid chromatography mass spectrometry and sensitive bioassay methods for quantification of posaconazole plasma concentrations after oral dosing. Antimicrob Agents Chemother. 2010 December; 54(12):5074-81.

[6] Sanglard D. Ischer F, Calabrese D, Majcherczyk P A, Bille J. The ATP binding cassette transporter gene CgCDR1 from *Candida glabrata* is involved in the resistance of clinical isolates to azole antifungal agents. Antimicrob Agents Chemother. 1999 November; 43(11):2753-85.

[7] unpublished.

[8] G. Longo, L. Alonso-Sarduy, L. M. Rio, A. Bizzini, A. Trampuz, J. Notz, G. Dietler, S. Kasas, Rapid detection of bacterial resistance to antibiotics using AFM cantilevers as nanomechanical sensors. *Nat. Nanotechnol.* 8, 522-528 (2013).

[9] S. Kasas, F. S. Ruggeri, C. Benadiba, C. Maillard, P. Stupar, H. Tournu, G. Dietler. G. Longo, Detecting nanoscale vibrations as signature of life. *Proc. Natl. Acad. Sci.* 112, 378-381 (2015).

[10] K. Syal, R. Iriya, Y. Yang, H. Yu, S. Wang, S. E. Haydel, H.-Y. Chen, N. Tao, Antimicrobial susceptibility test with plasmonic imaging and tracking of single bacterial motions on nanometer scale. *ACS Nano.* 10, 845-52 (2016).

[11] K. Syal, S. Shen. Y. Yang, S. Wang. S. E. Haydel, N. Tao, Rapid antibiotic susceptibility testing of uropathogenic *E. coli* by tracking submicron scale motion of single bacterial cells. *ACS Sensors.* 2, 1231-1239 (2017).

[12] W. L. Johnson. D. C. France, N. S. Rentz, W. T. Cordell. F. L. Walls, Sensing bacterial vibrations and early response to antibiotics with phase noise of a resonant crystal. *Sci. Rep.* 7, 12138 (2017).

[13] C. R. Bermingham, I. Murillo, A. D. J. Payot, K. C. Balram, M. B. Kloucek, S. Hanna, N. M. Redmond, H. Baxter, R. Oulton, M. B. Avison. M. Antognozzi, Imaging of sub-cellular fluctuations provides a rapid way to observe bacterial viability and response to antibiotics. *bioRxiv.* 460139 (2018).

[14] M. Guizar-Sicairos, S. T. Thurman, J. R. Fienup, Efficient subpixel image registration algorithms. *Opt. Lett.* 33, 156-158 (2008).

[15] J.-S. Lee, E.-H. Park, J.-W. Kim, S.-H. Yeo. M.-D. Kim. Growth and fermentation characteristics of *Saccharomyces cerevisiae* NK28 isolated from kiwi fruit. *J. Microbiol. Biotechnol.* 23, 1253-1259 (2013).

[16] M. Lemos-Carolino, A. Madeira-Lopes, N. Van Uden. The temperature profile of the pathogenic yeast *Candida albicans*. *Z. Allg. Wikrobiol.* 22, 705-709 (1982).

[17] D. Sanglard, Emerging Threats in Antifungal-Resistant Fungal Pathogens. *Front Med.* 3, 11 (2016).

[18] M. L. Zeuthen, N. Dabrowa, C. M. Anlebo, D. H. Howard, Ethanol tolerance and the induction of stress proteins by ethanol in *Candida albicans*. *J. Gen. Microbiol.* 134, 1375-1384 (1988).

[19] A. K. Pandey, M. Kumar. S. Kumari, P. Kumari, F. Yusuf, S. Jakeer, S. Naz, P. Chandna, I. Bhatnagar, N. A. Gaur, Evaluation of divergent yeast genera for fermentation-associated stresses and identification of a robust sugarcane distillery waste isolate *Saccharomyces cerevisiae* NGY10 for lignocellulosic ethanol production in SHF and SSF *Blotechnol. Biofuels.* 12, 40 (2019).

[20] M. Schiavone, C. Formosa-Dague, C. Elsztein, M.-A. Teste, H. Martin-Yken, M. A. De Morais, E. Dague, J. M. François, Evidence for a role for the plasma membrane in the nanomechanical properties of the cell wall as revealed by an atomic force microscopy study of the response of *Saccharomyces cerevisiae* to ethanol stress. *Appl. Environ. Microbiol.* 82, 4789-4801 (2016).

[21] D. Stanley, A. Bandara, S. Fraser, P. J. Chambers, G. A. Stanley, The ethanol stress response and ethanol tolerance of *Saccharomyces cerevisiae*. *J. Appl. Microbiol.* 109, 13-24 (2010).

[22] C, M. Henderson, D. E. Block, Examining the role of membrane lipid composition in determining the ethanol tolerance of *Saccharomyces cerevisiae*. *Appl. Environ. Microbiol.* 80, 2966-2972 (2014),

[23] R. Willaert, Micro- and nanoscale approaches in antifungal drug discovery. *Fermentation.* 4, 43 (2018).

[24] D. Sanglard, F. Ischer, O. Marchetti, J. Entenza, J. Bille. Calcineurin A of *Candida albicans*: involvement in antifungal tolerance, cell morphogenesis and virulence. *Mol. Microbiol.* 48, 959-976 (2003).

[25] N. P. Wiederhold. J. L. Grabinski, G. Garcia-Effron, D. S. Pelin, S. A. Lee, Pyrosequencing to detect mutations in FKS1 that confer reduced echinocandin susceptibility in *Candida albicans*. *Antimicrob. Agents Chemother.* 52, 4145-4148 (2008).

[28] R. A. Cordeiro, C. E. C. Teixeira. R. S. N. Brilhante, D. S. C. M. Castelo-Branco, M. A. N. Paiva, J. J. Giffoni Leite, D. T. Lima, A. J. Monteiro, J. J. C. Sidrim, M. F. G. Rocha, Minimum inhibitory concentrations of amphotericin B, azoles and caspofungin against *Candida* species are reduced by farnesol. *Med. Mycol.* 51, 53-59 (2013).

[27] L. Vale-Silva, E. Beaudoing, V. D. T. Tran, D. Sanglard, Comparative genomics of two sequential *Candida glabrata* clinical isolates. *G3 (Bethesda)*, 7, 2413-2426 (2017).

[28] L. Castrejón, K. Kundu, R. Urtasun, S. Fidler, Annotating Object Instances with a Polygon-RNN. *IEEE Conference on Computer Vision and Pattern Recognition (CVPR)*,
4485-4493(2017).

[29] O. Russakovsky, J. Deng. H. Su, J. Krause, S. Satheesh, S. Ma, Z. Huang, A. Karpathy, A. Khosla, M. Bernstein, A. C. Berg, L. Fei-Fei, ImageNet large scale visual recognition challenge. *Int. J. Comput. Vis.* 115, 211-252 (2015).

[30] J. Redmon, S. Diwala, R. Girshick. A. Farhadi, You Only Look Once: unified, real-time object detection. *IEEE Conference on Corrupter Vision and Pattern Recognition (CVPR)*, 779-788 (2016).

[31] O. Ronneberger, P. Fischer, T. Brox, in *Lecture Notes in Computer Science* (Springer Verlag, 2015), vol. 9351, pp. 234-241.

[32] J. Brajtburg, W. G. Powderly, G. S. Kobayashi, G. Medoff, Amphotericin B: Current understanding of mechanisms of action. *Antimicrob. Agents Chemother.* 34 183-188 (1990).

[33] M. I. Vilalba, P. Stupar, W. Chomicki, M. Bertacchi, G. Dietler, L. Arnal, M. E. Vela, O. Yantomo, S. Kasas, Nanomotion detection method for testing antibiotic resistance and susceptibility of slow-growing bacteria. *Small.* 14, 1702671 (2018).

[34] A. E. Pelling, S. Sehati, E. B. Graila, J. S. Valentine, J. K. Gimzewski, Local nanomechanical motion of the cell wall of *Saccharomyces cerevisiae*. *Science* 305, 1147-1150 (2004).

[35] B. Farzi, C. Cetinkaya, Micromechanical and surface adhesive properties of single *Saccharomyces cerevisiae* cells. *J. Phys. D. Appl. Phys.* 50, 375401 (2017).

[36] A. C. Kohler, L. Venturelli, G. Longo, G. Dietier, S. Kasas, Nanomotion detection based on atomic force microscopy cantilevers. *Cell Suf.* 5, 100021 (2019).

[37] L. Alonso-Sarduy, P. De Los Rios, F. Benedetti, D. Vobornik, G. Dietier, S. Kasas, G. Longo, Real-time mentioning of protein conformational changes using a nano-mechanical sensor. *PLoS One.* 9, e103874 (2014).

[38] S. Van Der Walt, J. L. Schönberger, J. Nunez-Iglesias, F. Boulogne, J. D. Warner, N. Yager, E. Gouillart, T. Yu. Scikit-image: Image processing in python. *PeerJ.* 2, e453 (2014).

[39] M. Alioscha-Perez. R. Willaert, H. Tournu, P. Van Dijck. H. Sahli, in *Lecture Notes in Computer Science* (Springer, Berlin, Heidelberg, 2013), vol. 8259 LNCS. pp. 25-32.

[40] A. Trujillo-Pino, K. Krissian, M. Alemán-Flores. D. Santana-Cedrés, Accurate subpixel edge location based on partial area effect. Image Vis. Comput. 31, 72-90 (2013).

The invention claimed is:

1. A method for deriving particle characteristics, the method comprising imaging the movement of at least one free-floating particle in a liquid environment at at least one moment in time, determining for at least one moment in time at least one movement parameter based on the imaged movement of the free-floating particles in the liquid environment, deriving from the at least one movement parameter at least one characteristic of the at least one particle, wherein said method comprises:

imaging the movement of the at least one free-floating particle at at least two moments in time, whereby at least a first imaged movement and a second imaged movement is obtained, and determining a change between the first imaged movement and the second imaged movement, and wherein said change is indicative of the movement parameter, wherein the change corresponds to at least one of a spatial displacement of the free-floating particle, a velocity associated with the spatial displacement of the free-floating particle, an acceleration associated with the spatial displacement of the free-floating particle, a distribution of the spatial displacement of the free-floating particle, a distribution of the velocity associated with the spatial displacement of the free-floating particle, or a distribution of the acceleration associated with the spatial displacement of the free-floating particle, wherein at least one of the spatial displacement, the velocity associated with the spatial displacement, the acceleration associated with the spatial displacement, the distribution of the spatial displacement, the distribution of the velocity associated with the spatial displacement, or the distribution of the acceleration associated with the spatial displacement is determined as a function of time, is subjected to a space-to-frequency conversion is converted into a frequency domain so as to obtain one or more frequencies, and wherein the characteristic of the particle is derived from said one or more frequencies.

2. The method according to claim 1, wherein the movement of the at least one free-floating particle is imaged as a function of time, and wherein the movement parameter is determined as a function of time.

3. The method according to claim 1, wherein at least one of:

i) the spatial displacement is determined with respect to at least one spatial direction, and ii) the spatial displacement is determined with respect to two or more spatial directions.

4. The method according to claim 1, wherein an amount of the spatial displacement is determined, and wherein the characteristic of the particle is derived from said amount, and/or wherein the amount of the spatial displacement is determined within a certain period of time.

5. The method according to claim 1, wherein the spatial displacement corresponds to a translation of the free-floating particle and/or to a rotation of the free-floating particle and/or to a deformation of the free-floating particle.

6. The method according to claim 1, wherein at least one of i) a spatial displacement of the entire free-floating particle or of at least one part of the free-floating particle is determined, ii) a spatial displacement of the entire free-floating particle is determined from the spatial displacement of a centre of mass of the particle, or iii) a spatial displacement of at least one part of the free-floating particle is determined from a modification of a shape of the particle.

7. The method according to claim 1, wherein the spatial displacement is determined using a cross-correlation algorithm.

8. The method according to claim 1, wherein the movement parameter is determined from the imaged movement of a single particle, or wherein the movement parameter is determined from the imaged movement of two or more particles.

9. The method according to claim 1, further comprising selecting one or more particles for the determination of the movement parameter, wherein said selection corresponds to a manual selection and/or to an automatic selection.

10. The method according to claim 1, wherein the at least one free-floating particle is provided in a stationary liquid environment and/or in a flowing liquid environment, and/or wherein the liquid environment is subject to a forced convective flow, and/or wherein the liquid environment is provided in a limiting element such as a chamber or a reservoir or a channel or wherein the liquid environment is provided in an unlimited manner.

11. The method according to claim 1, wherein the at least one free-floating particle is subjected to one or more chemical stimuli and/or one or more physical stimuli, and wherein the movement of the at least one free-floating particle is imaged before and/or during and/or after the action of said one or more chemical stimuli and/or physical stimuli.

12. The method according to claim 1, wherein one or more compounds are added to the liquid environment, and wherein an impact of the one or more compounds on the at least one free-floating particle is derived from the movement parameter.

13. The method according to claim 12, wherein the one or more compounds are essentially immiscible with the liquid environment, and/or wherein the one or more compounds are provided in one or more further compounds, and/or wherein the one or more compounds correspond to one or more agents such as antibiotics or antifungals.

14. The method according to claim 1, wherein the movement of the at least one free-floating particle is imaged with at least one optical sensor.

15. The method according to claim 14, wherein the at least one optical sensor images the movement of the at least one free-floating particle with a frame rate of 1 microsecond or more, preferably 1 second or more, more preferably of 10 seconds or more, and/or wherein the at least one optical sensor images the movement of the at least one free-floating particle at a sub-pixel resolution.

16. The method according to claim 14, wherein the at least one optical sensor is stationary during the imaging of the movement of the at least one free-floating particle or wherein the at least one optical sensor is moved during the imaging of the movement of the at least one free-floating particle.

17. The method according to claim 14, wherein the liquid environment is placed directly onto the at least one optical sensor.

18. The method according to claim 1, wherein the movement of the at least one free-floating particle is imaged while being magnified by at least one magnifying device such as a microscope.

19. The method according to claim 1, wherein the movement parameter is determined while the movement of the particle is imaged and/or after the movement of the particle is imaged, and/or wherein the characteristic of the particle is derived from the movement parameter while the movement of the particle is imaged and/or after the movement of the particle is imaged.

20. The method according to claim 1, wherein the method comprises, at a plurality of moments in time, imaging the movement of at least one free-floating particle by recording a video over a predetermined period of time.

21. The method according to claim 1, wherein the at least one free-floating particle is a particle not bound to a surface of an object or to a surface of a larger particle.

22. The method according to claim 1, wherein at least one of:

i) the movement is an oscillation and wherein the movement parameter is an oscillation movement parameter, and ii) the method comprises registering different images.

23. The method according to claim 1, wherein the method comprises using a neural network and/or using a deep learning technique, and/or wherein the method comprises detection of at least one particle using a trained model.

24. The method according to claim 1, wherein the liquid environment is a diffusion environment wherein the movement of the particles is not disturbed by convection, and/or wherein the liquid environment is a natural fluid such as biological fluid, and/or wherein the liquid environment is an artificial fluid.

25. The method according to claim 1, wherein a characteristic of the at least one particle is a viability or a metabolic activity or a level of metabolic activity or a metabolic state or a vitality or a sensitivity or a resistance of the at least one particle.

26. The method according to claim 1, wherein deriving from said movement parameter a characteristic of the at least one particle comprises taking into account that the amount of movement of the particles is proportional with viability and/or a metabolic activity and/or a level of metabolic activity and/or a vitality and/or a sensitivity and/or a resistance of the at least one particle.

27. The method according to claim 1, wherein the at least one particle is at least one cell and/or at least one organelle.

28. A non-transient computer-readable medium comprising a computer program code with instructions which, when executed by a computer system, causes the computer system to carry out the method according to claim 1.

29. A system for deriving particle characteristics, the system comprising at least one optical sensor for imaging movement of at least one free-floating particle in a liquid environment at at least one moment in time, and a processor comprising an input means for obtaining the imaged movement of the at least one free-floating particle, and wherein the processor is configured to perform the method according to claim 1.

30. A method comprising using the system according to claim 29 for at least one antibiotic susceptibility testing, antifungal susceptibility testing, characterizing cell viability, metabolism monitoring, diagnostics, drug screening and antimitotic drug susceptibility testing.

31. The method according to claim 1, wherein at least one of the spatial displacement, the velocity associated with the spatial displacement, the acceleration associated with the spatial displacement, the distribution of the spatial displacement, the distribution of the velocity associated with the spatial displacement, or the distribution of the acceleration associated with the spatial displacement as a function of time is converted into the frequency domain using at least one of: a conversion algorithm, a wavelet, or Fast Fourier Transformation.

* * * * *